United States Patent
Toutov et al.

(10) Patent No.: US 10,059,726 B2
(45) Date of Patent: Aug. 28, 2018

(54) BASE-CATALYZED SILYLATION OF TERMINAL OLEFINIC C—H BONDS

(71) Applicant: CALIFORNIA INSTITUTE OF TECHNOLOGY, Pasadena, CA (US)

(72) Inventors: Anton Toutov, Pasadena, CA (US); Wenbo Liu, Pasadena, CA (US); Kerry Betz, Boulder, CO (US); Alexey Fedorov, Zurich (CH); Brian M. Stoltz, San Marino, CA (US); Robert H. Grubbs, South Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 32 days.

(21) Appl. No.: 15/166,405

(22) Filed: May 27, 2016

(65) Prior Publication Data
US 2016/0347776 A1    Dec. 1, 2016

Related U.S. Application Data

(60) Provisional application No. 62/168,120, filed on May 29, 2015.

(51) Int. Cl.
*C07F 7/08* (2006.01)
(52) U.S. Cl.
CPC .................................. *C07F 7/0829* (2013.01)
(58) Field of Classification Search
None
See application file for complete search history.

(56) References Cited

U.S. PATENT DOCUMENTS

| | | | |
|---|---|---|---|
| 9,000,167 | B2 | 4/2015 | Grubbs et al. |
| 2013/0096274 | A1 | 4/2013 | Kameswara et al. |
| 2016/0046653 | A1 | 2/2016 | Toutov et al. |
| 2016/0060278 | A1 | 3/2016 | Toutov et al. |
| 2016/0176772 | A1 | 6/2016 | Toutov et al. |

FOREIGN PATENT DOCUMENTS

WO    WO 2014/055587 A1    4/2014

OTHER PUBLICATIONS

Denmark et al., "Sequential Cross-Coupling of 1,4-Bis-silylbutadienes: Synthesis of Unsymmetrical 1,4-Disubstituted 1,3-Butadienes",Journal of The American Chemical Society, 2005, 127, 8004-8005.
Dudley et al., "Synthesis of (+)-Dihydro-epi-deoxyarteannuin B", Organic Letters, 2007, 9, 2839-2842.
Hilt et al., "Regioselective Cobalt-Catalyzed Alder-ene Reaction toward Silicon- and Boron-Functionalized Building Blocks",Organic Letters, 2011, 13(2), 304-307.
(Continued)

*Primary Examiner* — Clinton A Brooks
(74) *Attorney, Agent, or Firm* — Baker & Hostetler LLP

(57) ABSTRACT

The present invention is directed to a mild, efficient, and general direct C(sp$^2$)-H bond silylation of terminal olefins. Various embodiments includes methods, each method comprising or consisting essentially of contacting at least one organic substrate comprising a terminal olefinic C—H bond, with a mixture of at least one organosilane, organosilane, or mixture thereof and an alkali metal alkoxide or alkali metal hydroxide, such that the contacting results in the formation of a silylated olefinic product. The systems associated with these methods are also disclosed.

23 Claims, 8 Drawing Sheets

(56) References Cited

OTHER PUBLICATIONS

Kim et al., "Regio- and Stereoselective Enyne Cross Metathesis of Silylated Internal Alkynes", Journal of The American Chemical Society, 2004, 126(33), 10242-10243.
Koumaglo et al., "Regioselection in the Alkylation of Trimethylsilylallyl Anion—Stereselective Synthesis of Disubstituted Alkenes", Tetrahedron Letters, 1984, 25, 717-720.
Lu et al., "Iridium-Catalyzed (Z)-Trialkysilyation of Terminal Olefins", Journal of Organic Chemistry, Feb. 8, 2010, 75, 1701-1705.
McAtee et al., "Preparation of Allyl and Vinyl Silanes by the Palladium-Catalyzed Silylation of Terminal Olefins: A Silyl-Heck Reaction", Angewandte Chemie International Edition, Apr. 10, 2012, vol. 51, 3663-3667.
McLaughlin et al., "MIDA—Vinylsilanes: Selective Cross-Couplings and Applications to the Synthesis of Functionalized Stilbenes",Organic Letters, 2015, 17, 10-13.
Miura et al., "Acid-catalyzed cyclization of vinylsilanes bearing a hydroxyl group. Benzyldimethylsilyl group as an effective promoter and novel hydroxyl surrogate", Tetrahedron Letters, Jan. 2000, 41, 2129-2132.
Naumov et al., "Selective Dehydrogenative Silyation Hydrogenation Reaction of Divinyldisiloxane with Hydrosilane Catalyzed by an Iron Complex", Journal of The American Chemical Society, Dec. 29, 2011, 134, 804-807.
Ochiai et al., "Reactions of Vinylsilanes With lewis Acid-Activated Iodosylbenzene: Stereospecific Synthesis of Vinyliodonium Tetrafluoroborates and Their Reactions as Highly Activated Vinyl Halides", Tetrahedron, 1988, 44, 13, 4095-4112.
Suzuki et al., "Enantiocontrolled Synthesis of Jasmonates via Tandem Retro-Diels-Alder-Ene Reaction Activated by a Silyl Substituent",Organic Letters, 2004, 6, 409-411.
Trost et al., "Regioselective Hydrosilylation of Propargylic Alcohols: An Aldol Surrogate",Angewandte Chemie International Edition, 2003, 42, 3415-3418.
Trost et al., "Ruthenium-Catalyzed Vinylsilane Synthesis and Cross-Coupling as a Selective Approach to Alkenes: Benzyldimethylsilyl as a Robust Vinylmetal Functionality",Organic Letters, 2003, 5(11), 1895-1898.

BASE-CATALYZED SILYLATION OF TERMINAL OLEFINIC C—H BONDS

CROSS REFERENCE TO RELATED APPLICATIONS

This application claims the benefit of priority to U.S. Patent Application Ser. No. 62/168,120, filed May 29, 2015, the contents of which are incorporated by reference herein for all purposes.

GOVERNMENT RIGHTS

This invention was made with government support under Grant No. CHE1212767 awarded by the National Science Foundation. The government has certain rights in the invention.

TECHNICAL FIELD

The present invention is directed at methods for silylating terminal olefinic substrates—i.e., containing terminal alkene C(sp2)-H bonds—using alkali metal hydroxide, alkoxide, or hydride catalysts and organosilane/organodisilane reagents.

BACKGROUND

The ability to silylate organic moieties has attracted significant attention in recent years, owing to the utility of the silylated materials in their own rights and as intermediates for other important materials used, for example, in agrichemical, pharmaceutical, and electronic material applications.

Over the past several decades, considerable effort has been allocated to the development of powerful catalyst architectures to accomplish a variety of C—H functionalization reactions, revolutionizing the logic of chemical synthesis and consequently streamlining synthetic chemistry. Accomplishing such challenging transformations can often necessitate the use of stoichiometric additives, demanding reaction conditions, complex ligands, and most notably precious metal catalysts. The need to use precious metal catalysts for these transformations remains a fundamental and longstanding limitation.

Strategies for the synthesis of vinylsilanes and allylsilanes have employed strong bases or have relied on stoichiometric or catalytic transition metal species such as Au, Co, Cr, Cu, Ir, Fe, Os, Ni, Pd, Pt, Rh, Ru, Ti, and Zn, typically using various alkyne starting materials (i.e., hydrosilylation reactions) and/or halogenated silylating reagents. These factors have led to important limitations in scope and practical utility. For example, in certain applications such as electronics, the presence of residual metals can adversely affect performance. In pharmaceuticals, the presence of residual metals is strictly regulated. The development of a mild and general stoichiometric or catalytic method for cross-dehydrogenative C(sp2)-Si bond formation from C—H bonds remains a longstanding challenge in the field.

The present invention takes advantage of the discoveries cited herein to avoid at least some of the problems associated with previously known methods.

SUMMARY

Herein is disclosed a mild, efficient, and generally direct non-aromatic C(sp2)-H bond silylation. The catalytic cross-dehydrogenative method avoids the limitations of previous strategies and successfully couples terminal olefins and organosilanes or organodisilanes previously unprecedented in C—H silylation. Remarkably, the catalysts can include a variety of strong bases, including alkali metal alkoxides or hydroxides.

Various embodiments includes methods comprising or consisting essentially of contacting at least one organic substrate comprising a terminal olefin with:

(a) an organosilane, organodisilane, or mixture thereof; and (b) an alkali metal alkoxide, an alkali metal hydroxide, an alkaline earth metal alkoxide, and alkaline earth hydroxide, an alkali metal amide (such as a potassium bis(trimethylsilyl) amide, KHMDS), or a mixture thereof; such that the contacting results in the formation of a terminally silylated olefinic product or a terminally hydrosilylated product, the latter apparently favored when using vinyl aromatic substrates.

In the methods, organosilane include those having a structure of Formula (I) and the organodisilane include those having a structure of Formula (II):

where m is independently 0, 1, or 2; and each R is broadly defined herein. The organosilane and organodisilane may be monomeric, oligomeric, or polymeric, or tethered to insoluble or sparingly soluble support media. Representative examples of organosilanes used in the methods include compounds of the general formula $(R)_3SiH$, $(R)_2SiH_2$, or $(R)SiH_3$, for example $Me_3SiH$, $EtMe_2SiH$, $Et_2MeSiH$, $Et_3SiH$, $(iPr)_3SiH$, $Bu_3SiH$, $PhMe_2SiH$, $Ph_2MeSiH$, $(EtO)_3SiH$, $Me_2(Py)SiH$, $(i-Pr)_2(Py)SiH$, $Me_2SiH_2$, $Et_2SiH_2$, $(i-Pr)_2 SiH_2$, $(Bu)_2SiH_2$, $Ph_2SiH_2$, or $Bn_2SiH_2$. Representative organodisilanes include those represented by the formulae $(R)_{3-m}(H)_mSi$—$Si(R)_{3-m}(H)_m$ or $(R)_3Si$—$Si(R)_3$, for example $(Me)_3Si$—$Si(Me)_3$. In these silanes and disilanes, R may be optionally substituted $C_{1-6}$ alkoxy, optionally substituted $C_{1-6}$ alkyl, optionally substituted $C_{2-6}$ alkenyl, optionally substituted phenyl, optionally substituted biphenyl, optionally substituted phenoxy, optionally substituted tolyl, optionally substituted phenethyl, optionally substituted benzyloxy, optionally substituted pyridinyl, optionally substituted pyridinylmethylether (Py-$CH_2$—), or optionally substituted pyridinylmethyl (Py-$CH_2$—O—). Convenient embodiments of the organosilanes or organodisilanes include those where R is independently at each occurrence optionally substituted methyl, ethyl, propyl, butyl, propyl, phenyl, biphenyl, phenoxy, benzyl, benzyloxy, or pyridinyl. In certain of these embodiments, R is unsubstituted.

In some embodiments, any of the bases may be applied individually or in combination with any one or more bases. In certain embodiments, the bases may comprise sodium hydroxide (NaOH), potassium hydroxide (KOH), a sodium alkoxide, potassium alkoxide, or any mixture thereof.

In some embodiments, the at least one organic substrate comprising the terminal olefin has a formula (III):

where p is 0 or 1 and $R^1$ and $R^2$ independently comprises H, an optionally substituted $C_{1-18}$ alkyl, optionally substituted $C_{2-18}$ alkenyl, $C_{2-18}$ optionally substituted alkynyl, optionally substituted $C_{6-18}$ aryl, optionally substituted $C_{1-18}$ heteroalkyl, optionally substituted 5-6 ring membered heteroaryl, optionally substituted 5-6 ring membered aralkyl, optionally substituted 5-6 ring membered heteroaralkyl, or optionally substituted metallocene, provided that $R^1$ and $R^2$ are not both H.

For example, the corresponding terminally silylated olefinic product can be a compound of Formula (IV) or (V):

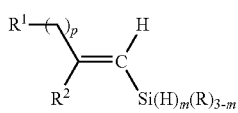
(IV)

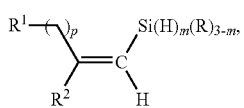
(V)

where p and R are defined elsewhere herein.

In other embodiments, wherein when p=1, the product can comprises a terminally silylated olefinic product is a compound of Formula (IV), (V), (VI), or (VII):

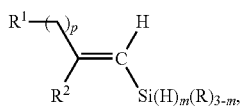
(IV)

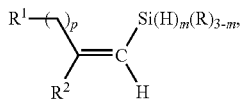
(V)

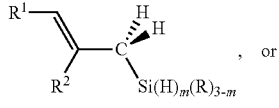
(VI)
, or

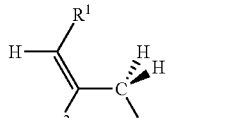
(VII)

When p is 0 and either $R^1$ or $R^2$ is aromatic, the reaction appears to proceed to form hydrosilylated products, for example resulting in the formation of a product of Formula (VIII) or (IX):

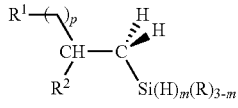
(IVIII)

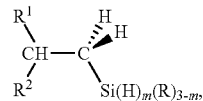
(IX)

resulting from the anti-Markovnikov addition of the organosilane to a vinyl aromatic substrate.

The disclosed methods may be conducted in the presence or absence of added transition metal ions or catalysts, though one of the attractive features of these disclosed reactions is the fact that transition metal ions or catalysts are not required for the operability of the methods. In certain independent embodiments, then, such transition metal ions or catalysts may be present as levels less than 1 wt %, 1000 ppm, 100 ppm, 50 ppm, or 10 ppm, or may be undetectably present, based on the total weight of the system.

Once formed, the products of the disclosed methods can be used as convenient precursors to a range of reactions, depending on the nature of the product. The scope of the present disclosure is intended to include these downstream reactions.

For example, if the product of the reaction comprises a Si—H bond, whether a terminally silylated olefinic product or a terminally silylated saturated product, that product may be conveniently used as a building block, either in situ or as an isolated product, for the silylation of aromatic (including aryl and heteroaryl) substrates or substrates comprising terminal alkynyl C—H bonds, for example as described in U.S. Pat. No. 9,000,167, U.S. patent application Ser. No. 14/818,417, filed Aug. 5, 2015, U.S. patent application Ser. No. 14/841,964, filed Sep. 1, 2015, and U.S. patent application Ser. No. 14/972,653, filed Dec. 17, 2015, each of which is incorporated by reference herein, at least for for their teachings of the nature and conditions of the silylation reactions, including the examples cited.

If the product of the reaction comprises a terminally silylated olefinic product, for example, a vinyl silane or allylic silane, the product may be conveniently used as a building block where such unsaturated silanes are known to be used, either in situ or as an isolated product. For example, such terminally silylated olefinic products may be polymerized by suitable methods, either by themselves or with other olefinic or acetylenic precursors. They may be used as synthons in Alder-ene type reactions or various coupling reactions.

In other embodiments, the terminally silylated olefinic product, may be reacted with (a) ICl or $I_2$ so as to form a terminal vinyl iodide; (b) a polyolefin (for example, polyethylene) so as to form a silane grafted polyolefin; (c) an organic peroxide (for example m-CPBA) to form a terminal silylated peroxide, which when treated with a strong acid (e.g., perchloric acid, formic acid, or TFA) forms an aldehyde moiety; (d) a fluoride source, hydrogen peroxide, and base to form an aldehyde, according to the well-known Tamao-Fleming Oxidation reaction; or (e) an iodosyl benzene to form a vinyliodonium tetrafluoroborate, in each case under conditions known to effect the designated transformations.

In addition to the methods for effecting the silylation of terminal olefins, the disclosure also contemplates any and all compositions associated with these transformations. For example, some embodiments provide compositions which may comprise a mixture of:

(a) an organic substrate comprising a terminal olefin:
(b) an organosilane, an organodisilane, or a mixture thereof; and
(c) an alkali metal alkoxide, an alkali metal hydroxide, or a mixture thereof; wherein the nature of the substrates, organosilanes and organodisilanes, and base materials are the same or equivalent as described for the methods.

In other embodiments, these compositions may further comprise one or more of the products of the methods, such as described herein, for example as a compound of Formula (III), (IV), (V), (VI), (VII), (VIII), or (IX)

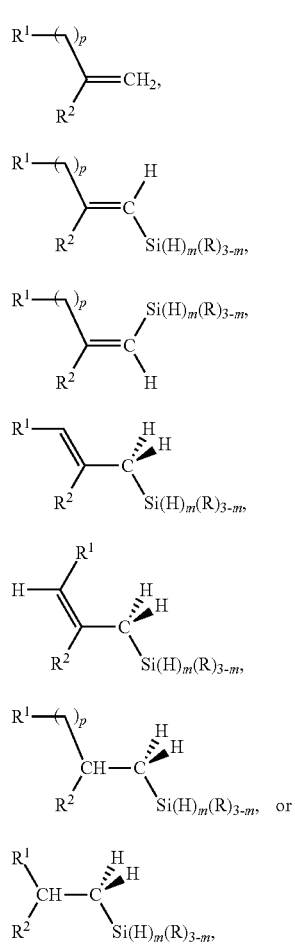

wherein $R^1$, $R^2$, m, and p may be any species or combination of species described herein.

In still other embodiments, the composition contains no added transition metal ions or transition metal catalysts otherwise capable of effecting the silylation of terminal olefins in a reaction where the reaction product is a terminally silylated olefinic product, or may be described as substantially free of transition metal ions or transition metal catalysts otherwise capable of effecting the silylation of terminal olefins in a reaction where the reaction product is a terminally silylated olefinic product or where the reaction product is a terminally hydrosilylated product.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific methods, devices, and systems disclosed. In addition, the drawings are not necessarily drawn to scale. In the drawings.

DETAILED DESCRIPTION OF ILLUSTRATIVE EMBODIMENTS

Figure 1A:
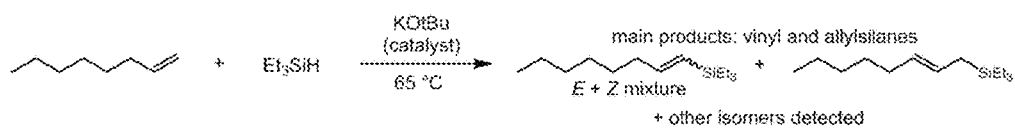
FIG. 1A illustrates an exemplary reaction, showing the remarkable selectivity of silylation of 1-octene to provide a terminally silylated olefinic product.
Figure 1B:
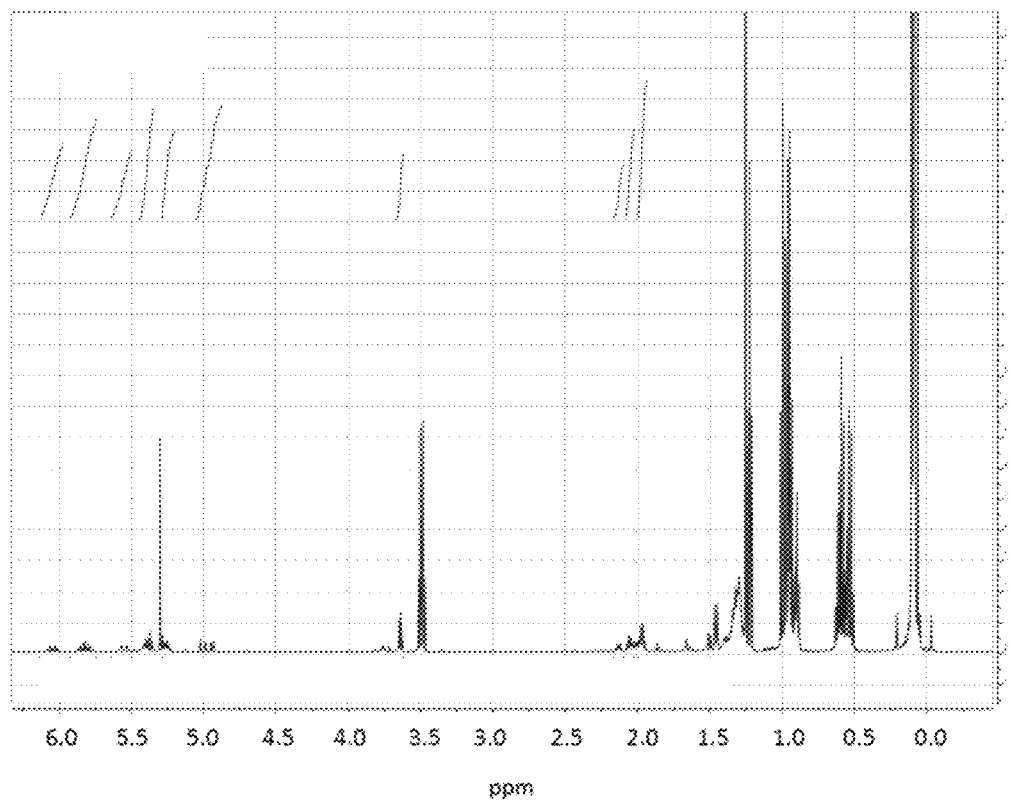
FIG. 1B shows an $^1$H NMR spectrum of the reaction of FIG. 1A before purification (ie. crude material).
Figure 1C:
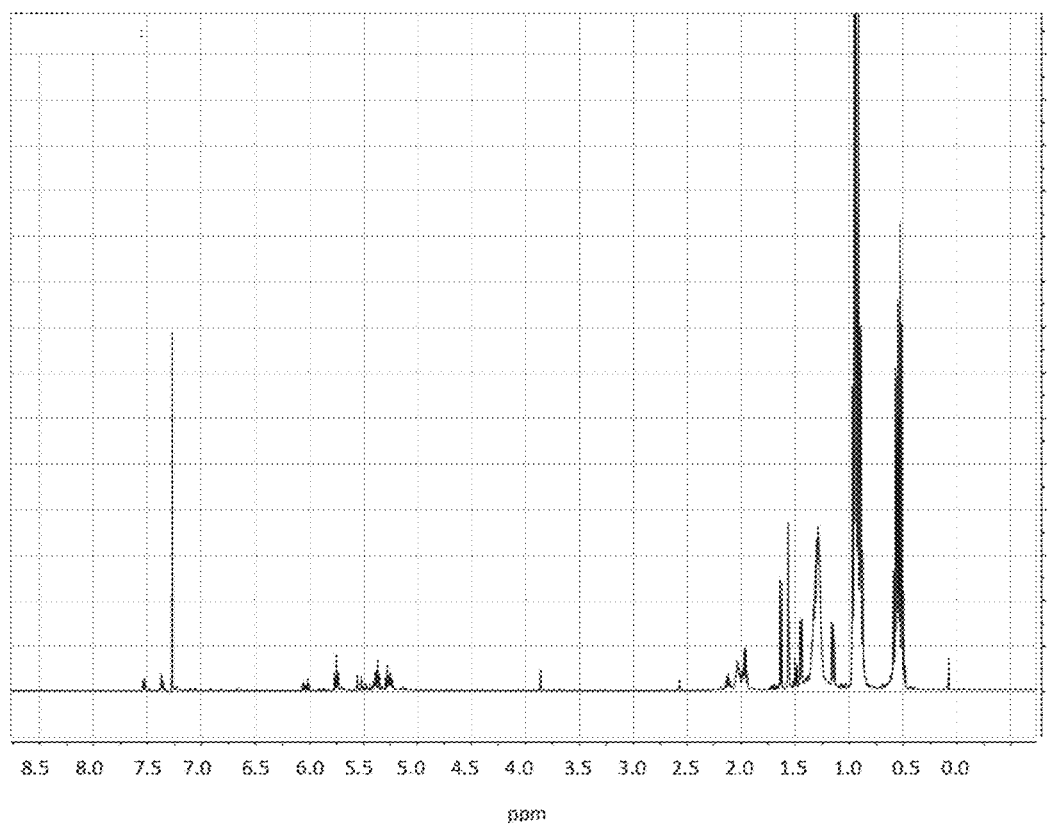
FIG. 1C shows an $^1$H NMR spectrum of the product of the reaction of FIG. 1A, but at 85° C. before purification (ie. crude material), but after high vacuum.
Figure 1D:
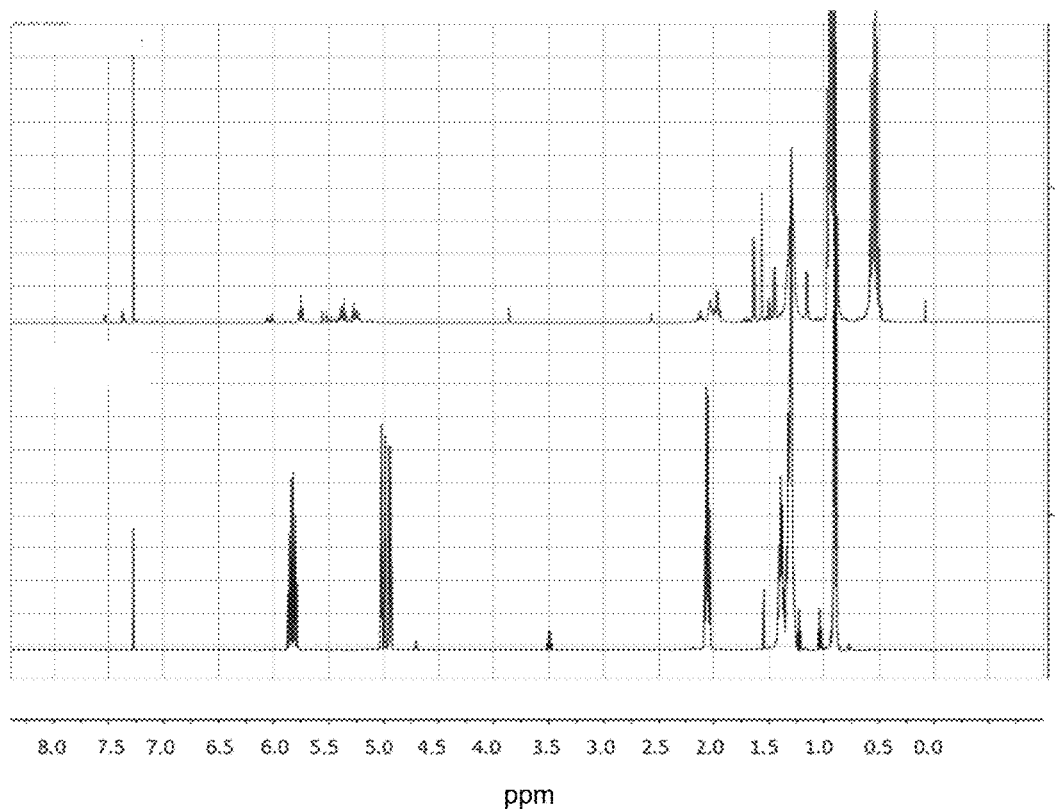
FIG. 1D shows the comparative $^1$H NMR spectra of the above reaction at 85° C. before purification (ie. crude material), but after high vacuum (upper spectrum) and the starting material 1-octene (lower spectrum)

The present invention is founded on a set of reactions, each of which relies on simple mixtures of organosilanes and organosilanes and strong bases, including alkali metal hydroxide, alkoxides, hydrides, and anionic amide bases, which together form in situ systems (the structure and nature of the active species is still unknown) able to silylate terminal olefins, and when contacted with such substrates, silylates them. Such transformations proceed without the required presence of transition metal catalysts, UV radiation or electrical (including plasma) discharges. These reactions are relevant as an important advance in developing practical methods for the preparation of products important for agrochemical, electronics, fine chemicals, and pharmaceutical applications. Importantly this reaction is of great interest since it produces only environmentally benign silicates as the byproduct and can avoid metal waste streams as would be observed with nearly all other approaches proposed in the literature towards this end. The remarkable facility exhibited by these systems provides a useful tool in the kit of chemists in these fields. This utility can be leveraged when combined with other follow-on reactions.

The present invention may be understood more readily by reference to the following description taken in connection with the accompanying Figures and Examples, all of which form a part of this disclosure. It is to be understood that this invention is not limited to the specific products, methods, conditions or parameters described or shown herein, and that the terminology used herein is for the purpose of describing particular embodiments by way of example only and is not intended to be limiting of any claimed invention. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this text, it is recognized that the descriptions refer to both the compositions and methods of making and using said compositions. That is, where the disclosure describes or claims a feature or embodiment associated with a composition or a method of making or using a composition, it is appreciated that such a description or claim is intended to extend these features or embodiment to embodiments in each of these contexts (i.e., compositions, methods of making, and methods of using).

Methods of Silylating Terminal Olefins

The present invention includes embodiments related to chemical systems and methods for silylating terminal olefins. Specific embodiments provide methods, each method comprising contacting at least one organic substrate comprising a terminal olefinic C—H bond, with at least one organosilane or organodisilane, or mixture thereof and a strong base, such as an alkali metal alkoxide, an alkali metal hydroxide, an alkaline earth metal alkoxide, and alkaline earth hydroxide, an alkali metal amide (such as a potassium bis(trimethylsilyl) amide, KHMDS), or a mixture thereof, under conditions sufficient to form a silylated terminal olefin, such that the contacting results in the formation of either or both of a terminally silylated olefinic product or a terminally hydrosilylated product. The balance of the terminally silylated olefinic product or a terminally hydrosilylated product is at least influenced by the nature of the precursor olefin. In some embodiments, the product of the reaction is one or more terminally silylated olefinic products and is substantially devoid of hydrosylation products. This aspect of the disclosure is elaborated further herein. Under certain identified conditions, the reactions also provide regioselective hydrosilylated products, which in their own right are useful transformations as well.

The methods operate well in the absence of added transition metal catalysts which are normally necessary to effect silylation reactions, as well as in the complete absence of (or substantially complete absence) of transition-metal ions or catalysts which have previously been used to catalyzed similar reactions. In certain embodiments, the methods can be conducted in the substantial absence of transition metal ions or catalysts. In other embodiments, the methods may be conducted with less than 1 wt %, 1000 ppm, 100 ppm, 50 ppm, or 10 ppm, based on the total weight of the system. Likewise, these methods are also operable in the absence or substantially complete absence of other electromagnetic or thermal triggers needed for initiation or propagation. That is, these embodiments do not need or use UV irradiation or electric or plasma discharge conditions to operate.

The organosilane may be described, in some embodiments, as including those having a structure of Formula (I); and the organodisilane may be described, in some embodiments, as including those having a structure of Formula (II):

$$(R)_{3-m}Si(H)_{m+1} \tag{I}$$

$$(R)_{3-m}(H)_mSi\text{—}Si(R)_{3-m}(H)_m \tag{II}$$

where: m is independently 0, 1, or 2; and each R is independently optionally substituted $C_{1-24}$ alkyl or heteroalkyl, optionally substituted $C_{2-24}$ alkenyl or heteroalkenyl, optionally substituted $C_{2-24}$ alkynyl or heteroalkynyl, optionally substituted 6 to 18 ring membered aryl or 5 to 18 ring membered heteroaryl, optionally substituted 6 to 18 ring-membered alkaryl or 5 to 18 ring-membered heteroalkaryl, optionally substituted 6 to 18 ring-membered aralkyl or 5 to 18 ring-membered heteroaralkyl, optionally substituted —O—$C_{1-24}$ alkyl or heteroalkyl, optionally substituted 6 to 18 ring-membered aryloxy or 5 to 18 ring-membered heteroaryloxy, optionally substituted 6 to 18 ring-membered alkaryloxy or 5 to 18 ring-membered heteroalkaryloxy, or optionally substituted 6 to 18 ring-membered aralkoxy or 5 to 18 ring-membered heteroaralkoxy, and, if substituted, the substituents may be phosphonato, phosphoryl, phosphanyl, phosphino, sulfonato, $C_1$-$C_{20}$ alkylsulfanyl, $C_5$-$C_{20}$ arylsulfanyl, $C_1$-$C_{20}$ alkylsulfonyl, $C_5$-$C_{20}$ arylsulfonyl, $C_1$-$C_{20}$ alkylsulfinyl, 5 to 12 ring-membered arylsulfinyl, sulfonamido, amino, amido, imino, nitro, nitroso, hydroxyl, $C_1$-$C_{20}$ alkoxy, $C_5$-$C_{20}$ aryloxy, $C_2$-$C_{20}$ alkoxycarbonyl, $C_5$-$C_{20}$ aryloxycarbonyl, carboxyl, carboxylato, mercapto, formyl, $C_1$-$C_{20}$ thioester, cyano, cyanato, thiocyanato, isocyanate, thioisocyanate, carbamoyl, epoxy, styrenyl, silyl, silyloxy, silanyl, siloxazanyl, boronato, boryl, or halogen, or a metal-containing or metalloid-containing group, where the metalloid is Sn or Ge, where the substituents may optionally provide a tether to an insoluble or sparingly soluble support media comprising alumina, silica, or carbon.

Each combination of m and R is considered a separate embodiments; in particular, where independently, m is 0, m is 1, and m is 2. Likewise, the individual use of organosilane and organodisilane are considered separate embodiments.

Within the scope of the disclosure, there are few limits placed on the nature of the organosilane and organodisilane silylating agents. These may be individual discrete compounds, may be part of oligomeric or polymeric structures, or may be tethered to insoluble or sparingly soluble support media for ease of work-up. That said, the organosilanes used in the present work are conveniently presented as soluble or at least simple compounds, of the general formulae $(R)_3SiH$, $(R)_2SiH_2$, or $(R)SiH_3$. In some embodiments, where R is independently at each occurrence optionally substituted $C_{1-18}$ alkoxy, optionally substituted $C_{1-18}$ alkyl, optionally substituted $C_{2-18}$ alkenyl, optionally substituted 6-18 ring membered aryl (i.e., containing 6-18 atoms in the ring system), 6-18 ring membered aryloxy, 5-18 ring membered heteroaryl, 6-18 ring membered aralkyl, 6-18 ring membered aralkyloxy, or 6-10 ring membered heteroaralkyl. In certain aspects, R is independently at each occurrence optionally substituted $C_{1-6}$ alkoxy (e.g., methoxy, ethoxy, propoxy, butoxy, etc.), optionally substituted $C_{1-6}$ alkyl (e.g., methyl, ethyl, propyl, butyl, etc.), optionally substituted $C_{2-6}$ alkenyl, optionally substituted optionally substituted phenyl, optionally substituted biphenyl, optionally substituted phenoxy, optionally substituted tolyl, optionally substituted benzyl (Bn), optionally substituted phenethyl, optionally substituted benzyloxy, optionally substituted pyridinyl (Py), optionally substituted pyridinylmethyl (Py-CH$_2$—), or optionally substituted pyridinylmethyl (Py-CH$_2$—O—). In certain embodiments, the organosilane is Me$_3$SiH, EtMe$_2$SiH, Et$_2$MeSiH, Et$_3$SiH, (iPr)$_3$SiH, Bu$_3$SiH, PhMe$_2$SiH, Ph$_2$MeSiH, (EtO)$_3$SiH, Me$_2$(Py)SiH, (i-Pr)$_2$(Py)SiH, Me$_2$SiH$_2$, Et$_2$SiH$_2$, (i-Pr)$_2$SiH$_2$, (Bu)$_2$SiH$_2$, Ph$_2$SiH$_2$, or Bn$_2$SiH$_2$. Any of the organosilanes used in the Examples are also specific embodiments of useful silylating reagents.

In certain embodiments, $(R)_3SiH$ include the use of alkyl, aryl, heteraryl, alkoxy, or mixed alkyl-aryl silanes or alkyl-heteroaryl silanes, for example, EtMe$_2$SiH, (n-Bu)$_3$SiH, Et$_2$SiH$_2$, PhMe$_2$SiH, BnMe$_2$SiH, (EtO)$_3$SiH, (i-Pr)$_3$SiH, Me$_2$(pyridinyl)SiH, or (i-Pr)$_2$(pyridinyl)SiH, or Me$_3$Si—SiMe$_2$H. Polymeric materials, such as polymethylhydrosiloxane (PMHS), are also believed to be effective.

The organodisilanes used in the present work are conveniently presented as soluble, or at least simple, compounds of the general formulae (R)$_{3-m}$(H)$_m$Si—Si(R)$_{3-m}$(H)$_m$ or (R)$_3$Si—Si(R)$_3$. In some of these embodiments, R is independently at each occurrence optionally substituted C$_{1-18}$ alkoxy, optionally substituted C$_{1-18}$ alkyl, optionally substituted C$_{2-18}$ alkenyl, optionally substituted C$_{6-18}$ aryl, optionally substituted C$_{6-18}$ aryloxy, optionally substituted 5-18 ring membered heteroaryl, optionally substituted 6-18 ring membered aralkyl, optionally substituted 6-18 ring membered aralkyloxy, or optionally substituted 6-18 ring membered heteroaralkyl. In certain embodiments, R is independently at each occurrence optionally substituted C$_{1-6}$ alkoxy, optionally substituted C$_{1-6}$ alkyl, optionally substituted C$_{2-6}$ alkenyl, optionally substituted optionally substituted phenyl, optionally substituted biphenyl, optionally substituted phenoxy, optionally substituted tolyl, optionally substituted phenethyl, optionally substituted benzyloxy, optionally substituted pyridinyl, optionally substituted pyridinylmethyl (Py-CH$_2$—), or optionally substituted pyridinylmethyl (Py-CH$_2$—O—).

The strong bases useful for the present methods include alkali metal alkoxides, alkali metal hydroxides, alkaline earth metal alkoxides, alkaline earth hydroxides, alkali metal amides (such as a potassium bis(trimethylsilyl) amide, KHMDS), or a mixture thereof. Some representative examples of the relative reactivities of these types of bases are provided in the Examples. As shown there, useful alkali metal hydroxides include those comprising sodium hydroxide (NaOH), potassium hydroxide (KOH), or mixtures thereof. Similarly, useful alkali metal alkoxides include sodium alkoxides, potassium alkoxides, or mixture thereof. Mixtures of hydroxides and alkoxides are also contemplated by the present disclosure.

As used herein, the term "alkoxide" carries its conventional meaning, as the conjugate base of an organic alcohol. Useful alkoxides include those comprising a C$_{1-12}$ linear or branched alkyl moiety or a C$_{5-10}$ aromatic or C$_{4-10}$ heteroaromatic moiety, for examples methoxide, ethoxide, propoxide, tert-butoxide, 2-ethyl-hexyloxide, or benzyloxide.

Useful alkoxides include sodium methoxide, sodium ethoxide, sodium n-propoxide, sodium isopropoxide, sodium n-butoxide, sodium sec-butoxide, sodium tert-butoxide, sodium n-pentoxide, sodium 2-pentoxide, sodium 3-pentoxide, sodium iso-pentoxide, potassium methoxide, potassium ethoxide, potassium n-propoxide, potassium isopropoxide, potassium n-butoxide, potassium sec-butoxide, potassium tert-butoxide, potassium n-pentoxide, potassium 2-pentoxide, potassium 3-pentoxide, potassium iso-pentoxide, or sodium or potassium 2-ethyl-hexyloxide. The alkoxides may also comprise a C$_{5-10}$ aromatic or C$_{4-10}$ heteroaromatic moiety, for example, or benzyloxide.

Further, the choice of the counter cation also impacts the effectiveness of the activity of the chemical system. Whereas a wide range of counterions have been shown to work, the use of potassium alkoxides and/or hydroxides appears preferred. More specifically, potassium methoxide, ethoxide, and tert-butoxide are shown to provide convenient kinetics. As in other silylation reactions that appear related to this platform, the potassium counter ion appears to play a critical, albeit unknown, role in the generation of the active silylating species. As such, in the present context, a description of potassium alkoxide, or any specific potassium alkoxide, should be interpreted as the named chemical entity added as such, or the result of the addition of separate alkoxide potassium cation sources, such that the potassium alkoxide is or may be seen as generated in situ. Interestingly, the presence of excess potassium cation appears to provide little additional benefit to its stoichiometric presence (see, e.g., Table 7)

While the relative amounts of silylating agent and the strong base is not believed to be particularly important, so long as both are present in sufficient quantities, in certain embodiments, the organodisilane and the at least alkoxide base are present together at a molar ratio, with respect to one another, in a range of from about 20:1 to about 1:1. In other embodiments, these ratios may be on the order of about 5:1 to about 1:1, from about 3:1 to about 1:1, or from about 3:2 to about 1:1. The silylation reactions appear also to favor those conditions where the base is sub-stoichiometric, 0.01:1 to 0.9:1, with respect to the substrate, especially for more active systems. Further embodiments provide that the base is present with respect to the substrate at a ratio of from about 0.01:1 to about 0.6, or from about 0.1:1 to about 0.6:1.

The Examples provide exemplary reaction conditions useful for effecting the desired transformations. In some embodiments, the conditions sufficient to silylate the organic substrate comprise heating the substrate with a mixture of (a) at least one organosilane, organodisilane, or mixture thereof and (b) at least one strong base, such as the alkali metal alkoxide, alkali metal hydroxide, alkaline earth metal alkoxide, alkaline earth hydroxide, alkali metal amide (such as a potassium bis(trimethylsilyl) amide, KHMDS), or mixture thereof, at a temperature in a range of about 10° C. to about 165° C. In some cases, the temperatures may be applied in a range of from about 20° C., about 30° C., about 40° C., about 50° C., or about 60° C., to about 125° C., about 100° C., or to about about 80° C. Any of the temperatures described in the Examples may be considered independent embodiments. Typical operating reaction times may range from about 2 hours, from about 4 hours, from about 6 hours, or from about 10 hours to about 28 days, to about 14 days, to about 7 days, to about 4 days, to about 3 days, to about 48 hours, to about 24 hours, to about 12 hours, or to about 6 hours.

These methods typically employ hydrocarbon or ether-based solvents. Ether solvents, such as tetrahydrofurans (including 2-methyltetrahydrofuran), diethyl and dimethyl ether, methyl-t-butyl ether, 1,2-dimethoxyethane, and alkyl terminated glycols have been shown to work well. Ester, amide, and ketone solvents may also be used, but these do not work as well as the ethers. Polar aprotic solvents including HMPA are also believed to be acceptable.

The methods are fairly flexible with respect to substrates. In some embodiments, the substrates may include compounds of Formula (III):

where p is 0 or 1; R$^1$ and R$^2$ independently comprises H, an optionally substituted C$_{1-18}$ alkyl, optionally substituted C$_{2-18}$ alkenyl, optionally substituted C$_{2-18}$ alkynyl, optionally substituted C$_{6-18}$ aryl, optionally substituted C$_{1-18}$ heteroalkyl, optionally substituted 5-6 ring membered heteroaryl, optionally substituted 5-6 ring membered aralkyl, optionally substituted 5-6 ring membered heteroaralkyl, or optionally substituted metallocene, provided that $R^1$ and $R^2$ are not both H.

Within this context, independent embodiments include those wherein each $R^1$ and $R^2$ independently is or comprises:

(a) an optionally substituted $C_{1-18}$ linear alkyl, an optionally substituted branched $C_{1-18}$ alkyl, or an optionally substituted $C_{3-18}$ cycloalkyl;

(b) an optionally substituted linear $C_{2-18}$ alkenyl, an optionally substituted branched $C_{2-18}$ alkenyl, or an optionally substituted $C_{3-18}$ cycloalkenyl;

(c) an optionally substituted linear $C_{1-18}$ heteroalkyl, an optionally substituted branched $C_{1-18}$ heteroalkyl, or an optionally substituted $C_{1-18}$ heterocycloalkyl;

(d) an optionally substituted 6-18 ring membered aryl, an optionally substituted 6-18 ring membered aralkyl, an optionally substituted 6-18 ring membered aryloxy, an optionally substituted 6-18 ring membered aralkyloxy, optionally substituted 5-18 ring membered heteroaryl, or an optionally substituted optionally substituted 5-18 ring membered heteroaralkyl, optionally substituted 5-18 ring membered heteroaryloxy, or an optionally substituted optionally substituted 5-18 ring membered heteroaralkyloxy; or (e) hydrogen, provided that $R^1$ and $R^2$ are not both hydrogen when p=0.

In more specific embodiments, each $R^1$ and $R^2$ independently is or comprises:

(a) an optionally substituted $C_{3-18}$ alkyl;
(b) an optionally substituted benzene, biphenyl, naphthalene, or anthracene ring structure; or
(c) an optionally substituted furan, pyrrole, thiophene, pyrazole, imidazole, triazole, isoxazole, oxazole, thiazole, isothiazole, oxadiazole, pyridine, pyridazine, pyrimidine, pyrazine, triazone, benzofuran, benzopyrrole, benzothiophene, isobenzofuran, isobenzopyrrole, isobenzothiophene, indole, isoindole, indolizine, indazole, azaindole, benzisoxazole, benzoxazole, quinoline, isoquinoline, cinnoline, quinazoline, naphthyridine, 2,3-dihydrobenzofuran, 2,3-dihydrobenzopyrrole, 2,3-dihydrobenzothiophene, dibenzofuran, xanthene, dibenzopyrol, or dibenzothiophene moiety.

In certain aspects within these embodiment, the optionally substituted aromatic moiety comprises optionally substituted phenyl, biphenyl, phenoxy, benzyl, benzyloxy, naphthyl, or naphthyloxy. In certain other aspects, the optionally substituted aromatic moiety comprises an optionally substituted furan, pyrrole, thiophene, pyrazole, imidazole, triazole, isoxazole, oxazole, thiazole, isothiazole, oxadiazole, pyridine, pyridazine, pyrimidine, pyrazine, triazone, benzofuran, benzopyrrole, benzothiophene, isobenzofuran, isobenzopyrrole, isobenzothiophene, indole, isoindole, indolizine, indazole, azaindole, benzisoxazole, benzoxazole, quinoline, isoquinoline, cinnoline, quinazoline, naphthyridine, 2,3-dihydrobenzofuran, 2,3-dihydrobenzopyrrole, 2,3-dihydrobenzothiophene, dibenzofuran, xanthene, dibenzopyrrole, or dibenzothiophene moiety.

In specific embodiments within these options, $R^2$ is H.

In specific embodiments within these options, p is 0 or 1, $R^1$ is an optionally substituted $C_{1-18}$ alkyl, and $R^2$ is H. Examples of such compounds include those comprising optionally substituted propenyl, 1-butenyl, 1-pentenyl, 1-hexenyl, 1-heptenyl, 1-octenyl, 1-nonenyl, 1-decenyl, 1-undecenyl, 1-dodecenyl, 1-tridecenyl, 1-tetradecenyl, 1-pentadecenyl, 1-hexadecenyl, 1-heptadecenyl, 1-octadecenyl, etc. moieties.

In specific embodiments within these options, the terminal olefins include ethylene, propene, 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, etc.

The optionally substituted $C_{1-18}$ alkyl may be described as being a directing substrate—i.e., having functional groups such as hydroxide, ketones, amides, carboxy esters, and/or fluorine pendants or groups sufficiently close to the terminal double bond to effect the olefin position in the final product. In some cases, the optionally substituted $C_{1-18}$ alkyl may be described non-directing substrate, for example where the alkyl group contains only hydrogen atoms proximate (e.g., within 3-6 carbon atoms) to the terminal double bond.

In other specific embodiments within these options, p is 0, $R^1$ is an optionally substituted aromatic moiety, including an aryl or heteroaryl moiety, and $R^2$ is H In other specific embodiments within these options, p is 0, $R^1$ is an unsaturated group conjugated to the terminal >C=CH$_2$ moiety, and $R^2$ is H.

The nature of the final silylation reaction appears to depend on the nature of the organic substrate comprising the terminal olefinic C—H bond For example, in some embodiments, the reaction produces at least one terminally silylated olefinic product that is a vinyl silane having a Formula (IV) or (V):

(IV)

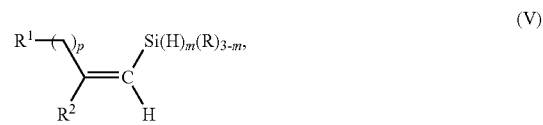

(V)

where $R^1$, $R^2$, p, and m are defined elsewhere herein. That is, the products may be one or more vinyl silanes, configured in an E- or Z-configuration. In some cases, the E-configuration appears to be slightly preferred. In others, the Z-configuration appears to be slightly preferred. In other embodiments, the reaction produces at least one terminally silylated olefinic product that comprises an allylic silanes having a Formula (VI) or (VII):

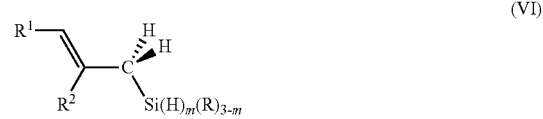

(VI)

(VII)

where $R^1$, $R^2$, p, and m are defined elsewhere herein. That is, the products may be one or more allylic silanes. These allylic silanes have tended to be present in mixtures with the corresponding vinyl silane products, at least in the presence of undirected terminal olefins. It is expected that the presence of directing groups such as hydroxide, carbonyls, heteroatoms, and halogen atoms (e.g., fluorine), positioned proximate to the terminal olefins bonds in the substrate will effect the relative amounts of such isomers produced.

It should be appreciated that in those cases, where the silylating reagent is an organodisilane having at least one Si—H bond, that the product of the reaction may comprise a corresponding structure in which the silyl group, —Si(H)$_m$(R)$_{3-m}$ in any of the preceding structures is replaced by a corresponding —Si(H)$_m$(R)$_{2-m}$—Si(H)$_m$(R)$_{3-m}$ disilyl group. It should also be appreciated that in those cases where m is not 0 (i.e., where the silylated product comprises a Si—H bond), that it is possible, by adjusting conditions within the reaction mixture (e.g., stoichiometries, order of addition of reagents, or like variables) to prepare so-called "tethered" compounds, where an initially formed product reacts with another available molecule of starting material to form a product containing a bridging —Si(R)$_2$-linkage; e.g., see example of 1-vinylnaphthalene provided in Table 8.

Certain experiments are also interpretable in a context where an initially formed vinyl silane or allylic silane undergoes further reactions, under appropriate conditions, such that the first formed product is further hydrosilylated to form a disilyl product. Such products should not be seen as unexpected, and manipulation of the reaction conditions may drive the product to such products.

In other cases where the terminal olefin is conjugated, for example to an aromatic group (e.g., when p is 0 and either R$^1$ or R$^2$ is aromatic or conjugated to an aromatic moiety), the product of the reaction appears to favor formation of a terminally silylated compound of the Formulae (VIII) or (IX):

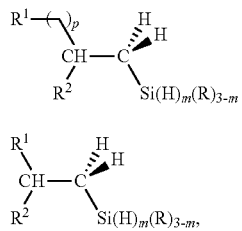

resulting from the anti-Markovnikov addition of the organosilane to a terminal olefin. Such reactions are most clearly seen in the Examples for the (hydro)silylation of vinyl aromatic substrates. In no case has Markovnikov addition of the organosilane to such an olefinic precursor been observed, offering the possibility of a transition-metal-free entry into such chemistries and products. Such specific regioselectivity is but one of the novel features described in this application Compositions The inventive concepts have been thus far described in terms of the methods of catalytically silylating terminal olefinic C(sp2)-H bonds. It should be appreciated that the products obtained from such methods, to the extent that they are not practically available by other means known at the time of this filing, and the systems used in these methods, are all considered within the scope of the present disclosure.

Again, the scope of the present disclosure includes embodiments for any system necessary to affect any of the methods described herein. For example, certain embodiments provide systems for silylating an organic substrate comprising a terminal olefinic C—H bond, each system comprising or consisting essentially of a mixture of (a) at least one organosilane or organodisilane and (b) an alkali metal hydroxide, alkoxide, or other bases described as operable herein, or a mixture thereof, and (c) at least one substrate. Such systems typically include the substrate(s) upon which the system is operable; i.e., the substrates comprising at least one terminal olefinic C(sp2)-H moiety. As disclosed else here herein, the system may contain or be substantially free of added transition-metal compounds, or where present, the transition metal may be considered a spectator to the reaction. Even in those cases where the transition metals are known to catalyze silylation reactions, at best they may provide a parallel competitive reaction pathway. In some embodiments, the system further comprises the presence of a silylated terminal olefin or saturated silane derived from the reaction between the substrate and the at least one organosilane.

The present disclosure, then, includes those compositions comprising a mixture of:
(a) an organic substrate comprising a terminal olefin:
(b) an organosilane, an organodisilane, or a mixture thereof and
(c) an alkali metal alkoxide, an alkali metal hydroxide, an alkaline earth metal alkoxide, and alkaline earth hydroxide, an alkali metal amide (such as a potassium bis(trimethylsilyl) amide, KHMDS), or a mixture thereof thereof. Any ingredient discussed in terms of the methods and described in the Examples as showing any activity in these methods is considered included in the parameters of these compositions as separate individual embodiments.

The composition may contain any one or both of the organosilanes or organoisilanes as described herein, including those of Formula (I) and Formula (II):

$$(R)_{3-m}Si(H)_{m+1} \qquad (I)$$

$$(R)_{3-m}(H)_mSi\text{—}Si(R)_{3-m}(H)_m \qquad (II)$$

where: m and R are as described by any of the descriptors provided elsewhere for these elements.

The composition may contain any hydroxide base of the general or specific description provided herein, including sodium hydroxide (NaOH), potassium hydroxide (KOH), sodium alkoxide, potassium alkoxide, or a mixture thereof.

The composition may contain any alkoxide base of the general or specific description otherwise provided herein, including those wherein the alkoxide comprises a linear, branched, or cyclic saturated hydrocarbon group containing 1 to 12 carbon atoms, for example sodium methoxide, sodium ethoxide, sodium n-propoxide, sodium isopropoxide, sodium n-butoxide, sodium sec-butoxide, sodium tert-butoxide, sodium n-pentoxide, sodium 2-pentoxide, sodium 3-pentoxide, sodium iso-pentoxide, potassium methoxide, potassium ethoxide, potassium n-propoxide, potassium iso-propoxide, potassium n-butoxide, potassium sec-butoxide, potassium tert-butoxide, potassium n-pentoxide, potassium 2-pentoxide, potassium 3-pentoxide, or potassium iso-pentoxide.

The composition may further contain any of the organic substrates comprising the terminal olefin described either generally or specifically. In certain of these embodiments, the composition comprises an organic substrate having a Formula (III):

where p, $R^1$, and $R^2$ reflect any description otherwise provided herein. In certain embodiments, $R^1$ and $R^2$ independently is or comprises:

(a) an optionally substituted $C_{1-18}$ linear alkyl, an optionally substituted branched $C_{1-18}$ alkyl, or an optionally substituted $C_{3-18}$ cycloalkyl;

(b) an optionally substituted linear $C_{2-18}$ alkenyl, an optionally substituted branched $C_{2-18}$ alkenyl, or an optionally substituted $C_{3-18}$ cycloalkenyl;

(c) an optionally substituted linear $C_{1-18}$ heteroalkyl, an optionally substituted branched $C_{1-18}$ heteroalkyl, or an optionally substituted $C_{1-18}$ heterocycloalkyl;

(d) an optionally substituted 6-18 ring membered aryl, an optionally substituted 6-18 ring membered aralkyl, an optionally substituted 6-18 ring membered aryloxy, an optionally substituted 6-18 ring membered aralkyloxy, optionally substituted 5-18 ring membered heteroaryl, or an optionally substituted optionally substituted 5-18 ring membered heteroaralkyl, optionally substituted 5-18 ring membered heteroaryloxy, or an optionally substituted optionally substituted 5-18 ring membered heteroaralkyloxy; or (e) hydrogen, provided that $R^1$ and $R^2$ are not both hydrogen when p=0.

In certain specific embodiments, the optionally substituted aryl, aryloxy, arylalkyl, or arylalkyloxy comprises optionally substituted phenyl, phenoxy, benzyl, benzyloxy, naphthyl, or naphthyloxy. In certain embodiments, the optionally substituted heteroaryl, heteroaryloxy, heteroarylalkyl, or heteroarylalkyloxy comprises an optionally substituted furan, pyrrole, thiophene, pyrazole, imidazole, triazole, isoxazole, oxazole, thiazole, isothiazole, oxadiazole, pyridine, pyridazine, pyrimidine, pyrazine, triazone, benzofuran, benzopyrrole, benzothiophene, isobenzofuran, isobenzopyrrole, isobenzothiophene, indole, isoindole, indolizine, indazole, azaindole, benzisoxazole, benzoxazole, quinoline, isoquinoline, cinnoline, quinazoline, naphthyridine, 2,3-dihydrobenzofuran, 2,3-dihydrobenzopyrrole, 2,3-dihydrobenzothiophene, dibenzofuran, xanthene, dibenzopyrol, or dibenzothiophene moiety.

The composition may further contain any of the silylated products described herein, including those compounds having a Formula (IV) or (V):

(IV)

or

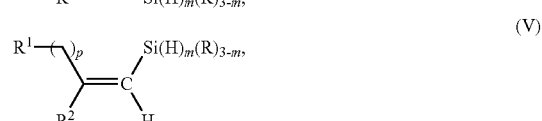
(V)

In other embodiments, when p is 0 and either $R^1$ or $R^2$ is aromatic, the composition may further comprise a terminally silylated compound of the Formula (IX):

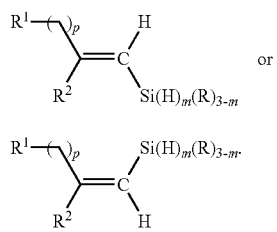
(IX)

The composition may further comprise, when p=1, a terminally silylated olefinic product having a Formula (IV), (V), (VI), or (VII):

(IV)

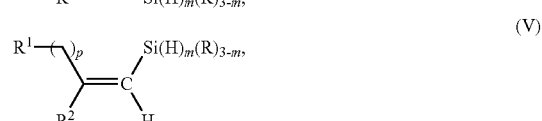
(V)

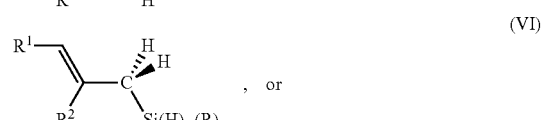
(VI)

, or

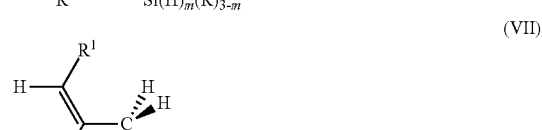
(VII)

In other embodiments, when $R^2$ is aromatic, the composition may further comprise a terminally silylated compound of the formula:

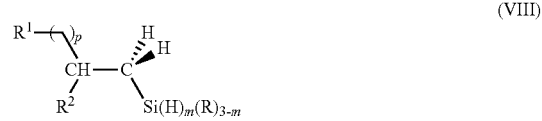
(VIII)

The compositions may contain added transition metal catalysts or species, but in preferred embodiments, the composition contains no added transition metal ions or transition metal catalysts otherwise capable of effecting the silylation of terminal olefins in a reaction where the reaction product is a terminally silylated olefinic product. In some embodiments, the composition is substantially free of transition metal ions or transition metal catalysts otherwise capable of effecting the silylation of terminal olefins in a reaction where the reaction product is a terminally silylated olefinic product. In other embodiments, the composition is substantially free of transition metal ions or transition metal catalysts otherwise capable of effecting the silylation of an aromatic vinyl compound in a reaction where the reaction product is a terminally hydrosilylated product.

Downstream Reactions Using the Products of the Instant Disclosure

Once formed, the products of the disclosed methods can be used as convenient precursors to a range of "downstream" reactions (i.e., reactions to be applied subsequent to the disclosed silylation reactions), depending on the nature of the product. The present disclosure contemplates that methods employing these known methods, when coupled with the inventive methods described here, are within the scope of the present disclosure.

For example, if the product of the reaction comprises a Si—H bond, whether this Si—H bond is associated with the silyl group of a terminally silylated olefinic product or a terminally silylated saturated product, that product may be conveniently used as a building block for the silylation of aromatic (including aryl and heteroaryl) substrates or substrates comprising terminal alkynyl C—H bonds, for example as described in U.S. Pat. No. 9,000,167, U.S. patent application Ser. No. 14/818,417, filed Aug. 5, 2015, U.S. patent application Ser. No. 14/841,964, filed Sep. 1, 2015, and U.S. patent application Ser. No. 14/972,653, filed Dec. 17, 2015, each of which is incorporated by reference herein, at least for for their teachings of the nature and conditions of the silylation reactions. To the extent that such reactions are subsequently done in situ with the original reaction mixture, they offer the possibility of a one-pot synthesis. Alternatively, the terminally silylated olefinic product or a terminally silylated saturated product may be isolated from the original reaction mixture, and optionally purified, and then reacted further with the necessary ingredients to effect the named transformation.

Stated in a different way, in certain embodiments, the methods further comprise reacting a terminally silylated olefinic product (or terminally hydrosilylated product) of Formula (III), (IV), (V), (VI), (VII), (VIII), or (IX), where where m is 1 or 2, with an aromatic substrate under conditions sufficient to silylate the aromatic substrate with the terminally silylated olefinic product (or terminally hydrosilylated product) so as to form a product of the silylation of the aromatic substrate with the terminally silylated olefinic product (or terminally hydrosilylated product). Again, these downstream reactions may use an isolated product of the silylation of the terminal olefins, or one generated in situ.

The reactions of organosilanes and organodisilanes with aromatic substrates are the subject of U.S. Pat. No. 9,000, 167 and U.S. patent application Ser. No. 14/818,417, filed Aug. 5, 2015, and Ser. No. 14/972,653, filed Dec. 17, 2015, each of which is incorporated by reference herein, at least for for their teachings of the nature and conditions of the silylation reactions, the substrates, the compositions used to prepare the same, and the products derived from the reactions. It is expected that the person of skill in the art would be able to use such teachings to effect these transformations using the hydrosilane products of the instant specification. For the same of completeness, these references teach the ability to silylate aromatic substrates comprising at least one of the following structural moieties:

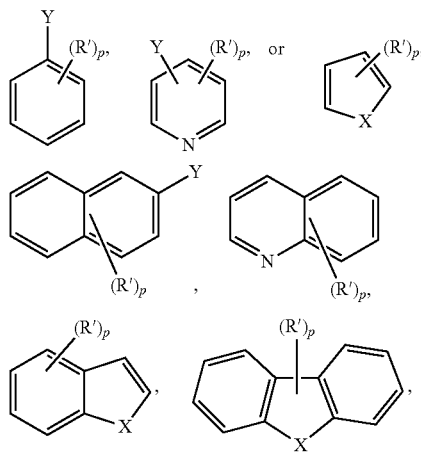

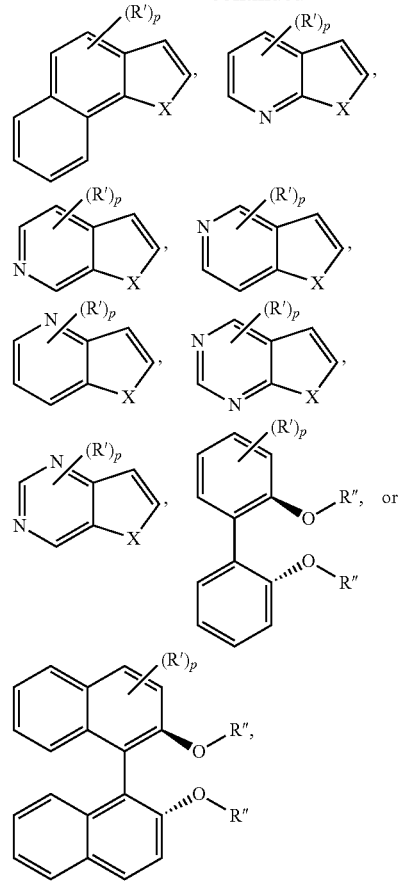

where X is N—R", O, or S;
Y is H, N(R")$_2$, O—R", or S—R"
p is 0 to 4, 0 to 3, 0 to 2, or 0 to 1;
R' is a functional group "Fn," as described elsewhere herein, positioned on either aromatic ring, or (R')$_p$ is an optionally substituted fused alicyclic, heteroalicyclic, aryl or heteroaryl moiety; and
R" is an amine protecting group or an optionally substituted alkyl, aryl, heteroaryl, alkaryl or heteroarylalkyl. In some embodiments, the terminally silylated olefinic product (or terminally hydrosilylated product) is introduced to the aromatic substrate on a 5 or 6-membered ring of that aromatic substrate.

In certain embodiments, the optionally substituted aromatic substrate comprises an optionally substituted phenyl, biphenyl, phenoxy, benzyl, benzyloxy, naphthyl, or naphthyloxy moiety. In other embodiments, the the aromatic substrate comprises an optionally substituted heteroaryl moiety. Exemplary heteroaryl groups include optionally substituted furans, pyrroles, thiophenes, pyrazoles, imidazoles, triazoles, isoxazoles, oxazoles, thiazoles, isothiazoles, oxadiazoles, pyridines, pyridazines, pyrimidines, pyrazines, triazones, benzofurans, benzopyrroles, benzothiophenes, isobenzofurans, isobenzopyrroles, isobenzothiophenes, indoles, isoindoles, indolizines, indazoles, azaindoles, benzisoxazoles, benzoxazoles, quinolines, isoquinolines, cinnolines, quinazolines, naphthyridines, 2,3-dihydrobenzofurans, 2,3-dihydrobenzopyrroles, 2,3-dihydrobenzothiophenes, dibenzofurans, xanthenes, dibenzopyrols, or dibenzothiophenes. The references teach the use of a complement of hydroxides, alkoxides, hydrides, and anionic amides and reaction conditions that are either consistent or compatible with the reagents disclosed in this present application.

Again, where the product of the reaction of the present disclosure comprises a Si—H bond (as in a compound of Formulae (III), (IV), (V), (VI), VII), (VIII), or (IX), where m is 1 or 2), that product may also be conveniently used as a building block for the silylation of substrates comprising terminal alkynyl C—H bonds. In such embodiments, any of the methods disclosed to this point may further comprise reacting the terminally silylated olefinic product (or terminally hydrosilylated product) with an organic substrate comprising a terminal alkyne, under conditions sufficient to form a silylated terminal alkynyl moiety, so as to form a silylated terminal alkynyl moiety.

The conditions for such silylations can be found in U.S. patent application Ser. No. 14/841,964, filed Sep. 1, 2015, which is incorporated by reference herein in its entirety for its teachings of the nature and conditions of these silylation reactions, the substrates, the compositions used to prepare the same, and the products derived from the reactions. In these embodiments, the organic substrate comprising the terminal alkynyl C—H bond can have a formula:

$$R^3\text{—}C\equiv C\text{—}H,$$

where $R^3$ comprises H, an optionally substituted $C_{1-18}$ alkyl, optionally substituted $C_{2-18}$ alkenyl, optionally substituted $C_{2-18}$ alkynyl, optionally substituted $C_{1-18}$ membered heteroalkyl, optionally substituted 6-18 ring membered aryl, optionally substituted 6-18 ring membered aryloxy, optionally substituted 6-18 ring membered aralkyl, optionally substituted 6-18 ring membered aralkyloxy, optionally substituted 5-18 ring membered heteroaryl, optionally substituted 5-18 ring membered heteroaryloxy, optionally substituted 5-18 ring membered heteroarylalkyl, optionally substituted 5-18 ring membered heteroaralkyloxy, or optionally substituted metallocene. In certain of these embodiments, the aromatic substrate comprises an optionally substituted phenyl, biphenyl, phenoxy, benzyl, benzyloxy, naphthyl, or naphthyloxy moiety. In other embodiments, the aromatic substrate comprises an optionally substituted heteroaryl moiety. In some embodiments, the heteroalkyl moiety comprises an optionally substituted furan, pyrrole, thiophene, pyrazole, imidazole, triazole, isoxazole, oxazole, thiazole, isothiazole, oxadiazole, pyridine, pyridazine, pyrimidine, pyrazine, triazone, benzofuran, benzopyrrole, benzothiophene, isobenzofuran, isobenzopyrrole, isobenzothiophene, indole, isoindole, indolizine, indazole, azaindole, benzisoxazole, benzoxazole, quinoline, isoquinoline, cinnoline, quinazoline, naphthyridine, 2,3-dihydrobenzofuran, 2,3-dihydrobenzopyrrole, 2,3-dihydrobenzothiophene, dibenzofuran, xanthene, dibenzopyrrole, or dibenzothiophene moiety. The reference teach a complement of organosilanes (hydrosilanes), together with the bases useful for these transformations, all of which are either consistent or compatible with the reagents disclosed in this present application Also, where the products of the reaction comprise a terminally silylated olefinic product, for example, a vinyl silane or allylic silane, these products may be conveniently used as building blocks for additional reactions where such materials are known to be used, again either in situ or as isolated products.

For example, such terminally silylated olefinic products may be polymerized by suitable methods, either by themselves or copolymerized with other olefinic or acetylenic precursors. In other embodiments, the original silylated product may also be reacted with such a second, unsaturated organic moiety (cyclic or acyclic, comprising optionally substituted alkene, alkyne, azide, nitrile, isocyanate, isothiocyanate, carbonyl, amide, urea, etc.) in a cross-metathesis reaction to form a polymerized silylated product. Such cross-metathesis metathesis reactions are well-known, and the person of ordinary skill would know how to effect these transformations. For example, the use of Grubbs-type ruthenium carbene metathesis catalysts may be used for this purpose, though the contemplated transformations are not limited to these types of catalysts. The reactions may be intra- or intermolecular, single- or multi-pot syntheses, and provide another method for incorporating silyl groups under facile and mild conditions. Such downstream transformations are described, for example, in Kim, et al., *J. Amer. Chem. Soc.*, 126 (33), 2004, 10242-10243, which is incorporated by reference herein for its teaching in at least this regard.

Alternatively, or additionally, the original silylated product may be copolymerized with an optionally substituted enyne, diene, diyne, or cyclic olefin, using any suitable catalyst(s) to form silylated polymers. In certain embodiments, these reactions may comprise metathesis polymerization, for example ROMP. Such metathesis polymerization reactions are well-known, and the person of ordinary skill would know how to affect them, for example, again using Grubbs-type ruthenium carbene metathesis catalysts, though the contemplated transformations are not limited to these types of catalysts.

Vinyl and allylic silanes are also useful synthons for use in the Alder-ene reaction, also known as the ene reaction, in which an activated alkene with an allylic hydrogen reacts with a compound containing a multiple bond (the enophile) to form a new sigma-bond with the migration of the ene-double bond and a 1,5, hydride shift (e.g., where the vinyl silane or the allylic silane can variously act as either the ene or enophile). The product of such a reaction is a substituted alkene with the double bond shifted to the allylic position. Such enes may include a >C=C<, >C=O, (e.g., aldehydes, amides, esters, and ketones), >C=N—, >C=S, —N=N—, or —C≡N moiety (depicted below as $R^A$—X=Y—$R^B$). The presence of the silyl group appears to provide sufficient activation for this reaction to proceed without excess energy. Such reactions are known to be conducted without catalysts or with cobalt catalysts. See, e.g., Hilt., G., et al., *Org. Lett.*, 2011, 13 (2), pp. 304-307 and In one exemplary reaction scheme:

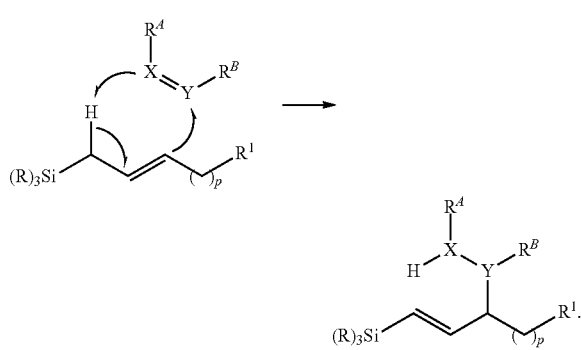

In another example of the utility of vinyl and allyl silanes, such materials may be reacted in the presence of substituted ene-ones to result in the incorporation of a hydroxy group.

A benzyldimethylsilyl (BDMS) group has been especially suitable for such transformations when used in the presence of Lewis acid catalysts, such as titanium-based catalysts. Such reactions have been described, for example, in K. Miura, et al., *Tetrahedron Letters*, 41 (2000) 2129-2132:

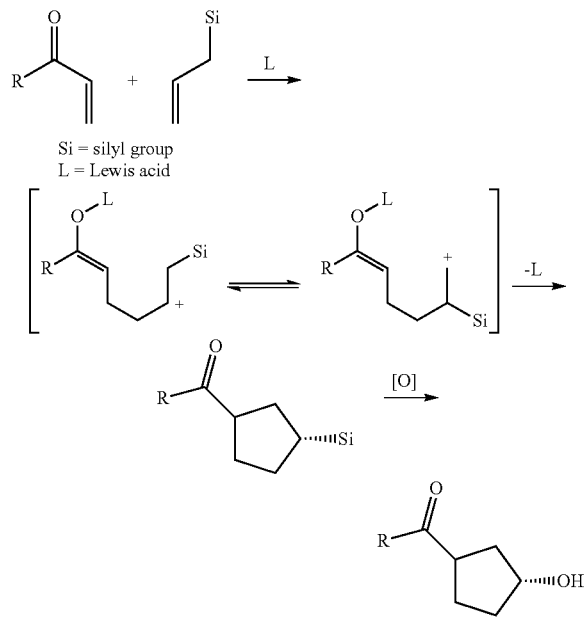

In related transformations, when the vinyl silane bears a suitably placed hydroxy group, reactions such as follows may be achieved:

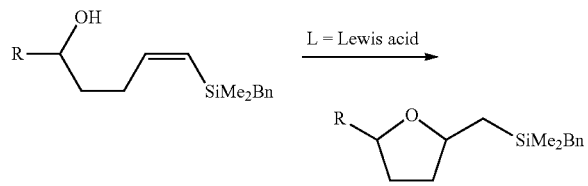

In other embodiments, the original silylated product may be further reacted to hydrogenate the silylated vinyl or allylic moiety. These vinyl or allylic silanes may also be reacted with water, alcohols, hydrogen cyanide, hydrogen chloride, dihalogen, or carboxylic acids under conditions known to give corresponding hydroxy, alkoxy, cyano, halo, or ester products. Again, the skilled artisan would be able to affect these transformations without undue effort.

Vinyl silanes are useful precursors for still other organic transformations, and the reactions of the products of the presently described methods are also considered within the scope of the present disclosure.

For example, vinyl silanes are known to be suitable synthons for cross coupling with palladium catalysts (for example Pd(OAc)$_2$, with replacement of the silyl group by alkyl and aryl/heteroaryl moieties, e.g.,

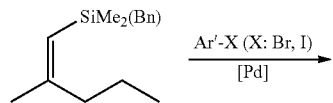

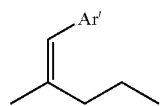

where Ar'—X refers to an optionally substituted aryl or heteroaryl bromide or iodide. Such reactions are known, see, e.g., Trost, B., et al., *Org. Lett.* 2003, 5 (11), pp. 1895-1898; M. G. McLaughlin, et al. Cook, *Org. Lett.*, 2015, 17, 10-13, S. E. Denmark, S. A. Tymonko, *J. Am. Chem. Soc.*, 2005, 127, 8004-8005, which are incorporated by reference herein at least for their teachings of the conditions and reagents used for such transformations. Similar reaction cross-coupling reactions are known for vinyl silanes which are activated by TBAF (n-Bu$_4$NF), forming the pentacoordinate silicate complex which undergoes transmetallation with palladium catalyst.

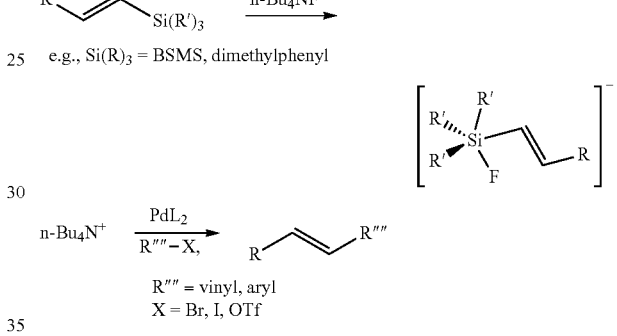

It should be appreciated that the ability to replace the added silane moiety with an hydrocarbyl moiety provides a significant advance in the chemists toolbox, given that the overall reaction provides a route to replace a terminal olefinic C—H bond to a substituted alkyl, alkenyl, aryl, heteroaryl, or similar moiety. Such further reactions of the silanes formed as described in the instant disclosure are considered within the scope of this disclosure.

In another example, the allylic silanes may be reacted with strong base (e.g., alkyl lithium or potassium tert-butoxide), then with an alkyl halide to form substituted vinyl silyl products. In separate embodiments, these products, or the vinyl silanes of the present application may further be reacted with I$_2$ or with ICl so as to form a terminal vinyl iodide. Such reactions form the vinyl iodide with the displacement of the silyl group, and are typically done in methylene chloride at low temperatures. Both of these types of reactions and their reaction conditions are described in Koumagio, et al., *Tetrahedron Lett.*, 1984, 25, 717, which is incorporated by reference herein for its teaching of the methods used in effecting such transformations.

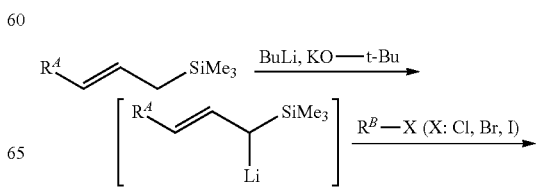

-continued

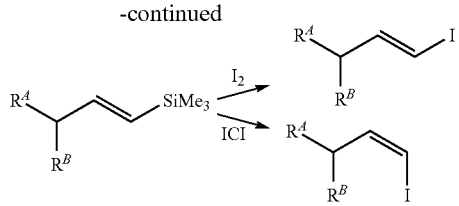

In yet another example, the vinyl silanes of the present application may further be reacted with polyolefins, such as polyethylene, so as to form a silane grafted polyolefin. Such reactions are typically done in the presence of a peroxide or other radical source. Such reactions using vinylsiloxanes are known in the rubber compounding industry, though it is expected that vinyl silanes may also work in this capacity.

In yet another example, vinyl silanes of the present application may further be epoxidized, for example by reacting with an organic peroxide (for example m-CPBA) to form a terminal silylated peroxide. Such a derivative may provide a useful synthon for the formation of aldehydes when treated with a strong acid (e.g., perchloric acid, formic acid, or TFA) forms an aldehyde moiety (in case of 1-silyl-2-disubstituted terminal alkene):

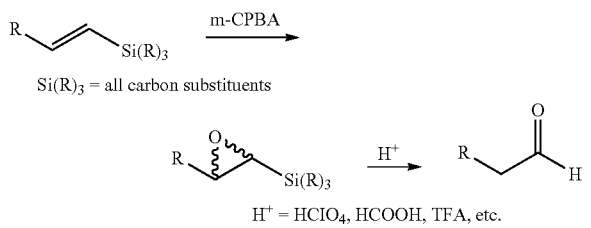

Such reactions have been described in Suzuki, K. et al., *Org. Lett.* 2004, 6, 409-411 and Dudley, B. et al., *Org. Lett.* 2007, 9, 2839-2842, which are incorporated by reference at least for their teachings of the specific reaction conditions.

In still another example, the vinyl silanes of the instant disclosure can be reacted with a fluoride source, hydrogen peroxide, and base to form an aldehyde, according to the well-known Tamao-Fleming Oxidation reaction:

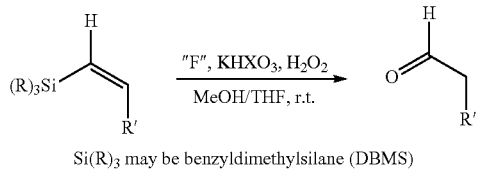

Such reactions are known, for example, Trost, B. M., et al., *Chem. Int. Ed.* 2003, 42, 3415-3418, which is incorporated by reference for its teachings. The skilled artisan would be able to practice this further reaction without undue experimentation.

In still another example, the vinyl silanes of the instant disclosure can be reacted with an iodosyl benzene to form a vinyliodonium tetrafluoroborate. Exemplary conditions include the use of iodosylbenzene in the presence of $BF_3$-diethyl etherate at low temperature followed by quenching with aqueous sodium tetrafluoroborate. See also Ochiai, M., et al., *Tetrahedron*, 44, 13, 1988, pp. 4095-4112. Such reagents are useful for the preparation of vinyl aromatic products, for example, styrene derivatives:

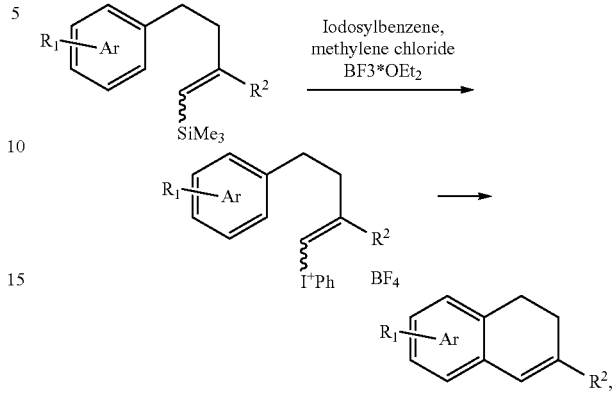

where Ar represents an aromatic moiety.

The use of trimethyl vinyl silanes are also useful synthons for the so-called Hosomi-Sakurai reaction, in which, in combination with strong Lewis acids such as $TiCl_4$ or $BF_3*OEt_2$, various electrophiles such as acid chlorides, aldehydes, epoxides, imines, ketals, or ketones can be allylated under mild conditions.

These representative examples show the wealth of downstream reactions available from the preparation of the disclosed products. Again, the use of these methods, in conjunction with the methods described herein, are all considered within the scope of the present invention.

Terms

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. Finally, while an embodiment may be described as part of a series of steps or part of a more general structure, each said step may also be considered an independent embodiment in itself, combinable with others.

The transitional terms "comprising," "consisting essentially of" and "consisting" are intended to connote their generally in accepted meanings in the patent vernacular; that is, (i) "comprising," which is synonymous with "including," "containing," or "characterized by," is inclusive or open-ended and does not exclude additional, unrecited elements or method steps; (ii) "consisting of" excludes any element, step, or ingredient not specified in the claim; and (iii) "consisting essentially of" limits the scope of a claim to the specified materials or steps and those that do not materially affect the basic and novel characteristic(s) of the claimed invention. Embodiments described in terms of the phrase "comprising" (or its equivalents), also provide, as embodiments, those which are independently described in terms of "consisting of" and "consisting essentially of" For those embodiments provided in terms of "consisting essentially of" the basic and novel characteristic(s) is the facile operability of the methods to provide silylated products at meaningful yields (or the ability of the systems used in such methods to provide the product compositions at meaningful yields or the compositions derived therefrom); i.e., to silylate terminal olefins C(sp2)-H moieties using only those ingredients listed. In those embodiments that provide a system or method comprises the use of a mixture consisting essentially of the substrate, organosilane or organodisilane), and strong base (sodium or potassium hydroxide, alkoxide, hydride, or anionic amide), it refers to the fact that this system operates to silylate the substrate at rates corresponding to those described herein under comparable conditions as described herein without additional (e.g., transition metal) catalysts or plasma or UV radiation sources. While some level of transition metals may be present (for example, as a substrate), they are not needed for the operability of the methods, and may be considered spectators for purposes of this reaction.

The term "meaningful product yields" is intended to reflect product yields of greater than 20%, but when specified, this term may also refer to yields of 10%, 20%, 30%, 40%, 50%, 60%, 70%, 80%, or 90% or more, relative to the amount of original substrate.

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C." Similarly, a designation such as $C_{1-3}$ includes not only $C_{1-3}$, but also $C_1$, $C_2$, $C_3$, $C_{1-2}$, $C_{2-3}$, and $C_{1,3}$, as separate embodiments.

Throughout this specification, words are to be afforded their normal meaning, as would be understood by those skilled in the relevant art. However, so as to avoid misunderstanding, the meanings of certain terms will be specifically defined or clarified.

The term "alkyl" as used herein refers to a linear, branched, or cyclic saturated hydrocarbon group typically although not necessarily containing 1 to about 24 carbon atoms, preferably 1 to about 12 carbon atoms, such as methyl, ethyl, n-propyl, isopropyl, n-butyl, sec-butyl, isobutyl, tert-butyl, octyl, decyl, and the like, as well as cycloalkyl groups such as cyclopentyl, cyclohexyl and the like. Generally, although again not necessarily, alkyl groups herein contain 1 to about 12 carbon atoms. The term also includes "lower alkyl" as separate embodiments, which refers to an alkyl group of 1 to 6 carbon atoms, and the specific term "cycloalkyl" intends a cyclic alkyl group, typically having 4 to 8, preferably 5 to 7, carbon atoms. The term "substituted alkyl" refers to alkyl groups substituted with one or more substituent groups, and the terms "heteroatom-containing alkyl" and "heteroalkyl" refer to alkyl groups in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl groups, respectively.

The term "alkylene" as used herein refers to a difunctional linear, branched, or cyclic alkyl group, where "alkyl" is as defined above.

The term "alkenyl" as used herein refers to a linear, branched, or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Preferred alkenyl groups herein contain 2 to about 12 carbon atoms. The term also includes "lower alkenyl" as separate embodiments, which refers to an alkenyl group of 2 to 6 carbon atoms, and the specific term "cycloalkenyl" intends a cyclic alkenyl group, preferably having 5 to 8 carbon atoms. The term "substituted alkenyl" refers to alkenyl groups substituted with one or more substituent groups, and the terms "heteroatom-containing alkenyl" and "heteroalkenyl" refer to alkenyl groups in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl groups, respectively.

The term "alkenylene" as used herein refers to a difunctional linear, branched, or cyclic alkenyl group, where "alkenyl" is as defined above.

The term "alkynyl" as used herein refers to a linear or branched hydrocarbon group of 2 to about 24 carbon atoms containing at least one triple bond, such as ethynyl, n-propynyl, and the like. Preferred alkynyl groups herein contain 2 to about 12 carbon atoms. The term "lower alkynyl" intends an alkynyl group of 2 to 6 carbon atoms. The term also includes "lower alkynyl" as separate embodiments, which refers to an alkynyl group substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include a linear, branched, unsubstituted, substituted, and/or heteroatom-containing alkynyl and lower alkynyl group, respectively.

The term "alkoxy" as used herein intends an alkyl group bound through a single, terminal ether linkage; that is, an "alkoxy" group may be represented as —O-alkyl where alkyl is as defined above. The term also includes "lower alkoxy" as separate embodiments, which refers to an alkoxy group containing 1 to 6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aromatic" refers to the ring moieties which satisfy the Hückel 4n+2 rule for aromaticity, and includes both aryl (i.e., carbocyclic) and heteroaryl (also called heteroaromatic) structures, including aryl, aralkyl, alkaryl, heteroaryl, heteroaralkyl, or alk-heteroaryl moieties, or pre-polymeric (e.g., monomeric, dimeric), oligomeric or polymeric analogs thereof.

The term "aryl" as used herein, and unless otherwise specified, refers to a carbocyclic aromatic substituent or structure containing a single aromatic ring or multiple aromatic rings that are fused together, directly linked, or indirectly linked (such that the different aromatic rings are bound to a common group such as a methylene or ethylene moiety). Preferred aryl groups contain 6 to 24 carbon atoms, and particularly preferred aryl groups contain 6 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituents in which at least one carbon atom is replaced with a heteroatom, as will be described in further detail infra.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 6 to 24 carbon atoms, and particularly preferred aryloxy groups contain 6 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Preferred alkaryl and aralkyl groups contain 7 to 24 carbon atoms, and particularly preferred alkaryl and aralkyl groups contain 7 to 16 carbon atoms. Alkaryl groups include, for example, p-methylphenyl, 2,4-dimethylphenyl, p-cyclohexylphenyl, 2, 7-dimethylnaphthyl, 7-cyclooctyl-naphthyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. The terms "alkaryloxy" and "aralkyloxy" refer to substituents of the formula —OR wherein R is alkaryl or aralkyl, respectively, as just defined.

The term "acyl" refers to substituents having the formula —(CO)-alkyl, —(CO)-aryl, or —(CO)-aralkyl, and the term "acyloxy" refers to substituents having the formula —O(CO)-alkyl, —O(CO)-aryl, or —O(CO)-aralkyl, wherein "alkyl," "aryl, and "aralkyl" are as defined above.

The terms "cyclic" and "ring" refer to alicyclic or aromatic groups that may or may not be substituted and/or heteroatom-containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic, or polycyclic. The term "acyclic" refers to a structure in which the double bond is not contained within a ring structure.

The terms "halo," "halide," and "halogen" are used in the conventional sense to refer to a chloro, bromo, fluoro, or iodo substituent.

"Hydrocarbyl" refers to univalent hydrocarbyl radicals containing 1 to about 30 carbon atoms, preferably 1 to about 24 carbon atoms, most preferably 1 to about 12 carbon atoms, including linear, branched, cyclic, saturated, and unsaturated species, such as alkyl groups, alkenyl groups, aryl groups, and the like. The term "lower hydrocarbyl" intends a hydrocarbyl group of 1 to 6 carbon atoms, preferably 1 to 4 carbon atoms, and the term "hydrocarbylene" intends a divalent hydrocarbyl moiety containing 1 to about 30 carbon atoms, preferably 1 to about 24 carbon atoms, most preferably 1 to about 12 carbon atoms, including linear, branched, cyclic, saturated and unsaturated species. The term "lower hydrocarbylene" intends a hydrocarbylene group of 1 to 6 carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and "heterohydrocarbylene" refer to hydrocarbylene in which at least one carbon atom is replaced with a heteroatom. Unless otherwise indicated, the term "hydrocarbyl" and "hydrocarbylene" are to be interpreted as including substituted and/or heteroatom-containing hydrocarbyl and hydrocarbylene moieties, respectively.

The term "heteroatom-containing" as in a "heteroatom-containing hydrocarbyl group" refers to a hydrocarbon molecule or a hydrocarbyl molecular fragment in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl." Examples of heteroalkyl groups include alkoxyaryl, alkylsulfanyl-substituted alkyl, N-alkylated amino alkyl, and the like. Non-limiting examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

As used herein, the terms "substrate" or "organic substrate" are intended to connote both discrete small molecules (sometimes described as "organic compounds") and oligomers and polymers containing a terminal olefinic group. The term "aromatic moieties" is intended to refer to those portions of the compounds, pre-polymers (i.e., monomeric compounds capable of polymerizing), oligomers, or polymers having at least one of the indicated aromatic structures. Where shown as structures, the moieties contain at least that which is shown, as well as containing further functionalization, substituents, or both, including but not limited to the functionalization described as "Fn" herein.

By "substituted" as in "substituted hydrocarbyl," "substituted alkyl," "substituted aryl," and the like, as alluded to in some of the aforementioned definitions, is meant that in the hydrocarbyl, alkyl, aryl, heteroaryl, or other moiety, at least one hydrogen atom bound to a carbon (or other) atom is replaced with one or more non-hydrogen substituents. Examples of such substituents include, without limitation: functional groups referred to herein as "Fn," such as halo (e.g., F, Cl, Br, I), hydroxyl, sulfhydryl, $C_1$-$C_{24}$ alkoxy, $C_2$-$C_{24}$ alkenyloxy, $C_2$-$C_{24}$ alkynyloxy, $C_5$-$C_{24}$ aryloxy, $C_6$-$C_{24}$ aralkyloxy, $C_6$-$C_{24}$ alkaryloxy, acyl (including $C_1$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl ((CO)—O-alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO—), carbamoyl (—(CO)—$NH_2$), mono-($C_1$-$C_{24}$ substituted carbamoyl (—(CO)NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_1$-$C_{24}$ haloalkyl)-substituted carbamoyl (—(CO)—NH($C_1$-$C_{24}$ alkyl)), di-($C_1$-$C_{24}$ haloalkyl)-substituted carbamoyl (—(CO)—N($C_1$-$C_{24}$ alkyl)$_2$), mono-($C_5$-$C_{24}$ aryl)-substituted carbamoyl (—(CO)—NH-aryl), di-($C_5$-$C_{24}$ aryl)substituted carbamoyl (—(CO)—N($C_5$-$C_{24}$ aryl)$_2$), alkyl), N—($C_5$-$C_{24}$ aryl)-substituted carbamoyl, thiocarbamoyl (—(CS)—$NH_2$), mono-($C_1$-$C_{24}$ alkyl)-substituted thiocarbamoyl (—(CO)—NH($C_1$-$C_{24}$ alkyl)), di-($C_1$-$C_{24}$ substituted thiocarbamoyl (—(CO)—N($C_1$-$C_{24}$ alkyl)$_2$), mono-($C_5$-$C_{24}$ aryl)substituted thiocarbamoyl (—(CO)—NH-aryl), di-($C_5$-$C_{24}$ aryl)-substituted thiocarbamoyl (—(CO)—N($C_5$-$C_{24}$ aryl)$_2$), alkyl), N—($C_5$-$C_{24}$ aryl)-substituted thiocarbamoyl, carbamido (—NH—(CO)—$NH_2$), cyano(—C≡N), cyanato (—O—C≡N), thiocyanato (—S—C≡N), formyl (—(CO)—H), thioformyl (—(CS)—H), amino (—$NH_2$), mono-($C_1$-$C_{24}$ alkyl)-substituted amino, di-($C_1$-$C_{24}$ alkyl)-substituted amino, mono-($C_5$-$C_{24}$ aryl)substituted amino, di-($C_5$-$C_{24}$ aryl)-substituted amino, $C_1$-$C_{24}$ alkylamido (—NH—(CO)-alkyl), $C_6$-$C_{24}$ arylamido (—NH—(CO)-aryl), imino (—CR=NH where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CR=N(alkyl), where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR=N(aryl), where R=hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—$NO_2$), nitroso (—NO), sulfo (—$SO_2$OH), sulfonate($SO_2$O—), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—$SO_2$-alkyl), $C_1$-$C_{24}$ monoalkylaminosulfonyl-$SO_2$—N(H) alkyl), $C_1$-$C_{24}$ dialkylaminosulfonyl-$SO_2$—N(alkyl)$_2$, $C_5$-$C_{24}$ arylsulfonyl (—$SO_2$-aryl), boryl (—$BH_2$), borono (—B(OH)$_2$), boronato (—B(OR)$_2$ where R is alkyl or other hydrocarbyl), phosphono (—P(O)(OH)$_2$), phosphonato (—P(O)(O)$_2$), phosphinato (P(O)(O—)), phospho (—$PO_2$), and phosphine (—$PH_2$); and the hydrocarbyl moieties $C_1$-$C_{24}$ alkyl (preferably $C_1$-$C_{12}$ alkyl, more preferably $C_1$-$C_6$ alkyl), $C_2$-$C_{24}$ alkenyl (preferably $C_2$-$C_{12}$ alkenyl, more preferably $C_2$-$C_6$ alkenyl), $C_2$-$C_{24}$ alkynyl (preferably $C_2$-$C_{12}$ alkynyl, more preferably C2-C6 alkynyl), $C_5$-$C_{24}$ aryl (preferably $C_5$-$C_{24}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl). Within these substituent structures, the "alkyl," "alkylene," "alkenyl," "alkenylene," "alkynyl," "alkynylene," "alkoxy," "aromatic," "aryl," "aryloxy," "alkaryl," and "aralkyl" moieties may be optionally fluorinated or perfluorinated. Additionally, reference to alcohols, aldehydes, amines, carboxylic acids, ketones, or other similarly reactive functional groups also includes their protected analogs. For example, reference to hydroxy or alcohol also includes those substituents wherein the hydroxy is protected by acetyl (Ac), benzoyl (Bz), benzyl (Bn), β-Methoxyethoxymethyl ether (MEM), dimethoxytrityl, [bis-(4-methoxyphenyl)phenylmethyl] (DMT), methoxymethyl ether (MOM), methoxytrityl [(4-methoxyphenyl)diphenylmethyl, MMT), p-methoxybenzyl ether (PMB), methylthiomethyl ether, pivaloyl (Piv), tetrahydropyranyl (THP), tetrahydrofuran (THF), trityl (triphenylmethyl, Tr), silyl ether (most popular ones include trimethylsilyl (TMS), tert-butyldimethylsilyl (TBDMS), tri-iso-propylsilyloxymethyl (TOM), and triisopropylsilyl (TIPS) ethers), ethoxyethyl ethers (EE). Reference to amines also includes those substituents wherein the amine is protected by a BOC glycine, carbobenzyloxy (Cbz), p-methoxybenzyl carbonyl (Moz or MeOZ), tert-butyloxycarbonyl (BOC), 9-fluorenylmethyloxycarbonyl (FMOC), acetyl (Ac), benzoyl (Bz), benzyl (Bn), carbamate, p-methoxybenzyl (PMB), 3,4-dimethoxybenzyl (DMPM), p-methoxyphenyl (PMP), tosyl (Ts) group, or sulfonamide (Nosyl & Nps) group. Reference to substituent containing a carbonyl group also includes those substituents wherein the carbonyl is protected by an acetal or ketal, acylal, or diathane group. Reference to substituent containing a carboxylic acid or carboxylate group also includes those substituents wherein the carboxylic acid or carboxylate group is protected by its methyl ester, benzyl ester, tert-butyl ester, an ester of 2,6-disubstituted phenol (e.g. 2,6-dimethylphenol, 2,6-diisopropylphenol, 2,6-di-tert-butylphenol), a silyl ester, an orthoester, or an oxazoline. Preferred substituents are those identified herein as not or less affecting the silylation chemistries, for example, including those substituents comprising alkyls; alkoxides, aryloxides, aralkylalkoxides, protected carbonyl groups; aryls optionally substituted with F, Cl, —$CF_3$; epoxides; N-alkyl aziridines; cis- and trans-olefins; acetylenes; pyridines, primary, secondary and tertiary amines; phosphines; and hydroxides.

By "functionalized" as in "functionalized hydrocarbyl," "functionalized alkyl," "functionalized olefin," "functionalized cyclic olefin," and the like, is meant that in the hydrocarbyl, alkyl, aryl, heteroaryl, olefin, cyclic olefin, or other moiety, at least one hydrogen atom bound to a carbon (or other) atom is replaced with one or more functional groups such as those described herein and above. The term "functional group" is meant to include any of the substituents described herein with the ambit of "Fn.".

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom or organic moiety, and, thus, the description includes structures wherein a non-hydrogen substituent is present and structures wherein a non-hydrogen substituent is not present.

As used herein, the terms "organosilane" or "hydrosilane" may be used interchangeably and refer to a compound or reagent having at least one silicon-hydrogen (Si—H) bond and preferably at least one carbon-containing moiety. The organosilane may further contain a silicon-carbon, a silicon-oxygen (i.e., encompassing the term "organosiloxane"), a silicon-nitrogen bond, or a combination thereof, and may be monomeric, or contained within an oligomeric or polymeric framework, including being tethered to a heterogeneous or homogeneous support structure.

As used herein, the terms "organodisilane" and "disilane" are used interchangeably and refer to a compound or reagent having at least one Si—Si bond. These terms include those embodiments where the disilane contains at least one Si—H bond and those embodiments wherein the disilane no silicon-hydrogen (Si—H) bonds. While the present disclosure refers to the reaction of compounds having Si—Si bonds, the optional presence of Si—H bonds may allow the reaction to proceed through reaction manifolds also described for silylations using organosilane reagents. Such a Si—H pathway is not required for silylation to proceed in the disilane systems, but where the silylating reagent contains both a Si—Si and Si—H bond, the reactions may operate in parallel with one another. The organodisilane may further contain a silicon-carbon, a silicon-oxygen, a silicon-nitrogen bond, or a combination thereof, and may be monomeric, or contained within an oligomeric or polymeric framework, including being tethered to a heterogeneous or homogeneous support structure.

As used herein, unless explicitly stated to the contrary, the organosilanes or organodisilanes are intended to refer to materials that contain no Si-halogen bonds. However, in some embodiments, the organosilanes or organodisilanes may contain a Si-halogen bond.

As used herein, the terms "silylating" or "silylation" refer to the forming of carbon-silicon bonds, in a position previously occupied by a carbon-hydrogen bond, often a non-activated C—H bond. Silylating may be seen as coupling of a C—H and Si—H bond or a C—H and Si—Si bond to form a C—Si bond. The ability to replace directly a C—H bond with a C—Si bond, under the conditions described herein, is believed to be unprecedented. By contrast, the terms "hydrosilylating" or "hydrosilylation" refers to the addition of the H—Si(R)$_3$ group across the olefinic (double) bond, resulting in the formation of an alkyl or alkylene silane. In the present methods, this hydrosilylation reaction appears to occur most readily where the terminal olefin product would be conjugated to an aromatic moiety within the substrate.

As used herein, the term "substantially free of a transition-metal compound" is intended to reflect that the system is effective for its intended purpose of silylating terminal alkyne C—H bonds under the relatively mild conditions described herein, even in the absence of any exogenous (i.e., deliberately added or otherwise) transition-metal catalyst(s). While certain embodiments provide that transition metals, including those capable of catalyzing silylation reactions, may be present within the systems or methods described herein at levels normally associated with such catalytic activity (for example, in the case where the substrates comprise metallocenes), the presence of such metals (either as catalysts or spectator compounds) is not required and in many cases is not desirable. As such, in many preferred embodiments, the system and methods are "substantially free of transition-metal compounds." Unless otherwise stated, then, the term "substantially free of a transition-metal compound" is defined to reflect that the total level of transition metal within the silylating system, independently or in the presence of organic substrate, is less than about 5 ppm, as measured by ICP-MS. When expressly stated as such, additional embodiments also provide that the concentration of transition metals is less than about 10 wt %, 5 wt %, 1 wt %, 100 ppm, 50 ppm, 30 ppm, 25 ppm, 20 ppm, 15 ppm, 10 ppm, or 5 ppm to about 1 ppm or 0 ppm. As used herein, the term "transition metal" is defined to include d-block elements, for example Ag, Au, Co, Cr, Rh, Ir, Fe, Ru, Os, Ni, Pd, Pt, Cu, Zn, or combinations thereof. In further specific independent embodiments, the concentration of Ni, as measured by ICP-MS, is less than 25 ppm, less than 10 ppm, less than 5 ppm, or less than 1 ppm.

While it may not be necessary to limit the system's exposure to water and oxygen, in some embodiments, the chemical systems and the methods are done in an environment substantially free of water, oxygen, or both water and oxygen. In other embodiments, air and/or water are present. Unless otherwise specified, the term "substantially free of water" refers to levels of water less than about 500 ppm and "substantially free of oxygen" refers to oxygen levels corresponding to partial pressures less than 1 torr. Where stated, additional independent embodiments may provide that "substantially free of water" refers to levels of water less than 1.5 wt %, 1 wt %, 0.5 wt %, 1000 ppm, 500 ppm, 250 ppm, 100 ppm, 50 ppm, 10 ppm, or 1 ppm and "substantially free of oxygen" refers to oxygen levels corresponding to partial pressures less than 50 torr, 10 torr, 5 torr, 1 torr, 500 millitorr, 250 millitorr, 100 millitorr, 50 millitorr, or 10 millitorr. In the General Procedure described herein, deliberate efforts were made to exclude both water and oxygen, unless otherwise specified.

The term "terminally silylated olefinic product" refers to an olefinic product of the reactions as described herein, and includes terminally substituted vinyl silanes or allylic silanes. The term "terminally silylated olefinic moiety" refers to the silyl moiety of the terminally silylated olefinic product, whether the product is an allylic or vinyl silyl compound. The term "terminally hydrosilylated product" refers to a product in wherein the silyl group is positioned at a terminal position of an ethylene linkage, typically the result of an anti-Markovnikov hydrosilylation addition to a vinyl aromatic substrate.

In some embodiments, more than one silyl group is added to the starting material, but generally the product still contains a silyl group at the terminal position.

The following listing of Embodiments is intended to complement, rather than displace or supersede, the previous descriptions.

Embodiment 1

A method comprising or consisting essentially of contacting at least one organic substrate comprising a terminal olefin with:

(a) an organosilane, organodisilane, or mixture thereof and (b) an alkali metal alkoxide, an alkali metal hydroxide, an alkaline earth metal alkoxide, and alkaline earth hydroxide, an alkali metal amide (such as a potassium bis(trimethylsilyl) amide, KHMDS), or a mixture thereof, such that the contacting results in the formation of a terminally silylated olefinic product or a terminally hydrosilylated product, the latter apparently favored when using vinyl aromatic substrates.

Embodiment 2

The method of Embodiment 1, wherein the organosilane has a structure of Formula (I) and the organodisilane has a structure of Formula (II):

$(R)_{3-m}Si(H)_{m+1}$     (I)

$(R)_{3-m}(H)_mSi—Si(R)_{3-m}(H)_m$     (II)

where: m is independently 0, 1, or 2; and each R is independently optionally substituted $C_{1-24}$ alkyl or heteroalkyl, optionally substituted $C_{2-24}$ alkenyl or heteroalkenyl, optionally substituted $C_{2-24}$ alkynyl or heteroalkynyl, optionally substituted 6 to 18 ring membered aryl or 5 to 18 ring membered heteroaryl, optionally substituted 6 to 18 ring-membered alkaryl or 5 to 18 ring-membered heteroalkaryl, optionally substituted 6 to 18 ring-membered aralkyl or 5 to 18 ring-membered heteroaralkyl, optionally substituted —O—$C_{1-24}$ alkyl or heteroalkyl, optionally substituted 6 to 18 ring-membered aryloxy or 5 to 18 ring-membered heteroaryloxy, optionally substituted 6 to 18 ring-membered alkaryloxy or 5 to 18 ring-membered heteroalkaryloxy, or optionally substituted 6 to 18 ring-membered aralkoxy or 5 to 18 ring-membered heteroaralkoxy, and, if substituted, the substituents may be phosphonato, phosphoryl, phosphanyl, phosphino, sulfonato, $C_1$-$C_{20}$ alkylsulfanyl, $C_5$-$C_{20}$ arylsulfanyl, $C_1$-$C_{20}$ alkylsulfonyl, $C_5$-$C_{20}$ arylsulfonyl, $C_1$-$C_{20}$ alkylsulfinyl, 5 to 12 ring-membered arylsulfinyl, sulfonamido, amino, amido, imino, nitro, nitroso, hydroxyl, $C_1$-$C_{20}$ alkoxy, $C_5$-$C_{20}$ aryloxy, $C_2$-$C_{20}$ alkoxycarbonyl, $C_5$-$C_{20}$ aryloxycarbonyl, carboxyl, carboxylato, mercapto, formyl, $C_1$-$C_{20}$ thioester, cyano, cyanato, thiocyanato, isocyanate, thioisocyanate, carbamoyl, epoxy, styrenyl, silyl, silyloxy, silanyl, siloxazanyl, boronato, boryl, or halogen, or a metal-containing or metalloid-containing group, where the metalloid is Sn or Ge, where the substituents may optionally provide a tether to an insoluble or sparingly soluble support media comprising alumina, silica, or carbon. In individual Aspects of this Embodiment, m is 0, m is 1, m is 2.

Embodiment 3

The method of Embodiment 1 or Embodiment 2, wherein the organosilane or organodisilane is an organosilane.

Embodiment 4

The method of Embodiment 1 or Embodiment 2, wherein the organosilane or organodisilane is an organodisilane.

Embodiment 5

The method of any one of Embodiments 1 to 3, wherein the organosilane comprises $(R)_3SiH$, $(R)_2SiH_2$, or $(R)SiH_3$, where R is independently at each occurrence optionally substituted $C_{1-18}$ alkoxy, optionally substituted $C_{1-18}$ alkyl, optionally substituted $C_{2-18}$ alkenyl, optionally substituted 6-18 ring membered aryl (i.e., containing 6-18 atoms in the ring system), 6-18 ring membered aryloxy, 5-18 ring membered heteroaryl, 6-18 ring membered aralkyl, 6-18 ring membered aralkyloxy, or 6-10 ring membered heteroaralkyl. In certain Aspects of this Embodiment, R is independently at each occurrence optionally substituted $C_{1-6}$ alkoxy, optionally substituted $C_{1-6}$ alkyl, optionally substituted $C_{2-6}$ alkenyl, optionally substituted optionally substituted phenyl, optionally substituted biphenyl, optionally substituted phenoxy, optionally substituted tolyl, optionally substituted benzyl (Bn), optionally substituted phenethyl, optionally substituted benzyloxy, optionally substituted pyridinyl (Py), optionally substituted pyridinylmethyl (Py-CH$_2$—), or optionally substituted pyridinylmethyl (Py-CH$_2$—O—). In certain Aspects of this Embodiment, the organosilane is Me$_3$SiH, EtMe$_2$SiH, Et$_2$MeSiH, Et$_3$SiH, (i-Pr)$_3$SiH, Bu$_3$SiH, PhMe$_2$SiH, Ph$_2$MeSiH, (EtO)$_3$SiH, Me$_2$(Py)SiH, (i-Pr)$_2$(Py)SiH, Me$_2$SiH$_2$, Et$_2$SiH$_2$, (i-Pr)$_2$SiH$_2$, (Bu)$_2$SiH$_2$, Ph$_2$SiH$_2$, or Bn$_2$SiH$_2$.

Embodiment 6

The method of any one of Embodiments 1, 2, or 4, wherein the organodisilane comprises $(R)_{3-m}(H)_m Si—Si(R)_{3-m}(H)_m$ or $(R)_3Si—Si(R)_3$, where R is independently at each occurrence optionally substituted $C_{1-18}$ alkoxy, optionally substituted $C_{1-18}$ alkyl, optionally substituted $C_{2-18}$ alkenyl, optionally substituted $C_{6-18}$ aryl, optionally substituted $C_{6-18}$ aryloxy, optionally substituted 5-18 ring membered heteroaryl, optionally substituted 6-18 ring membered aralkyl, optionally substituted 6-18 ring membered aralkyloxy, or optionally substituted 6-18 ring membered heteroaralkyl. In certain Aspects of this Embodiment, R is independently at each occurrence optionally substituted $C_{1-6}$ alkoxy, optionally substituted $C_{1-6}$ alkyl, optionally substituted $C_{2-6}$ alkenyl, optionally substituted optionally substituted phenyl, optionally substituted biphenyl, optionally substituted phenoxy, optionally substituted tolyl, optionally substituted tolyl, optionally substituted phenethyl, optionally substituted benzyloxy, optionally substituted pyridinyl, optionally substituted pyridinylmethyl (Py-CH$_2$—), or optionally substituted pyridinylmethyl (Py-CH$_2$—O—).

Embodiment 7

The method of one of Embodiments 1 to 6, wherein R is independently at each occurrence methyl, ethyl, propyl, butyl, propyl, phenyl, biphenyl, phenoxy, benzyl, benzyloxy, or pyridinyl. In certain Aspects of this Embodiment, these substituents are optionally substituted.

Embodiment 8

The method of any one of Embodiments 1 to 7, wherein the alkali metal hydroxide comprises sodium hydroxide (NaOH), potassium hydroxide (KOH), or a mixture thereof.

Embodiment 9

The method of any one of Embodiments 1 to 7, wherein the alkali metal alkoxide comprises a sodium alkoxide, potassium alkoxide, or mixture thereof.

Embodiment 10

The method of any one of Embodiments 1 to 9, wherein the alkoxide comprises a linear, branched, or cyclic saturated hydrocarbon group containing 1 to 12 carbon atoms.

Embodiment 11

The method of any one of Embodiments 1 to 10, wherein the alkoxide comprises sodium methoxide, sodium ethoxide, sodium n-propoxide, sodium isopropoxide, sodium n-butoxide, sodium sec-butoxide, sodium tert-butoxide, sodium n-pentoxide, sodium 2-pentoxide, sodium 3-pentoxide, sodium iso-pentoxide, potassium methoxide, potassium ethoxide, potassium n-propoxide, potassium isopropoxide, potassium n-butoxide, potassium sec-butoxide, potassium tert-butoxide, potassium n-pentoxide, potassium 2-pentoxide, potassium 3-pentoxide, or potassium iso-pentoxide.

Embodiment 12

The method of any one of Embodiments 1 to 9, wherein the least one organic substrate comprising the terminal olefin has a Formula (III):

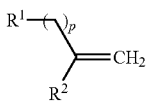
(III)

where p is 0 or 1; $R^1$ and $R^2$ independently comprises H, an optionally substituted $C_{1-18}$ alkyl, optionally substituted $C_{2-18}$ alkenyl, $C_{2-18}$ optionally substituted alkynyl, optionally substituted $C_{6-18}$ aryl, optionally substituted $C_{1-18}$ heteroalkyl, optionally substituted 5-6 ring membered heteroaryl, optionally substituted 5-6 ring membered aralkyl, optionally substituted 5-6 ring membered heteroaralkyl, or optionally substituted metallocene, provided that $R^1$ and $R^2$ are not both H.

Embodiment 13

The method of Embodiment 12, wherein each $R^1$ and $R^2$ independently is or comprises:
(a) an optionally substituted $C_{1-18}$ linear alkyl, an optionally substituted branched $C_{1-18}$ alkyl, or an optionally substituted $C_{3-18}$ cycloalkyl;
(b) an optionally substituted linear $C_{2-18}$ alkenyl, an optionally substituted branched $C_{2-18}$ alkenyl, or an optionally substituted $C_{3-18}$ cycloalkenyl;
(c) an optionally substituted linear $C_{1-18}$ heteroalkyl, an optionally substituted branched $C_{1-18}$ heteroalkyl, or an optionally substituted $C_{1-18}$ heterocycloalkyl;
(d) an optionally substituted 6-18 ring membered aryl, an optionally substituted 6-18 ring membered aralkyl, an optionally substituted 6-18 ring membered aryloxy, an optionally substituted 6-18 ring membered aralkyloxy, optionally substituted 5-18 ring membered heteroaryl, or an optionally substituted optionally substituted 5-18 ring membered heteroaralkyl, optionally substituted 5-18 ring membered heteroaryloxy, or an optionally substituted optionally substituted 5-18 ring membered heteroaralkyloxy; or
(e) hydrogen, provided that $R^1$ and $R^2$ are not both hydrogen when p=0.
In certain Aspects of this Embodiment, the optionally substituted aryl, aryloxy, arylalkyl, or arylalkyloxy comprises optionally substituted phenyl, biphenyl, phenoxy, benzyl, benzyloxy, naphthyl, or naphthyloxy. In certain Aspects of this Embodiment, the optionally substituted heteroaryl, heteroaryloxy, heteroarylalkyl, or heteroarylalkyloxy comprises an optionally substituted furan, pyrrole, thiophene, pyrazole, imidazole, triazole, isoxazole, oxazole, thiazole, isothiazole, oxadiazole, pyridine, pyridazine, pyrimidine, pyrazine, triazone, benzofuran, benzopyrrole, benzothiophene, isobenzofuran, isobenzopyrrole, isobenzothiophene, indole, isoindole, indolizine, indazole, azaindole, benzisoxazole, benzoxazole, quinoline, isoquinoline, cinnoline, quinazoline, naphthyridine, 2,3-dihydrobenzofuran, 2,3-dihydrobenzopyrrole, 2,3-dihydrobenzothiophene, dibenzofuran, xanthene, dibenzopyrol, or dibenzothiophene moiety.

Embodiment 14

The method of Embodiment 12 or 13, wherein the terminally silylated olefinic product has a Formula (IV) or (V):

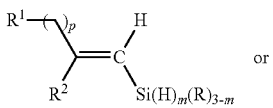
(IV)

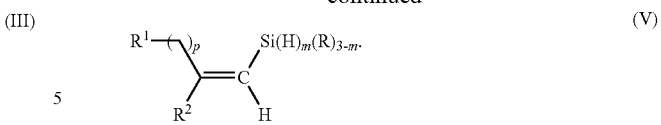
(V)

In other Aspects of this Embodiment, when p is 0 and either $R^1$ or $R^2$ is aromatic, the product of the reaction comprises a terminally silylated compound of the Formula (IX):

(IX)

resulting from the anti-Markovnikov addition of the organosilane to a vinyl aromatic substrate.

Embodiment 15

The method of any one of Embodiments 12 to 14, wherein when p=1, the terminally silylated olefinic product has a Formula (IV), (V), (VI), or (VII):

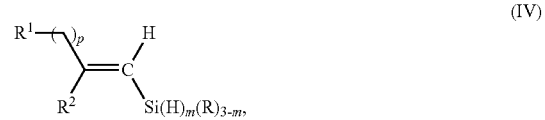
(IV)

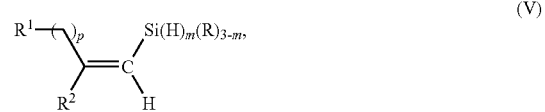
(V)

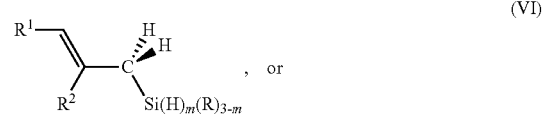
(VI)

, or

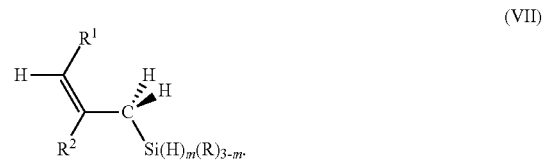
(VII)

In other Aspects of this Embodiment, when $R^2$ is aromatic, the product of the reaction comprises a terminally silylated compound of the Formula (VIII):

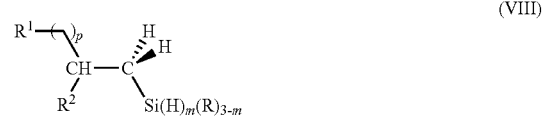
(VIII)

resulting from the anti-Markovnikov addition of the organosilane to a vinyl aromatic substrate.

Embodiment 16

The method of any one of Embodiments 1 to 15, wherein the method consists essentially of contacting at least one organic substrate comprising a terminal olefin with a mixture of an organosilane or organodisilane and an alkali metal alkoxide and/or an alkali metal hydroxide, such that the contacting results in the formation of a terminally silylated olefinic product or a terminally hydrosilylated product, the latter apparently favored when using vinyl aromatic substrates.

Embodiment 17

The method of any one of Embodiments 1 to 16, wherein the method is conducted in the absence of added transition metal ions or catalysts. In certain Aspects of this Embodiment, the method is conducted in the substantial absence of transition metal ions or catalysts (e.g., in some Aspects, less than 1%, 1000 ppm, 100 ppm, 50 ppm, or 10 ppm, based on the total weight of the system)

Embodiment 18

The method of any one of Embodiments 1 to 17, further comprising polymerizing the terminally silylated olefinic product Embodiment 19

The method of any one of Embodiments 2 to 18, where m is 1 or 2, further comprising reacting the terminally silylated olefinic product (or terminally hydrosilylated product), either isolated or in situ, with an aromatic substrate (including aryl and heteroaryl moieties) under conditions sufficient to silylate the aromatic substrate with the terminally silylated olefinic product (or terminally hydrosilylated product) to form a product of the silylation of the aromatic substrate with the terminally silylated olefinic product (or terminally hydrosilylated product). The conditions for and scope of such silylations can be found in U.S. Pat. No. 9,000,167, U.S. patent application Ser. No. 14/818,417, filed Aug. 5, 2015, and U.S. patent application Ser. No. 14/972,653, filed Dec. 17, 2015, each of which is incorporated by reference herein, at least for their teachings of the nature and conditions of the silylation reactions, the substrates the compositions used to prepare the same, and the products derived from the reactions.

Embodiment 20

The method of Embodiment 19, wherein the aromatic substrate comprises at least one of the following moieties:

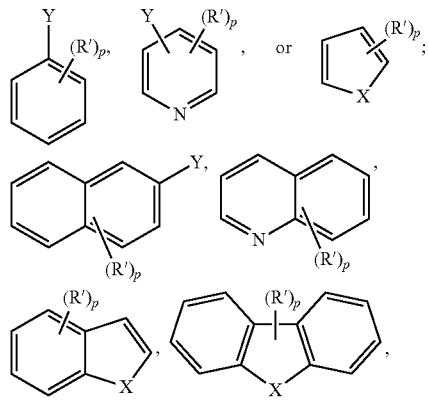

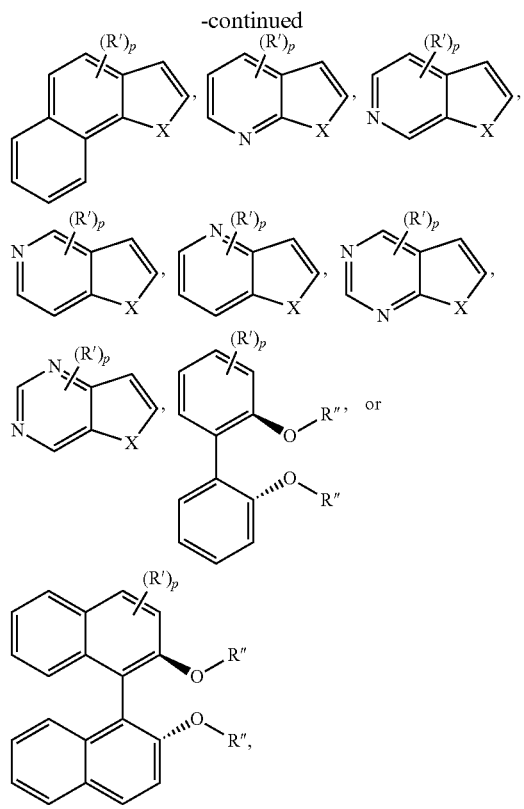

where X is N—R", O, or S;
Y is H, N(R")$_2$, O—R", or S—R"
p is 0 to 4, 0 to 3, 0 to 2, or 0 to 1;
R' is a functional group "Fn," as described above, or (R')$_p$ is an optionally substituted fused alicyclic, heteroalicyclic, aryl or heteroaryl moiety; and
R" is an amine protecting group or an optionally substituted alkyl, aryl, heteroaryl, alkaryl or alk-heteroaryl;
and wherein the terminally silylated olefinic product (or terminally hydrosilylated product) is introduced to the aromatic substrate on a 5 or 6-membered ring of the aromatic substrate.

In certain Aspects of this Embodiment, the aromatic substrate comprises an optionally substituted phenyl, biphenyl, phenoxy, benzyl, benzyloxy, naphthyl, or naphthyloxy moiety. In certain Aspects of this Embodiment, the aromatic substrate comprises an optionally substituted heteroaryl moiety. In certain Aspects of this Embodiment, the optionally substituted heteroaryl substrate comprises an optionally substituted furan, pyrrole, thiophene, pyrazole, imidazole, triazole, isoxazole, oxazole, thiazole, isothiazole, oxadiazole, pyridine, pyridazine, pyrimidine, pyrazine, triazone, benzofuran, benzopyrrole, benzothiophene, isobenzofuran, isobenzopyrrole, isobenzothiophene, indole, isoindole, indolizine, indazole, azaindole, benzisoxazole, benzoxazole, quinoline, isoquinoline, cinnoline, quinazoline, naphthyridine, 2,3-dihydrobenzofuran, 2,3-dihydrobenzopyrrole, 2,3-dihydrobenzothiophene, dibenzofuran, xanthene, dibenzopyrol, or dibenzothiophene moiety.

Embodiment 21

The method of any one of Embodiments 2 to 18, where m is 1 or 2, further comprising reacting the terminally silylated olefinic product (or terminally hydrosilylated product) (either isolated or in situ) with an organic substrate comprising a terminal alkyne, under conditions sufficient to form a silylated terminal alkynyl moiety so as to form a silylated terminal alkynyl moiety. The conditions for such silylations can be found in U.S. patent application Ser. No. 14/841,964, filed Sep. 1, 2015, which is incorporated by reference herein in its entirety for its teachings of the nature and conditions of the silylation reactions, the substrates, the compositions used to prepare the same, and the products derived from the reactions.

Embodiment 22

The method of Embodiment 21, wherein the organic substrate comprising the terminal alkynyl C—H bond has a formula:

$$R^3-C\equiv C-H$$

where $R^3$ comprises H, an optionally substituted $C_{1-18}$ alkyl, optionally substituted $C_{2-18}$ alkenyl, optionally substituted $C_{2-18}$ alkynyl, optionally substituted $C_{1-18}$ membered heteroalkyl, optionally substituted 6-18 ring membered aryl, optionally substituted 6-18 ring membered aryloxy, optionally substituted 6-18 ring membered aralkyl, optionally substituted 6-18 ring membered aralkyloxy, optionally substituted 5-18 ring membered heteroaryl, optionally substituted 5-18 ring membered heteroaryloxy, optionally substituted 5-18 ring membered heteroarylalkyl, optionally substituted 5-18 ring membered heteroaralkyloxy, or optionally substituted metallocene. In certain Aspects of this Embodiment, the aromatic substrate comprises an optionally substituted phenyl, biphenyl, phenoxy, benzyl, benzyloxy, naphthyl, or naphthyloxy moiety. In certain Aspects of this Embodiment, the aromatic substrate comprises an optionally substituted heteroaryl moiety. In certain of these Aspects, the heteroalkyl moiety comprises an optionally substituted furan, pyrrole, thiophene, pyrazole, imidazole, triazole, isoxazole, oxazole, thiazole, isothiazole, oxadiazole, pyridine, pyridazine, pyrimidine, pyrazine, triazone, benzofuran, benzopyrrole, benzothiophene, isobenzofuran, isobenzopyrrole, isobenzothiophene, indole, isoindole, indolizine, indazole, azaindole, benzisoxazole, benzoxazole, quinoline, isoquinoline, cinnoline, quinazoline, naphthyridine, 2,3-dihydrobenzofuran, 2,3-dihydrobenzopyrrole, 2,3-dihydrobenzothiophene, dibenzofuran, xanthene, dibenzopyrol, or dibenzothiophene moiety.

Embodiment 23

The method of any one of Embodiments 2 to 18, where m is 0, 1, or 2 further comprising reacting the terminally silylated olefinic product (either isolated or in situ) with:

(a) water, alcohol, hydrogen cyanide, hydrogen chloride, dihalogen, or carboxylic acid under conditions known to give corresponding hydroxy, alkoxy, cyano, halo, or ester products;

(b) alkyl and aryl/heteroaryl halides, in the presence of palladium catalysts, under cross-coupling conditions sufficient to replace the silyl group by the corresponding alkyl and aryl/heteroaryl moiety;

(c) alkyl lithium or potassium tert-butoxide, then with an alkyl halide to form a alkyl substituted vinyl silyl product;

(d) ICl or $I_2$ so as to form a terminal vinyl iodide (with the displacement of the silyl group);

(e) a polyolefin (for example, polyethylene) so as to form a silane grafted polyolefin;

(f) an organic peroxide (for example m-CPBA) to form a terminal silylated peroxide, which when treated with a strong acid (e.g., perchloric acid, formic acid, or TFA) forms an aldehyde moiety;

(g) a fluoride source, hydrogen peroxide, and base to form an aldehyde or ketone, according to the well-known Tamao-Fleming Oxidation reaction;

(h) an iodosyl benzene to form a vinyliodonium tetrafluoroborate; or (i) an acid chloride, aldehyde, epoxide, imine, ketal, or ketone, with a Lewis acid, for example $TiCl_4$ or $BF_3*OEt_2$, under conditions generally recognized as associated with the Hosomi-Sakurai Allylation reaction to form the corresponding allyl derivative.

In other such Aspects of this Embodiments, the

Embodiment 24

A composition comprising a mixture of:

(a) an organic substrate comprising a terminal olefin:

(b) an organosilane, an organodisilane, or a mixture thereof and (c) an alkali metal alkoxide, an alkali metal hydroxide, or a mixture thereof.

In certain Aspects of this Embodiment, the composition comprises any mixture used in or derived from a method of any one of Embodiments 1-23.

Embodiment 25

The composition of claim 24, wherein the organosilane has a structure of Formula (I) and the organodisilane has a structure of Formula (II):

$$(R)_{3-m}Si(H)_{m+1} \tag{I}$$

$$(R)_{3-m}(H)_m Si-Si(R)_{3-m}(H)_m \tag{II}$$

where: m is independently 0, 1, or 2; and each R is independently optionally substituted $C_{1-24}$ alkyl or heteroalkyl, optionally substituted $C_{2-24}$ alkenyl or heteroalkenyl, optionally substituted $C_{2-24}$ alkynyl or heteroalkynyl, optionally substituted 5 to 12 ring membered aryl or 5 to 12 ring membered heteroaryl, optionally substituted 5 to 12 ring-membered alkaryl or 5 to 12 ring-membered heteroalkaryl, optionally substituted 5 to 12 ring-membered aralkyl or 5 to 12 ring-membered heteroaralkyl, optionally substituted —O—$C_{1-24}$ alkyl or heteroalkyl, optionally substituted 5 to 12 ring-membered aryloxy or 5 to 12 ring-membered heteroaryloxy, optionally substituted 5 to 12 ring-membered alkaryloxy or 5 to 12 ring-membered heteroalkaryloxy, or optionally substituted 5 to 12 ring-membered aralkoxy or 5 to 12 ring-membered heteroaralkoxy, and, if substituted, the substituents may be phosphonato, phosphoryl, phosphanyl, phosphino, sulfonato, $C_1$-$C_{20}$ alkylsulfanyl, $C_5$-$C_{20}$ arylsulfanyl, $C_1$-$C_{20}$ alkylsulfonyl, $C_5$-$C_{20}$ arylsulfonyl, $C_1$-$C_{20}$ alkylsulfinyl, 5 to 12 ring-membered arylsulfinyl, sulfonamido, amino, amido, imino, nitro, nitroso, hydroxyl, $C_1$-$C_{20}$ alkoxy, $C_5$-$C_{20}$ aryloxy, $C_2$-$C_{20}$ alkoxycarbonyl, $C_5$-$C_{20}$ aryloxycarbonyl, carboxyl, carboxylato, mercapto, formyl, $C_1$-$C_{20}$ thioester, cyano, cyanato, thiocyanato, isocyanate, thioisocyanate, carbamoyl, epoxy, styrenyl, silyl, silyloxy, silanyl, siloxazanyl, boronato, boryl, or halogen, or a metal-containing or metalloid-containing group, where the metalloid is Sn or Ge, where the substituents may optionally provide a tether to an insoluble or sparingly soluble support media comprising alumina, silica, or carbon.

Embodiment 26

The composition of Embodiment 24 or Embodiment 25, wherein the organosilane or organodisilane is an organosilane.

Embodiment 27

The composition of Embodiment 24 or Embodiment 25, wherein the organosilane or organodisilane is an organodisilane.

Embodiment 28

The composition of any one of Embodiments 24 to 26, wherein the organosilane comprises a compound of formula $(R)_3SiH$, $(R)_2SiH_2$, or $(R)SiH_3$, where R is independently at each occurrence alkoxy, alkyl, alkenyl, aryl, aryloxy, heteroaryl, aralkyl, or heteroaralkyl.

Embodiment 29

The composition of any one of Embodiments 24, 25, or 27, wherein the organodisilane comprises a compound of formula $(R)_3Si—Si(R)_3$, where R is independently $C_{1-6}$ alkoxy, $C_{1-6}$ alkyl, $C_{2-6}$ alkenyl, $C_{6-10}$ aryl, $C_{6-10}$ aryloxy, a 5-9 ring membered heteroaryl, a 6-10 ring membered aralkyl, or 5-9 ring membered heteroaralkyl.

Embodiment 30

The composition of one of Embodiments 24 to 29, wherein R is independently at each occurrence methyl, ethyl, propyl, butyl, propyl, phenyl, or pyridinyl.

Embodiment 31

The composition of any one of Embodiments 24 to 30, wherein the alkali metal hydroxide comprises sodium hydroxide (NaOH), potassium hydroxide (KOH) or a mixture thereof.

Embodiment 32

The composition of any one of Embodiments 24 to 30, wherein the alkali metal alkoxide comprises sodium alkoxide, potassium alkoxide or a mixture thereof.

Embodiment 33

The composition of any one of Embodiments 24 to 32, wherein the alkoxide comprises a linear, branched, or cyclic saturated hydrocarbon group containing 1 to 12 carbon atoms.

Embodiment 34

The composition of any one of Embodiments 24 to 33, wherein the alkali metal alkoxide comprises sodium methoxide, sodium ethoxide, sodium n-propoxide, sodium isopropoxide, sodium n-butoxide, sodium sec-butoxide, sodium tert-butoxide, sodium n-pentoxide, sodium 2-pentoxide, sodium 3-pentoxide, sodium iso-pentoxide, potassium methoxide, potassium ethoxide, potassium n-propoxide, potassium isopropoxide, potassium n-butoxide, potassium sec-butoxide, potassium tert-butoxide, potassium n-pentoxide, potassium 2-pentoxide, potassium 3-pentoxide, or potassium iso-pentoxide.

Embodiment 35

The composition of any one of Embodiments 24 to 34, wherein the organic substrate comprising the terminal olefin has a Formula (III):

$$R^1\!-\!(\ )_p\!\!\underset{R^2}{\diagdown}\!=\!CH_2 \quad (III)$$

where p is 0 or 1; $R^1$ and $R^2$ independently comprises H, an optionally substituted alkyl, optionally substituted heteroalkyl, optionally substituted alkenyl, optionally substituted alkynyl, optionally substituted aryl, optionally substituted aryloxy, optionally substituted aralkyl, optionally substituted aralkyloxy, optionally substituted heteroaryl, optionally substituted heteroarylalkyl, optionally substituted heteroaralkyloxy, optionally substituted heteroaralkyloxy, or optionally substituted metallocene, provided that $R^1$ and $R^2$ are not both H.

Embodiment 36

The composition of Embodiment 35, wherein $R^1$ and $R^2$ independently is or comprises:

(a) an optionally substituted $C_{1-18}$ linear alkyl, an optionally substituted branched $C_{1-18}$ alkyl, or an optionally substituted $C_{3-18}$ cycloalkyl;

(b) an optionally substituted linear $C_{2-18}$ alkenyl, an optionally substituted branched $C_{2-18}$ alkenyl, or an optionally substituted $C_{3-18}$ cycloalkenyl;

(c) an optionally substituted linear $C_{1-18}$ heteroalkyl, optionally substituted branched $C_{1-18}$ heteroalkyl, or an optionally substituted $C_{1-18}$ heterocycloalkyl;

(d) an optionally substituted 6-18 ring membered aryl, an optionally substituted 6-18 ring membered aralkyl, an optionally substituted 6-18 ring membered aryloxy, an optionally substituted 6-18 ring membered aralkyloxy, optionally substituted 5-18 ring membered heteroaryl, or an optionally substituted optionally substituted 5-18 ring membered heteroaralkyl, optionally substituted 5-18 ring membered heteroaryloxy, or an optionally substituted optionally substituted 5-18 ring membered heteroaralkyloxy; or (e) hydrogen, provided that $R^1$ and $R^2$ are not both hydrogen when p=0.

In certain Aspects of this Embodiment, the optionally substituted aryl, aryloxy, arylalkyl, or arylalkyloxy comprises optionally substituted phenyl, phenoxy, benzyl, benzyloxy, naphthyl, or naphthyloxy. In certain Aspects of this Embodiment, the optionally substituted heteroaryl, heteroaryloxy, heteroarylalkyl, or heteroarylalkyloxy comprises an optionally substituted furan, pyrrole, thiophene, pyrazole, imidazole, triazole, isoxazole, oxazole, thiazole, isothiazole, oxadiazole, pyridine, pyridazine, pyrimidine, pyrazine, triazone, benzofuran, benzopyrrole, benzothiophene, isobenzofuran, isobenzopyrrole, isobenzothiophene, indole, isoindole, indolizine, indazole, azaindole, benzisoxazole, benzoxazole, quinoline, isoquinoline, cinnoline, quinazoline, naphthyridine, 2,3-dihydrobenzofuran, 2,3-dihydrobenzopyrrole, 2,3-dihydrobenzothiophene, dibenzofuran, xanthene, dibenzopyrol, or dibenzothiophene moiety.

Embodiment 37

The composition of Embodiment 35 or 36, further comprising a terminally silylated olefinic product having a Formula (IV) or (V):

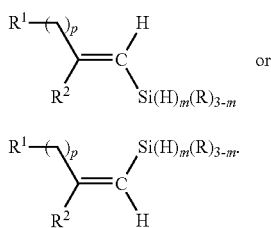

In other Aspects of this Embodiment, when p is 0 and either R$^1$ or R$^2$ is aromatic, the composition may further comprise a terminally silylated compound of the Formula (IX):

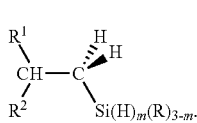

Embodiment 38

The composition of any one of Embodiments 35 to 37, wherein when p=1, further comprising a terminally silylated olefinic product having a Formula (IV), (V), (VI), or (VII):

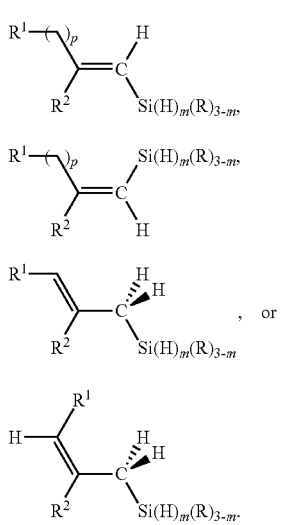

In other Aspects of this Embodiment, when R$^2$ is aromatic, the composition may further comprise a terminally silylated compound of the Formula (VIII):

Embodiment 39

The composition of any one of Embodiments 24 to 38, wherein the composition contains no added transition metal ions or transition metal catalysts otherwise capable of effecting the silylation of terminal olefins in a reaction where the reaction product is a terminally silylated olefinic product.

Embodiment 40

The composition of any one of Embodiments 24 to 39, wherein the composition is substantially free of transition metal ions or transition metal catalysts otherwise capable of effecting the silylation of terminal olefins in a reaction where the reaction product is a terminally silylated olefinic product. In other Aspects of this Embodiment, the composition is substantially free of transition metal ions or transition metal catalysts otherwise capable of effecting the silylation of an aromatic vinyl compound in a reaction where the reaction product is a terminally hydrosilylated product.

EXAMPLES

The following Examples are provided to illustrate some of the concepts described within this disclosure. While each Example is considered to provide specific individual embodiments of composition, methods of preparation and use, none of the Examples should be considered to limit the more general embodiments described herein.

In the following examples, efforts have been made to ensure accuracy with respect to numbers used (e.g. amounts, temperature, etc.) but some experimental error and deviation should be accounted for. Unless indicated otherwise, temperature is in degrees C., pressure is at or near atmospheric.

Example 1: General Information

Unless otherwise stated, reactions were performed in oven-dried brand-new Fisher brand scintillation vials in a nitrogen filled glove box or in flame-dried Schlenk flasks under argon connected on a Schlenk line using dry, degassed solvents and brand-new stirring bars. Solvents were dried by passage through an activated alumina column under argon. $^1$H NMR spectra were recorded on a Varian Inova 500 MHz spectrometer in CDCl$_3$ or THF-d8. $^{13}$C NMR spectra were recorded on a Varian Inova 500 MHz spectrometer (126 MHz) in CDCl$_3$ or THF-d8. GC-FID analyses were obtained on an Agilent 6890N gas chromatograph equipped with a HP-5 (5%-phenyl)-methylpolysiloxane capillary column (Agilent). GC-MS analyses were obtained on an Agilent 6850 gas chromatograph equipped with a HP-5 (5%-phenyl)-methylpolysiloxane capillary column (Agilent). High resolution mass spectra (HRMS) were acquired from the California Institute of Technology Mass Spectrometry Facility. ICP-MS analysis was conducted at the California Institute of Technology Mass Spectrometry Facility.

Organosilanes and organodisilanes were purchased from Aldrich and distilled before use. KOt-Bu was purchased from Aldrich (sublimed grade, 99.99% trace metals basis)

and used directly. KOH was purchased from Aldrich (semiconductor grade, pellets, 99.99% trace metals basis) and was pulverized (mortar and pestle) and heated (150° C.) under vacuum prior to use. NaOH was purchased from Aldrich (semiconductor grade, pellets, 99.99% trace metals basis) and was pulverized (mortar and pestle) and heated (150° C.) under vacuum prior to use.

Example 2: Representative Reactions

Example 2.1: Reaction Conditions

General reaction procedure: In a nitrogen-filled glovebox, catalyst (KOtBu, 0.5 equiv.) was measured into an oven-dried 2 mL glass vial. The olefin substrate (1.0 equiv) was then added to the vial. Solvent (DME, to make a 1 M concentration of olefin in DME) and silane (3.0 equiv) are then added, a teflon stir-bar is placed into the vial, and the reaction is sealed and stirred for 24-96 h at temperatures ranging from 45-150° C. The reaction was quenched by diluting with diethyl ether; the solution was filtered through a short plug of silica then concentrated under reduced pressure. Purification by column chromatography afforded the pure compounds detailed below. The yield was determined by $^1$H NMR or GC-FID analysis of the crude mixture using an internal standard. Cis-/trans-ratios were determined by NMR or GC-FID.

Example 2.2: Screening Experiments—1-Dodecene with Triethylsilane

A series of screening experiments were conducted using 1-dodecene and triethylsilane, so as to evaluate a range of conditions on the organosilylation reactions. The results for screening reactions done to evaluate the effects of various bases are shown in Table 1.

TABLE 1

Screening experiments with 1-dodecene and various bases using 0.2 eq base, 3 eq Et$_3$SiH, 0.1 mL 1,2-dimethoxy ethane at 45° C. for 48 h.

$$C_9H_{19}\diagup\!\!\!= \quad \longrightarrow \quad C_9H_{19}\diagup\!\!\!\diagdown\!\!\!\diagup SiEt_3 \quad + \quad C_9H_{19}\diagup\!\!\!\diagdown^{SiEt_3} \quad + \quad C_9H_{19}\diagup\!\!\!\diagdown\!\!\!\diagup SiEt_3$$

| | 1 | 2a | 2b | 2c |

| Base | Conversion (%) | Yield 2a (%) | Yield 2b (%) | Yield 2c (%) | E:Z Ratio | Vinyl:Allyl Ratio |
|---|---|---|---|---|---|---|
| KOt-Bu | 46.0 | 22.8 | 14.2 | 7.6 | 1.61 | 4.85 |
| KH | 1.7 | 0.1 | 0.5 | 0.0 | 0.20 | — |
| KHMDS | 15.9 | 5.4 | 8.8 | 1.1 | 0.61 | 13.04 |
| NaOt-Bu | 0.6 | 0.0 | 0.0 | 0.0 | — | — |
| LiOt-Bu | 0.3 | 0.0 | 0.0 | 0.0 | — | — |
| DABCO | 0.2 | 0.0 | 0.0 | 0.0 | — | — |
| NaOEt | 3.1 | 0.1 | 2.5 | 0.0 | 0.03 | — |
| KOEt | 24.4 | 9.1 | 12.0 | 2.8 | 0.76 | 7.42 |
| NaOAc | 0.3 | 0.0 | 0.0 | 0.0 | — | — |
| KOAc | 0.6 | 0.0 | 0.0 | 0.0 | — | — |
| KOMe | 16.1 | 1.8 | 13.4 | 0.4 | 0.13 | 37.83 |
| NaOMe | 5.8 | 0.0 | 0.0 | 0.0 | — | — |
| Cs$_2$O$_3$ | 0.3 | 0.0 | 0.0 | 0.0 | — | — |
| K$_2$CO$_3$ | 3.0 | 0.0 | 0.0 | 0.0 | — | — |
| KOt-Amyl | 41.0 | 19.9 | 13.0 | 6.3 | 1.53 | 5.18 |
| KOH | 14.4 | 1.2 | 12.1 | 0.4 | 0.10 | 36.20 |
| TMAF | 0.7 | 0.0 | 0.0 | 0.0 | 0.00 | — |
| KF | 0.3 | 0.0 | 0.0 | 0.0 | — | — |
| NaOH | 1.2 | 0.1 | 0.3 | 0.0 | 0.15 | — |
| LiOH | 0.3 | 0.0 | 0.0 | 0.0 | — | — |
| Et$_3$N | 0.3 | 0.0 | 0.0 | 0.0 | — | — |
| Pyridine | 0.1 | 0.0 | 0.0 | 0.0 | — | — |
| CsF | 0.4 | 0.0 | 0.0 | 0.0 | — | — |
| None | 0.0 | 0.0 | 0.0 | 0.0 | — | — |

Note that the conversion of starting material is greater than the total amount of silylated products due to slight production of isomerized 1-dodecene.

The results for screening reactions done to evaluate the effects of various bases at different temperatures are shown in Table 2 and Table 3. Potassium salts appeared to be favored, at least under the conditions tested here.

TABLE 2

Screening experiments with 1-dodecene and various bases using 0.2 eq base, 3 eq Et$_3$SiH, 0.1 mL DME at 65° C. for 48 h.

C$_9$H$_{19}$–CH=CH$_2$ (1) → C$_9$H$_{19}$–CH=CH–SiEt$_3$ (2a) + C$_9$H$_{19}$–CH(SiEt$_3$)=CH$_2$ (2b) + C$_9$H$_{19}$–CH=CH–CH$_2$–SiEt$_3$ (2c)

| Base | Conversion (%) | Yield 2a (%) | Yield 2b (%) | Yield 2c (%) | E:Z Ratio | Vinyl:Allyl Ratio |
|---|---|---|---|---|---|---|
| KOt-Bu | 46.5 | 24.8 | 14.2 | 7.5 | 1.74 | 5.23 |
| KHMDS | 15.9 | 7.7 | 6.9 | 1.2 | 1.11 | 12.05 |
| KOEt | 25.3 | 12.0 | 10.6 | 2.6 | 1.13 | 8.64 |
| KOMe | 9.3 | 1.9 | 7.4 | 0.1 | 0.25 | 109.66 |
| KOt-Amyl | 43.7 | 23.1 | 13.7 | 6.9 | 1.69 | 5.34 |
| KOH | 11.7 | 3.6 | 7.7 | 0.4 | 0.47 | 29.55 |
| NaOt-Bu | 0.0 | 0.0 | 0.0 | 0.0 | — | — |
| LiOt-Bu | 0.0 | 0.0 | 0.0 | 0.0 | — | — |

TABLE 3

Screening experiments with 1-dodecene and various bases using 0.2 eq base, 3 eq Et$_3$SiH, 0.1 mL DME at 45° C. for 48 h, then 65° C. for 48 h,.

C$_9$H$_{19}$–CH=CH$_2$ (1) → C$_9$H$_{19}$–CH=CH–SiEt$_3$ (2a) + C$_9$H$_{19}$–CH(SiEt$_3$)=CH$_2$ (2b) + C$_9$H$_{19}$–CH=CH–CH$_2$–SiEt$_3$ (2c)

| Base | Conversion (%) | Yield 2a (%) | Yield 2b (%) | Yield 2c (%) | E:Z Ratio | Vinyl:Allyl Ratio |
|---|---|---|---|---|---|---|
| KOt-Bu | 58.9 | 30.8 | 15.6 | 9.2 | 1.97 | 5.02 |
| KHMDS | 14.5 | 4.5 | 5.5 | 0.8 | 0.82 | 12.37 |
| KOEt | 34.2 | 16.4 | 12.4 | 4.3 | 1.32 | 6.75 |
| KOMe | 33.1 | 9.5 | 12.5 | 1.5 | 0.76 | 14.51 |
| KOt-Amyl | 56.1 | 29.2 | 15.0 | 8.8 | 1.95 | 4.99 |
| KOH | 16.6 | 4.9 | 9.8 | 0.6 | 0.50 | 23.87 |
| NaOt-Bu | 2.3 | 0.0 | 0.3 | 0.2 | 0.10 | 1.75 |
| LiOt-Bu | 0.6 | 0.0 | 0.0 | 0.0 | — | — |

The results for screening reactions done to evaluate the effects of various solvents are shown in Table 4. Ethers tended to be favored, at least under the conditions of these experiments.

TABLE 4

Screening experiments with 1-dodecene and various bases using 0.2 eq base, 3 eq Et$_3$SiH, 0.1 mL solvent at 45° C. for 48 h, then 65° C. for 48 h,.

C$_9$H$_{19}$–CH=CH$_2$ (1) → C$_9$H$_{19}$–CH=CH–SiEt$_3$ (2a) + C$_9$H$_{19}$–CH(SiEt$_3$)=CH$_2$ (2b) + C$_9$H$_{19}$–CH=CH–CH$_2$–SiEt$_3$ (2c)

| Base | Solvent | Conversion (%) | Yield 2a (%) | Yield 2b (%) | Yield 2c (%) | E:Z Ratio | Vinyl:Allyl Ratio |
|---|---|---|---|---|---|---|---|
| KOt-Bu | Neat | 5.7 | 0.0 | 0.0 | 0.1 | — | 0.00 |
|  | THF | 71.7 | 36.2 | 19.4 | 8.7 | 1.87 | 6.42 |
|  | Dioxane | 5.9 | 0.0 | 0.0 | 0.0 | — | — |
|  | DME | 82.5 | 40.5 | 19.6 | 10.9 | 2.07 | 5.53 |
|  | MTBE | 12.0 | 1.7 | 2.5 | 0.2 | 0.68 | 19.62 |
|  | Toluene | 6.5 | 0.0 | 0.0 | 0.0 | — | — |
|  | CyMe | 8.1 | 0.0 | 0.0 | 0.0 | — | — |
|  | MeCN | 0.0 | 0.0 | 0.0 | 0.0 | — | — |

TABLE 4-continued

Screening experiments with 1-dodecene and various bases using 0.2 eq base, 3 eq Et₃SiH, 0.1 mL solvent at 45° C. for 48 h, then 65° C. for 48 h,.

$$C_9H_{19}\text{-CH=CH}_2 \longrightarrow C_9H_{19}\text{-CH=CH-SiEt}_3 \; (2a) \; + \; C_9H_{19}\text{-CH=CH(SiEt}_3) \; (2b) \; + \; C_9H_{19}\text{-CH=CH-CH}_2\text{SiEt}_3 \; (2c)$$

| Base | Solvent | Conversion (%) | Yield 2a (%) | Yield 2b (%) | Yield 2c (%) | E:Z Ratio | Vinyl:Allyl Ratio |
|---|---|---|---|---|---|---|---|
| | Mesitylene | 5.7 | 0.0 | 0.0 | 0.0 | — | — |
| | DCM | 14.3 | 0.0 | 0.0 | 0.0 | — | — |
| | Et₂O | 12.0 | 1.8 | 2.6 | 0.3 | 0.70 | 16.66 |
| | Benzene | 7.0 | 0.0 | 0.0 | 0.0 | — | — |
| | 2-Me THF | 8.0 | 0.5 | 1.0 | 0.0 | 0.53 | — |
| KOMe | Neat | 8.7 | 0.0 | 0.0 | 0.0 | — | — |
| | THF | 19.0 | 2.6 | 9.1 | 0.3 | 0.29 | 45.07 |
| | Dioxane | 4.1 | 0.0 | 0.0 | 0.0 | — | — |
| | DME | 33.1 | 9.5 | 12.5 | 1.5 | 0.76 | 14.51 |
| | MTBE | 0.0 | 0.0 | 0.0 | 0.0 | — | — |
| | Toluene | 0.0 | 0.0 | 0.0 | 0.0 | — | — |
| | CyMe | 12.0 | 0.0 | 0.0 | 0.0 | — | — |
| | MeCN | 0.0 | 0.0 | 0.0 | 0.0 | — | — |
| | Mesitylene | 7.6 | 0.0 | 0.0 | 0.0 | — | — |
| | DCM | 0.0 | 0.0 | 0.0 | 0.0 | — | — |
| | Et₂O | 8.1 | 0.0 | 0.0 | 0.0 | — | — |
| | Benzene | 14.5 | 0.0 | 0.0 | 0.0 | — | — |
| | 2-Me THF | 7.9 | 0.0 | 0.0 | 0.0 | — | — |

The results for screening reactions done to evaluate the effects of various solvents are shown in Table 5. DMF tended to reduce the activity of the reaction manifold, at least under the conditions of these experiments. It is not clear whether such inhibition is a general attribute of amides.

TABLE 5

The effect of dimethylformamide (DMF) as a solvent. Addition of DMF: 0.2 eq base, 3 eq Et3SiH, 0.1 mL DMF + DME at 45° C. for 48 h then 65° C. for 48 h.

$$C_9H_{19}\text{-CH=CH}_2 \longrightarrow C_9H_{19}\text{-CH=CH-SiEt}_3 \; (2a) \; + \; C_9H_{19}\text{-CH=CH(SiEt}_3) \; (2b) \; + \; C_9H_{19}\text{-CH=CH-CH}_2\text{SiEt}_3 \; (2c)$$

| Base | DMF (%) | Conversion (%) | Yield 2a (%) | Yield 2b (%) | Yield 2c (%) | E:Z Ratio | Vinyl:Allyl Ratio |
|---|---|---|---|---|---|---|---|
| KOt-Bu | 100 | 25.6 | 0.0 | 0.3 | 0.0 | 0.00 | — |
| | 80 | 84.5 | 0.0 | 1.1 | 0.0 | 0.00 | — |
| | 60 | 16.9 | 0.0 | 0.0 | 0.0 | — | — |
| | 50 | 53.0 | 0.0 | 3.2 | 0.2 | 0.00 | 15.63 |
| | 40 | 13.2 | 0.0 | 0.0 | 0.0 | — | — |
| | 20 | 9.3 | 0.0 | 0.0 | 0.0 | — | — |
| | 10 | 92.1 | 0.1 | 12.2 | 0.4 | 0.01 | 31.45 |
| | 0 | 81.7 | 17.0 | 31.3 | 3.5 | 0.54 | 13.92 |
| KOMe | 100 | 8.7 | 0.0 | 0.0 | 0.0 | — | — |
| | 80 | 9.8 | 0.0 | 0.0 | 0.0 | — | — |
| | 60 | 8.0 | 0.0 | 0.0 | 0.0 | — | — |
| | 50 | 7.5 | 0.0 | 0.0 | 0.0 | — | — |
| | 40 | 9.2 | 0.0 | 0.0 | 0.0 | — | — |
| | 20 | 8.2 | 0.0 | 0.0 | 0.0 | — | — |
| | 10 | 8.5 | 0.0 | 0.0 | 0.0 | — | — |
| | 0 | 15.5 | 2.5 | 6.3 | 0.2 | 0.40 | 43.40 |

The results for screening reactions done to evaluate the effects of various base loadings for KO-t-Bu are shown in Table 6.

TABLE 6

Screening experiments with 1-dodecene and various bases using 0.2 eq base, 3 eq Et$_3$SiH, 0.1 mL solvent at 45° C. for 48 h, then 65° C. for 48 h,.

C$_9$H$_{19}$–CH=CH$_2$ (1) → C$_9$H$_{19}$–CH=CH–CH$_2$–SiEt$_3$ (2a) + C$_9$H$_{19}$–CH$_2$–CH=CH(SiEt$_3$) (2b) + C$_9$H$_{19}$–CH=CH–CH$_2$–SiEt$_3$ (2c)

| Base | Conversion (%) | Yield 2a (%) | Yield 2b (%) | Yield 2c (%) | E:Z Ratio | Vinyl:Allyl Ratio |
|---|---|---|---|---|---|---|
| 100 mol % | 91.7 | 36.4 | 28.8 | 9.4 | 1.27 | 6.97 |
| 50 mol % | 86.2 | 40.4 | 22.7 | 10.7 | 1.78 | 5.90 |
| 40 mol % | 75.2 | 39.8 | 18.0 | 11.1 | 2.21 | 5.20 |
| 30 mol % | 52.1 | 27.2 | 14.1 | 8.4 | 1.92 | 4.90 |
| 20 mol % | 44.1 | 22.4 | 13.5 | 6.7 | 1.66 | 5.37 |
| 10 mol % | 29.4 | 12.6 | 10.4 | 5.4 | 1.21 | 4.28 |
| 5 mol % | 14.7 | 3.0 | 9.9 | 0.3 | 0.31 | 39.30 |
| 1 mol % | 16.7 | 3.8 | 11.1 | 0.5 | 0.34 | 30.77 |

Screening reactions were done to evaluate the effects of pre-conditioning the catalyst system on reactivity of the system. Little to no effect was observed, at least under the reaction conditions shown in Table 7.

TABLE 7

Effect of pre-conditioning the the catalyst, silane, and solvent: 50 mol % KOtBu, 3 eq Et$_3$SiH, 0.1 mL DME at 45° C. for 48 h then 65° C. for 48 h.

C$_9$H$_{19}$–CH=CH$_2$ (1) → C$_9$H$_{19}$–CH=CH–CH$_2$–SiEt$_3$ (2a) + C$_9$H$_{19}$–CH$_2$–CH=CH(SiEt$_3$) (2b) + C$_9$H$_{19}$–CH=CH–CH$_2$–SiEt$_3$ (2c)

| Pre-Stirring Time | Conversion (%) | Yield 2a (%) | Yield 2b (%) | Yield 2c (%) | E:Z Ratio | Vinyl:Allyl Ratio |
|---|---|---|---|---|---|---|
| 0 h | 45.3 | 21.0 | 14.3 | 8.1 | 1.47 | 4.35 |
| 0.5 h | 42.2 | 19.7 | 13.4 | 7.3 | 1.47 | 4.50 |
| 1 h | 43.1 | 20.1 | 13.6 | 7.6 | 1.47 | 4.42 |
| 2 h | 43.9 | 21.1 | 13.6 | 7.4 | 1.55 | 4.69 |
| 4 h | 43.9 | 20.5 | 13.9 | 7.8 | 1.48 | 4.38 |
| 6 h | 41.6 | 19.5 | 13.3 | 7.1 | 1.47 | 4.61 |
| 8 h | 40.5 | 18.5 | 13.2 | 7.2 | 1.41 | 4.42 |
| 12 h | 34.7 | 15.5 | 12.0 | 5.9 | 1.30 | 4.67 |
| 24 h | 37.0 | 17.0 | 12.4 | 6.3 | 1.37 | 4.69 |

Screening reactions were done to evaluate the effects of added potassium salts on the reactivity of the catalyst system. The results shown in Little to no effect was observed, at least under the reaction conditions shown in Table 8 suggest that the addition of potassium salts do not help the reaction performance, nor do they help an organic nucleophilic base (DABCO) catalyze this reaction, at least under the conditions tested.

TABLE 7

Effect of potassium salts on reactivity: 50 mol % KOtBu, 3 eq Et$_3$SiH, 0.1 mL DME at 45° C. for 48 h then 65° C. for 48 h.

$C_9H_{19}$—CH=CH$_2$ (1) → $C_9H_{19}$—CH=CH—SiEt$_3$ (2a) + $C_9H_{19}$—C(SiEt$_3$)=CH—... (2b) + $C_9H_{19}$—CH=CH—CH$_2$SiEt$_3$ (2c)

| Salt, Amount | Conversion (%) | Yield 2a (%) | Yield 2b (%) | Yield 2c (%) | E:Z Ratio | Vinyl:Allyl Ratio |
|---|---|---|---|---|---|---|
| none | 74.5 | 39.5 | 18.9 | 10.5 | 2.09 | 5.54 |
| KCl, 0.5 eq | 73.6 | 39.1 | 18.6 | 10.5 | 2.10 | 5.52 |
| KCl, 1.0 eq | 71.7 | 38.0 | 18.3 | 10.1 | 2.08 | 5.59 |
| KCl, 3.0 eq | 74.7 | 38.7 | 19.5 | 10.1 | 1.99 | 5.75 |
| KBr, 0.5 eq | 71.7 | 38.1 | 18.3 | 10.1 | 2.08 | 5.61 |
| KBr, 1.0 eq | 71.7 | 38.2 | 18.5 | 10.1 | 2.07 | 5.63 |
| KBr, 3.0 eq | 59.5 | 32.1 | 15.1 | 8.5 | 2.12 | 5.55 |
| KI, 0.5 eq | 71.0 | 38.0 | 17.9 | 10.2 | 2.12 | 5.51 |
| KI, 1.0 eq | 68.6 | 37.0 | 17.3 | 10.0 | 2.14 | 5.45 |
| KI, 3.0 eq | 51.3 | 27.3 | 13.8 | 7.7 | 1.98 | 5.37 |
| DABCO + KCl | 0.1 | 0.0 | 0.0 | 0.0 | — | — |
| DABCO + KBr | 0.2 | 0.0 | 0.0 | 0.0 | — | — |
| DABCO + KI | 0.9 | 0.1 | 0.0 | 0.1 | — | 0.58 |

DABCO is (1,4-diazabicyclo[2.2.2]octane), an organic compound with the formula N2(C2H4)3.
DABCO is a highly nucleophilic amine, which is used as a catalyst and reagent in polymerization and organic synthesis.

The results in Table 9 shows that large increases in reaction time did little to substantially improve the conversion, though did tend to improve E:Z ratio, at least under the conditions tested.

TABLE 9

Effect of reaction time on conversion and product ratio, using 50 mol % KOtBu, 3 eq Et$_3$SiH, 0.1 mL DME at 65° C.

$C_9H_{19}$—CH=CH$_2$ (1) → $C_9H_{19}$—CH=CH—SiEt$_3$ (2a) + $C_9H_{19}$—C(SiEt$_3$)=CH—... (2b) + $C_9H_{19}$—CH=CH—CH$_2$SiEt$_3$ (2c)

| Reaction Time | Conversion (%) | Yield 2a (%) | Yield 2b (%) | Yield 2c (%) | E:Z Ratio | Vinyl:Allyl Ratio |
|---|---|---|---|---|---|---|
| 4 days | 86.2 | 40.4 | 22.7 | 10.7 | 1.78 | 5.90 |
| 33 days | 81.4 | 39.9 | 15.6 | 11.2 | 2.56 | 4.97 |

Example 2.3: Screening Experiments—1-Dodecene with Hexamethyldisilane

A series of screening experiments were conducted using 1-dodecene and Hexamethyldisilane, so as to evaluate a range of conditions on silylation reactions using organodisilanes. The results are shown in Table 6.

TABLE 6

Screening experiments with 1-dodecene and various bases using 0.2 eq base, 3 eq $Me_6Si_2$, 0.1 mL solvent at 65° C. for 48 h.

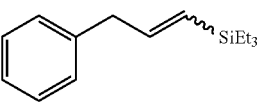

| Base | Conversion (%) | Yield 3a (%) | Yield 3b (%) | Yield 3c (%) | E:Z Ratio | Vinyl:Allyl Ratio |
| --- | --- | --- | --- | --- | --- | --- |
| KOtBu | 28.5 | 15.9 | 9.4 | 0.3 | 1.69 | 100.97 |
| KHMDS | 10.6 | 5.4 | 3.6 | 0.0 | 1.49 | 304.25 |
| NaOtBu | 0.4 | 0.0 | 0.0 | 0.0 | — | — |
| LiOtBu | 0.2 | 0.0 | 0.0 | 0.0 | — | — |
| DABCO | 0.0 | 0.0 | 0.0 | 0.0 | — | — |
| NaOEt | 0.3 | 0.0 | 0.0 | 0.0 | — | — |
| KOEt | 15.2 | 6.1 | 7.2 | 1.0 | 0.86 | 13.29 |
| NaOAc | 0.1 | 0.0 | 0.0 | 0.0 | — | — |
| KOAc | 0.0 | 0.0 | 0.0 | 0.0 | — | — |
| NaOMe | 0.2 | 0.0 | 0.0 | 0.0 | — | — |
| KOMe | 3.1 | 0.7 | 2.0 | 0.0 | 0.35 | — |
| $Cs_2O_3$ | 0.0 | 0.0 | 0.0 | 0.0 | — | — |
| $K_2CO_3$ | 0.0 | 0.0 | 0.0 | 0.0 | — | — |
| KOtAmylate | 25.6 | 14.3 | 8.2 | 0.2 | 1.74 | 114.84 |
| TMAF | 0.5 | 0.0 | 0.0 | 0.0 | — | — |
| KF | 0.1 | 0.0 | 0.0 | 0.0 | — | — |

Example 2.4: Substrates with Non-Conjugated Terminal Olefins

A range of organosilanes and organodisilanes were reacted with a range of non-conjugated terminal olefinic substrates to demonstrate the general applicability of the disclosed methods. Representative reactions are presented here.

Example 2.4.1: Silylation of 1-Octene

In a preliminary experiment, 1-octene was reacted with Et3Si—H (1 eq) and KOtBu (0.2 eq) for 2 days as 65° C. The reaction proceeded to form a mixture predominantly of (1-triethylsilyl)-1-octene and (1-triethylsilyl)-2-octene, as identified by GC-MS and $^1$H-nmr. No hydrosilylation products were observed in the mixture by GC-MS. (see FIGS. 1A-D).

Example 2.3.2: Silylation of 1-Docdecene

Figure 2:
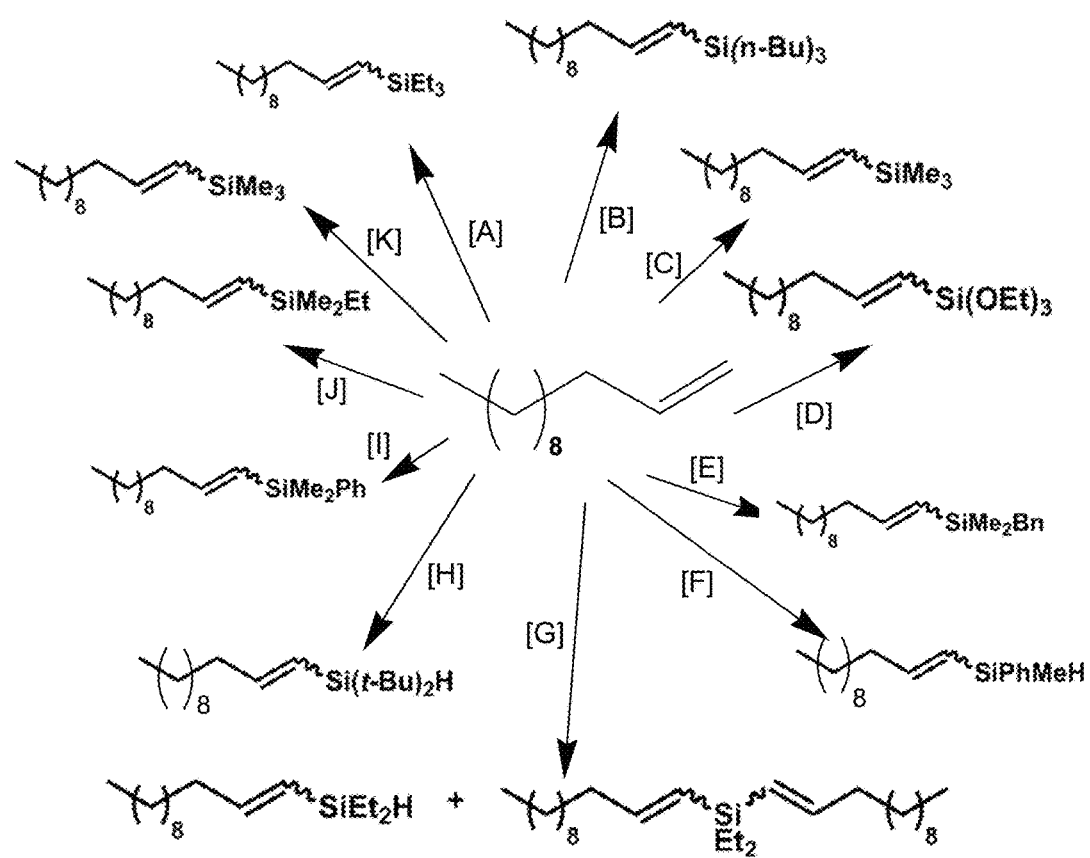
FIG. 2 shows an array of representative reaction products resulting from the silylation of 1-dodecene. The wavy line represents a mixture of E- and Z-isomers. The corresponding silylating agent used for each reaction are: [A], H—Si(ethyl)$_3$; [B], H—Si(n-butyl)$_3$; [C], (methyl)$_3$Si—Si(methyl)$_3$; [D], H—Si(ethoxy)$_3$ with low conversion; [E], H—Si(methyl)$_2$(benzyl), low conversion observed; [F] H$_2$Si(phenyl)(methyl), no tethered product observed, with low conversion; [G], H$_2$Si(ethyl)$_2$; [H], H$_2$Si(tert-butyl)$_2$; [I], H—Si(methyl)$_2$(phenyl), with low conversion; [J] H—Si(Me)$_2$(Et); [K], (methyl)$_3$Si—Si(methyl)$_3$.

In addition to the results reported above, 1-dodecene was reacted with a range of silylating agents (both organosilanes and organodisilanes). Reactions of 1-dodecene resulted in the formation of products shown in FIG. 2.

Example 2.4.3: Silylation of Other Non-Conjugated Substrates

The compounds in Table 7 were also prepared using $Et_3SiH$ as the exemplary organosilane and/or $Me_3Si$—$SiMe_3$ as exemplary organodisilane

TABLE 7

Products obtained using $Et_3SiH/Me_3Si$—$SiMe_3$ as exemplary silylating reagents; products characterized in situ unless otherwise stated.

| Substrate | Product | Comment |
| --- | --- | --- |
| Allyl benzene | 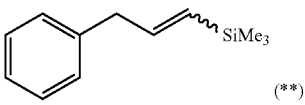 [SMILES: C[Si](C)(C)C=CCc1ccccc1] | Prepared using $Et_3SiH$ |
| | | Prepared using $Me_3Si$—$SiMe_3$ (**) |

TABLE 7-continued

Products obtained using Et₃SiH/Me₃Si—SiMe₃ as exemplary silylating reagents; products characterized in situ unless otherwise stated.

| Substrate | Product | Comment |
|---|---|---|
| Camphene | [structure: camphene-derived vinyl-SiEt₃] | Prepared using Et₃SiH |
| 1-Dodecene | [structure: CH₃(CH₂)₈CH=CH–SiEt₃] | Prepared using Et₃SiH; product isolated |
|  | [structure: CH₃(CH₂)₈CH=CH–SiMe₃] | Prepared using Me₃Si—SiMe₃; product isolated |
| (R)-(+)-Limonene | [structure: limonene-derived vinyl-SiEt₃] | Prepared at 100° C.; Prepared using Et₃SiH |
| 5-Phenyl-1-pentene | [structure: Ph(CH₂)₃CH=CH–SiEt₃] | Prepared using Et₃SiH; isolated |
|  | [structure: Ph(CH₂)₃CH=CH–SiMe₃] | Prepared using Me₃Si—SiMe₃ |

(**) an unidentified isomer of bis-silylation was also detected

Example 2.5: Substrates with Conjugated Terminal Olefins

A range of organosilanes and organodisilanes were reacted with a range of non-conjugated terminal olefinic substrates to demonstrate the general applicability of the disclosed methods. Representative reactions are presented in Table 8.

TABLE 8

Products obtained using various silylating reagents; products characterized in situ unless otherwise stated.

| Substrate | Product | Comment |
|---|---|---|
| N-allyl carbazole | [structure: carbazole-N-CH₂CH₂-SiEt₃] | Prepared using Et₃SiH |

TABLE 8-continued

Products obtained using various silylating reagents; products characterized in situ unless otherwise stated.

| Substrate | Product | Comment |
|---|---|---|
| | 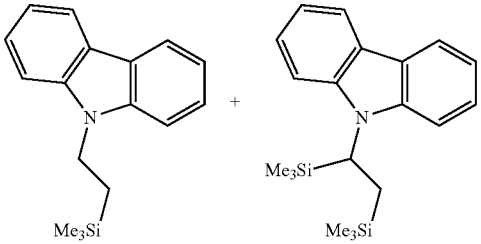 [SMILES: C[Si](C)(C)CCn1c2ccccc2c2ccccc21 ; C[Si](C)(C)CC(n1c2ccccc2c2ccccc21)[Si](C)(C)C] | Prepared using Me$_3$Si—SiMe$_3$; product isolated |
| 4-Allyl-N,N-diphenylaniline | 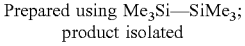 | Prepared using Me$_3$Si—SiMe$_3$ |
| 1-vinyl naphthalene | 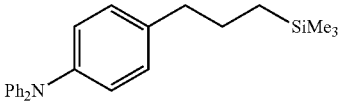 | Prepared using Et$_3$SiH; product isolated |
| | 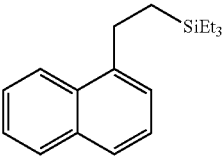 | Prepared using Me$_2$EtSiH; lower conversions |
| | 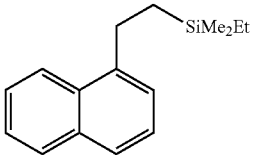 | Prepared using (Et)$_2$SiH$_2$; tethering possible at ca. 100° C. |
| | 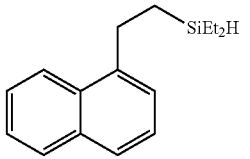 | Prepared using Me$_2$PhSiH; lower conversions |
| | 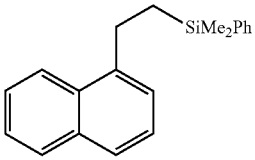 | Prepared using (n-Bu)$_3$SiH |
| | 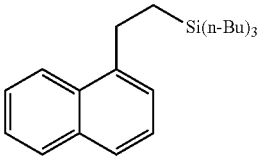 | Prepared using (t-Bu)$_2$SiH$_2$; no tethering detected under conditions tested |

TABLE 8-continued

Products obtained using various silylating reagents; products characterized in situ unless otherwise stated.

| Substrate | Product | Comment |
|---|---|---|
| | [1-naphthyl-CH₂CH₂-SiMe₃] | Prepared using Me₃Si—SiMe₃ |
| | [1-naphthyl-CH=CH-SiMePhH] + [1-naphthyl-CH₂CH₂-SiMePhH] + [bis(1-naphthylvinyl)SiMePh] | unclear whether tethering is via dehydrogenation silylation or through hydrosilylation |
| 2-vinyl naphthalene | [2-naphthyl-CH₂CH₂-SiEt₃] | Prepared using Et₃SiH; higher temperatures required |
| | [2-naphthyl-CH₂CH₂-SiMe₃] | Prepared using Me₃Si—SiMe₃; product isolated |
| vinylferrocene | [ferrocenyl-CH₂CH₂-SiEt₃] | Prepared using Et₃SiH; isolated |
| p,α-dimethylstyrene | [4-tolyl-CH(Me)CH₂-SiMe₃] | Prepared using Me₃Si—SiMe₃; product isolated |

Example 2.6: Specific Examples

The following reactions were conducted according to the methods described in Example 2.1:

Example 2.6.1: 5-Phenyl-1-pentene with HShEt)₃

Figure 3A:
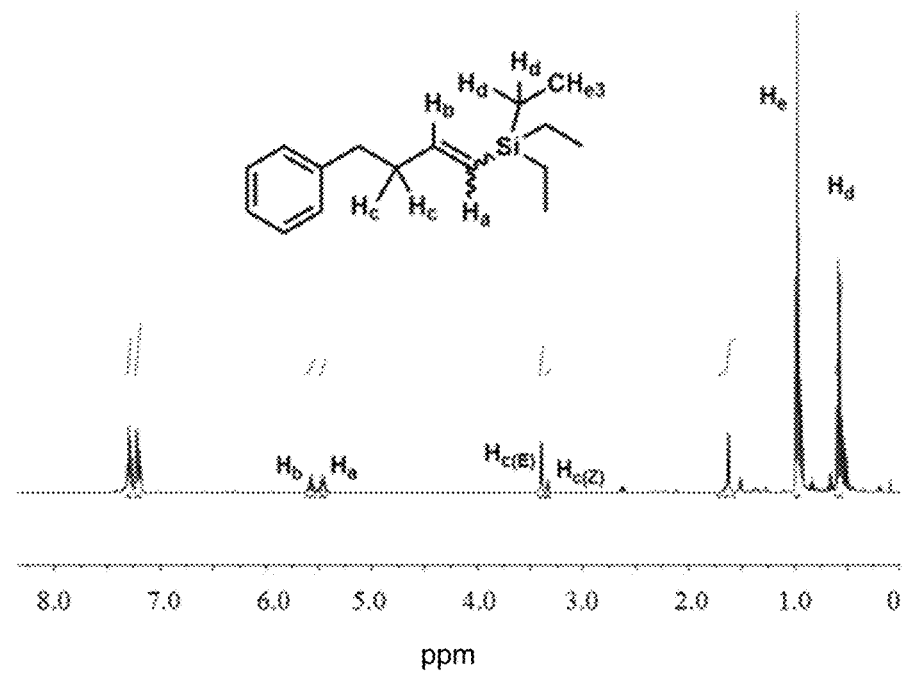
FIG. 3(A-B) show the $^1$H-NMR spectrum (FIG. 3(A)) and $^{13}$C-NMR spectrum (FIG. 3(B)) of the product of the reaction between 5-phenyl-1-pentene and HSi(Et)$_3$.
Figure 3B:
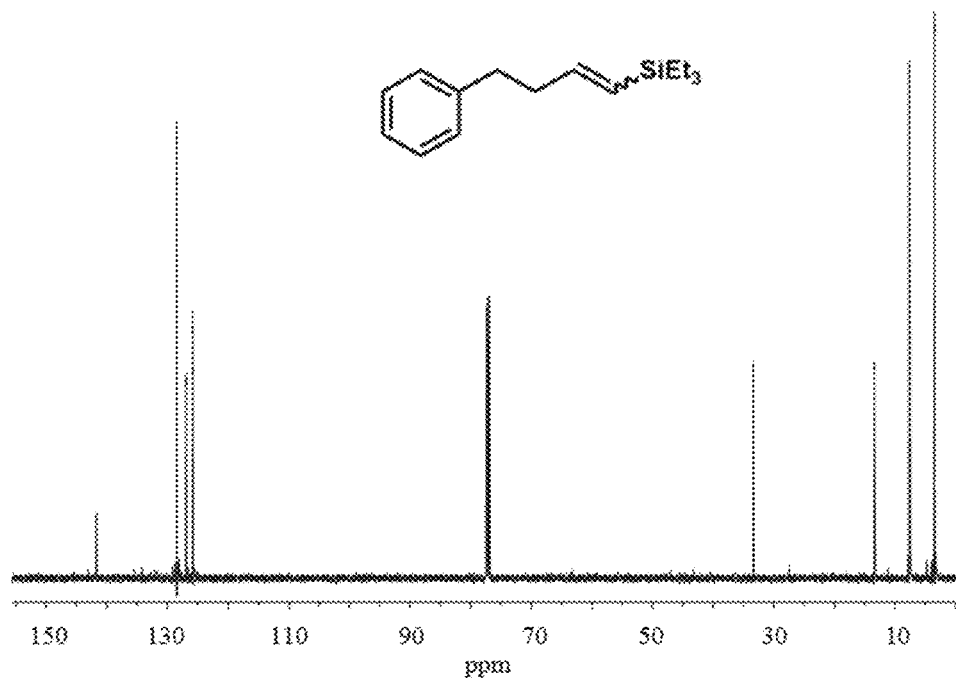

See FIG. 3(A-B): $^1$H-NMR (500 MHz, CDCl$_3$) δ 7.32-7.27 (m, 2H), 7.24-7.17 (m, 3H), 5.61-5.54 (m, 1H), 5.50-5.42 (m, 1H), 3.40 (d, J=7.1 Hz, 2H), 1.63 (ddd, J=8.6, 1.6, 0.8 Hz, 2H), 0.98 (t, J=7.9 Hz, 6H), 0.58 (q, J=7.9 Hz, 4H); $^{13}$C-NMR (126 MHz, CDCl$_3$) δ 141.704, 128.484, 128.478, 126.926, 125.872, 125.808, 33.391, 13.482, 7.576, 3.452.

Example 2.6.2: 1-Vinyl naphthalene with HSi(Et)₃

Figure 4A:
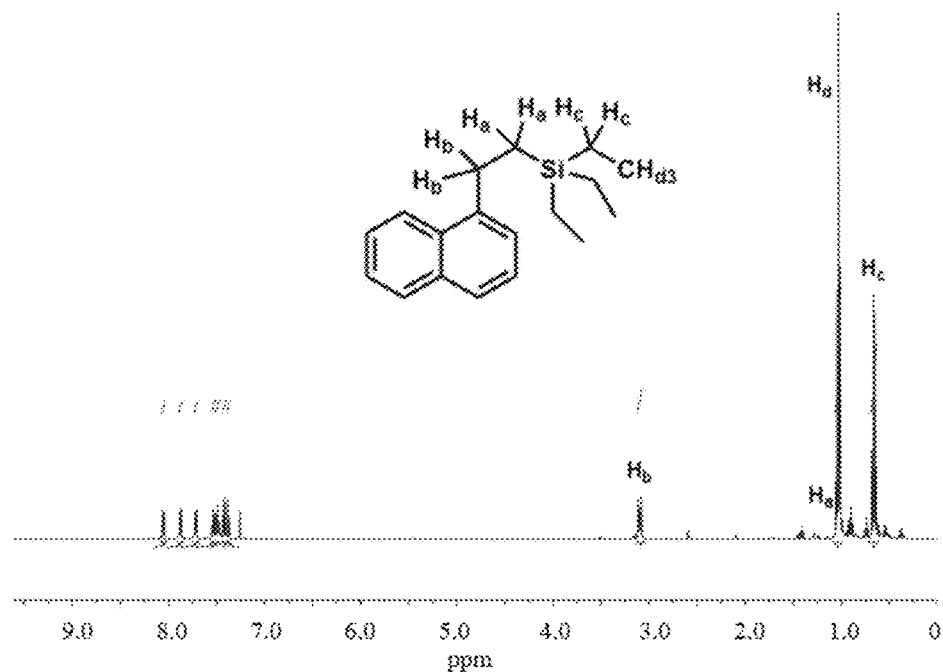
FIG. 4(A-B) show the $^1$H-NMR spectrum (FIG. 4(A)) and $^{13}$C-NMR spectrum (FIG. 4(B)) of the product of the reaction between 1-vinyl naphthalene and HSi(Et)$_3$.
Figure 4B:
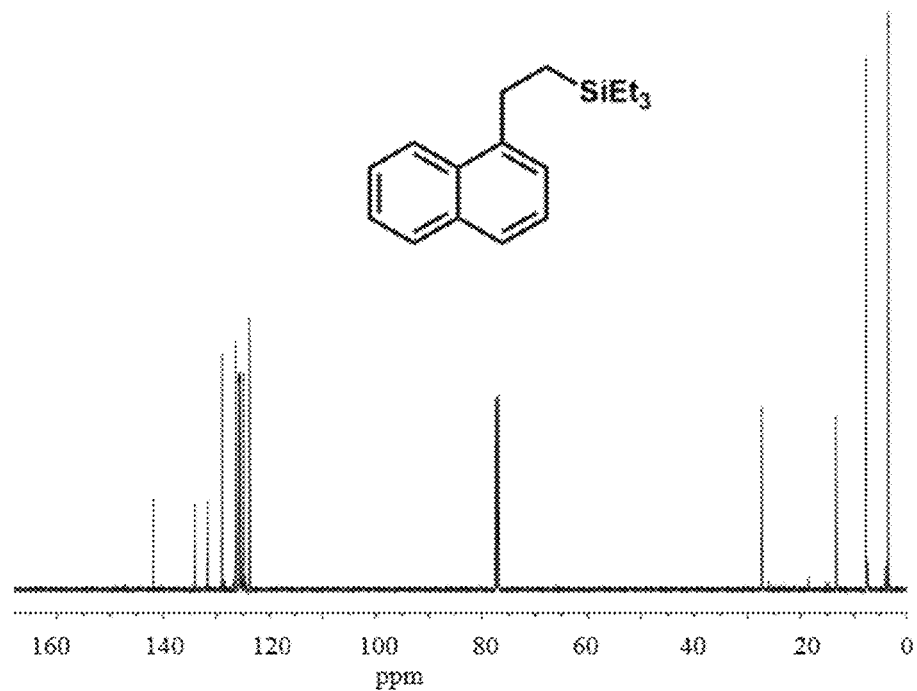
Figure 5A:
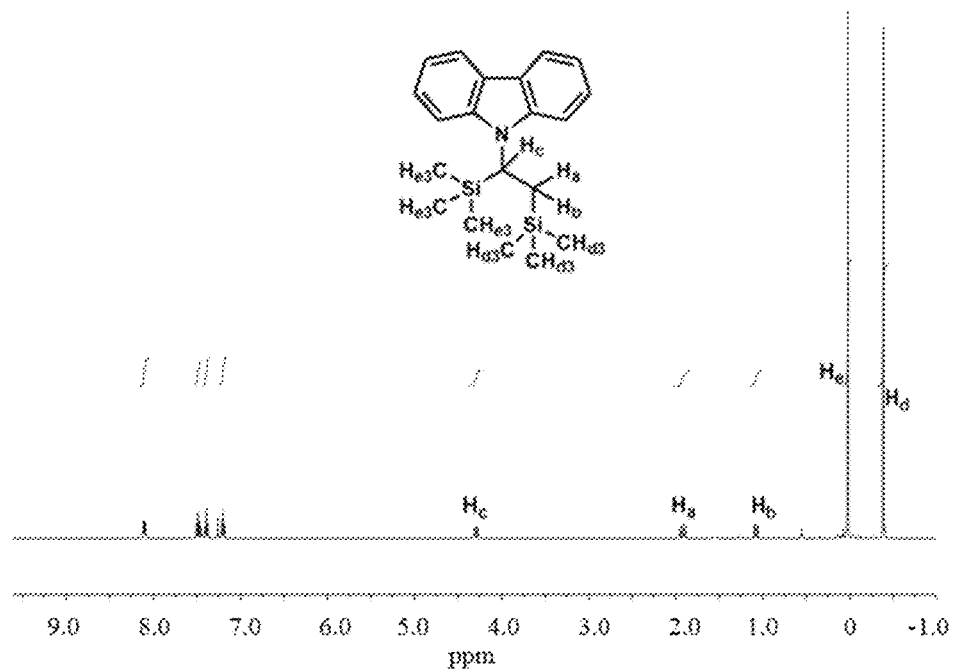
FIG. 5(A-D) show the $^1$H-NMR spectra (FIG. 5(A,C)) and $^{13}$C-NMR spectra (FIG. 5(B,D)) of the product of the reaction between N-allyl carbazole and (Me)$_s$Si—Si(Me)$_3$.
Figure 5B:
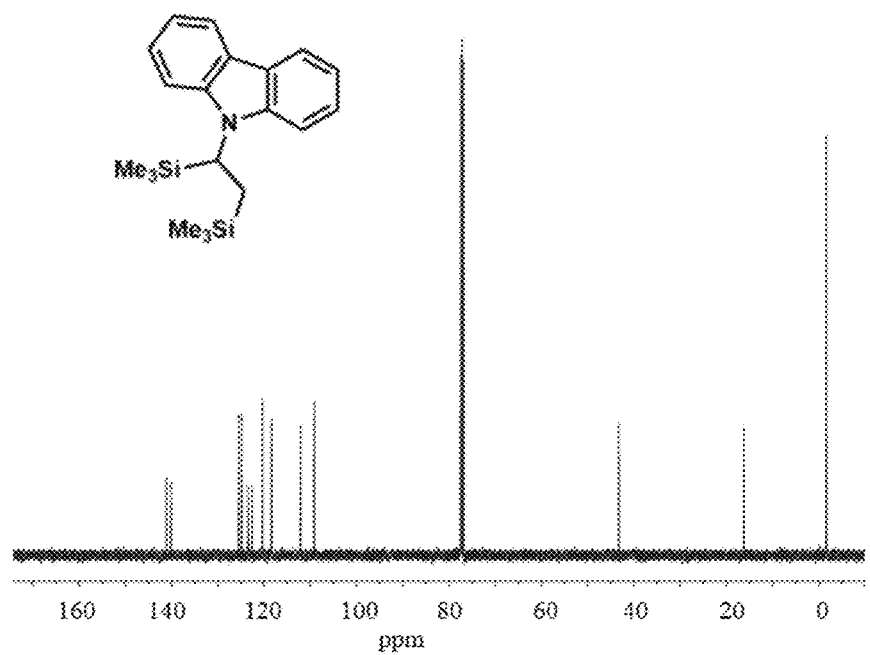
Figure 5C:
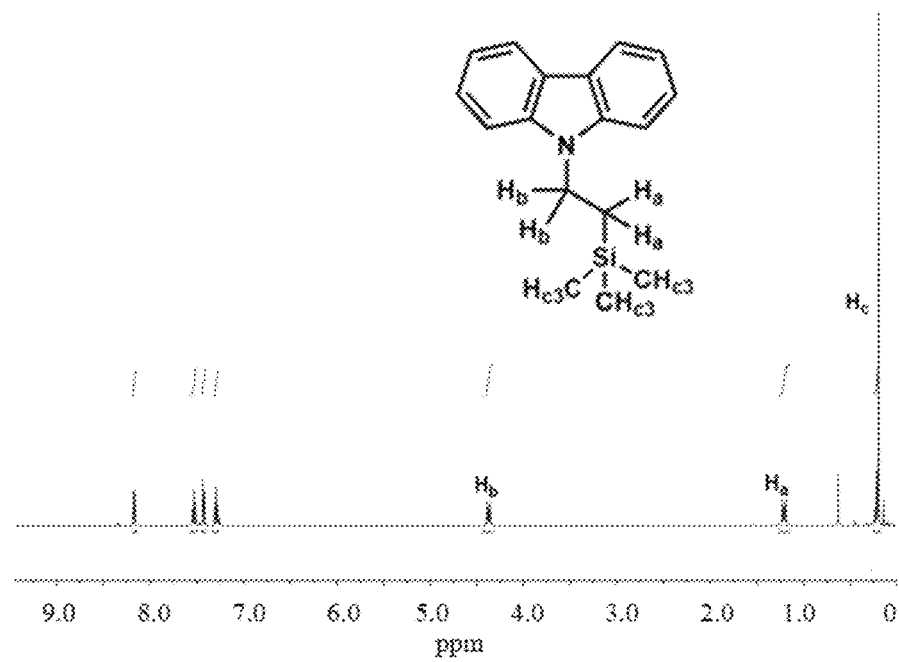
Figure 5D:
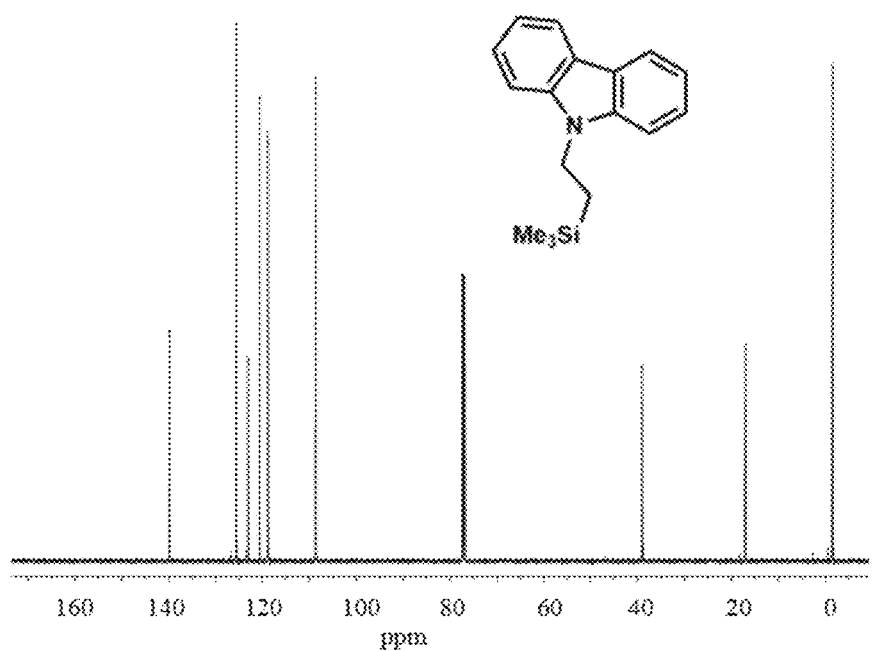

See FIG. 4(A-B): (500 MHz, CDCl$_3$) δ 8.05 (d, J=8.1 Hz, 1H), 7.88 (d, J=7.4 Hz, 1H), 7.72 (ddx, J=8.0, 1.4 Hz, 1H), 7.53 (ddd, J=8.4, 6.8, 1.5 Hz, 1H), 7.49 (ddd, J=8.1, 6.8, 1.4 Hz, 1H), 7.42 (dd, J=8.0, 7.1 Hz, 1H), 7.38 (d, J=7.0 Hz, 1H), 3.12-3.07 (m, 2H), 1.08-1.00 (m, 11H), 0.66 (q, J=7.9 Hz, 6H). $^{13}$C-NMR (126 MHz, cdcl$_3$) δ 141.860, 134.051, 131.622, 128.942, 126.401, 125.829, 125.770, 125.497, 124.904, 123.793, 27.326, 13.402, 7.695, 3.457.

Example 2.6.3: N-allyl carbazole with (Me)sSi-Si(Me)₃-Disilylated Product

See FIG. 5(A-D): $^1$H-NMR (500 MHz, Chloroform-d) δ 8.10 (ddt, J=7.9, 4.6, 0.9 Hz, 2H), 7.49 (t, J=8.6 Hz, 2H), 7.39 (td, J=8.1, 1.1 Hz, 2H), 7.20 (ddt, J=8.6, 7.9, 1.2 Hz, 2H), 4.29 (dd, J=13.6, 3.1 Hz, 1H), 1.92 (dd, J=15.4, 13.4 Hz, 1H), 1.07 (dd, J=15.3, 3.5 Hz, 1H), 0.02 (s, 9H), −0.38 (s, 9H). $^{13}$C-NMR (126 MHz, cdcl$_3$) δ 141.101, 140.097, 125.487, 124.847, 123.483, 122.585, 120.284, 120.216, 118.290, 118.260, 111.970, 109.027, 43.207, 16.241, −1.545. $^{13}$C-NMR (126 MHz, cdcl$_3$) δ 141.101, 140.097, 125.487, 124.847, 123.483, 122.585, 120.284, 120.216, 118.290, 118.260, 111.970, 109.027, 43.207, 16.241, −1.545

Example 2.6.3: N-allyl carbazole with (Me)sSi-Si(Me)₃-monosilylated product

See FIG.: ¹H-NMR (500 MHz, Chloroform-d) δ 8.17 (dt, J=7.8, 0.9 Hz, 2H), 7.53 (ddd, J=8.3, 7.1, 1.2 Hz, 2H), 7.43 (dt, J=8.3, 0.8 Hz, 2H), 7.29 (ddd, J=8.0, 7.1, 1.0 Hz, 2H), 4.45-4.31 (m, 2H), 1.29-1.16 (m, 2H), 0.19 (s, 9H). ¹³C-NMR (126 MHz, cdcl₃) δ 139.887, 125.624, 123.110, 120.554, 118.774, 108.606, 38.981, 17.009, −1.574.

As those skilled in the art will appreciate, numerous modifications and variations of the present invention are possible in light of these teachings, and all such are contemplated hereby. All references cited within this specification are incorporated by reference, at least for their teachings in the context of their use.

What is claimed:

1. A method comprising contacting at least one organic substrate comprising a terminal olefin with:
   (a) an organosilane, organodisilane, or mixture thereof; and
   (b) an alkali metal alkoxide, an alkali metal hydroxide, an alkaline earth metal alkoxide, an alkaline earth metal hydroxide, an alkali metal amide, or a mixture thereof, such that the contacting results in the formation of a terminally silylated olefinic product.

2. The method of claim 1, wherein the organosilane has a structure of Formula (I) and the organodisilane has a structure of Formula (II):

$(R)_{3-m}Si(H)_{m+1}$  (I)

$(R)_{3-m}(H)_m Si\text{—}Si(R)_{3-m}(H)_m$  (II)

where: m is independently 0, 1, or 2; and each R is independently optionally substituted $C_{1-24}$ alkyl or optionally substituted $C_{1-24}$ heteroalkyl, optionally substituted $C_{2-24}$ alkenyl or optionally substituted $C_{2-24}$ heteroalkenyl, optionally substituted $C_{2-24}$ alkynyl or optionally substituted $C_{2-24}$ heteroalkynyl, optionally substituted 6 to 18 ring membered aryl or optionally substituted 5 to 18 ring membered heteroaryl, optionally substituted 6 to 18 ring-membered alkaryl or optionally substituted 5 to 18 ring-membered heteroalkaryl, optionally substituted 6 to 18 ring-membered aralkyl or optionally substituted 5 to 18 ring-membered heteroaralkyl, optionally substituted —O—$C_{1-24}$ alkyl or optionally substituted —O—$C_{1-24}$ heteroalkyl, optionally substituted 6 to 18 ring-membered aryloxy or optionally substituted 5 to 18 ring-membered heteroaryloxy, optionally substituted 6 to 18 ring-membered alkaryloxy or optionally substituted 5 to 18 ring-membered heteroalkaryloxy, or optionally substituted 6 to 18 ring-membered aralkoxy or optionally substituted 5 to 18 ring-membered heteroaralkoxy, and, if substituted, the substituents may be phosphonato, phosphoryl, phosphanyl, phosphino, sulfonato, $C_1$-$C_{20}$ alkylsulfanyl, $C_5$-$C_{20}$ arylsulfanyl, $C_1$-$C_{20}$ alkylsulfonyl, $C_5$-$C_{20}$ arylsulfonyl, $C_1$-$C_{20}$ alkylsulfinyl, 5 to 12 ring-membered arylsulfinyl, sulfonamido, amino, amido, imino, nitro, nitroso, hydroxyl, $C_1$-$C_{20}$ alkoxy, $C_5$-$C_{20}$ aryloxy, $C_2$-$C_{20}$ alkoxycarbonyl, $C_5$-$C_{20}$ aryloxycarbonyl, carboxyl, carboxylato, mercapto, formyl, $C_1$-$C_{20}$ thioester, cyano, cyanato, thiocyanato, isocyanate, thioisocyanate, carbamoyl, epoxy, styrenyl, silyl, silyloxy, silanyl, siloxazanyl, boronato, boryl, or halogen, or a metal-containing or metalloid-containing group, where the metalloid is Sn or Ge, where the substituents optionally provide a tether to an insoluble or sparingly soluble support media comprising alumina, silica, or carbon.

3. The method of claim 2, where m is 1 or 2, further comprising reacting the terminally silylated olefinic product with an aromatic substrate under conditions sufficient to silylate the aromatic substrate with the terminally silylated olefinic product to form a product of the silylation of the aromatic substrate with the terminally silylated olefinic product.

4. The method of claim 3, wherein the aromatic substrate comprises at least one of the following moieties:

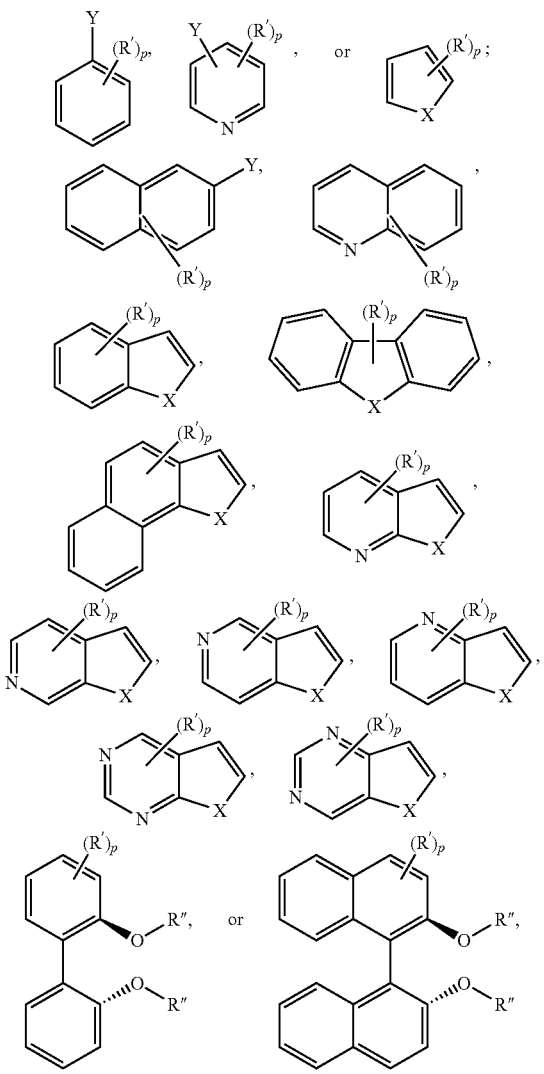

where
X is N—R″, O, or S;
Y is H, N(R″)₂, O—R″, or S—R″
p is 0 to 4, 0 to 3, 0 to 2, or 0 to 1;
R' is a functional group "Fn," or (R')ₚ is an optionally substituted fused alicyclic, heteroalicyclic, aryl or heteroaryl moiety, wherein "Fn" is $C_{1-24}$ alkyl, $C_{2-24}$ alkenyl, $C_{2-24}$ alkynyl, $C_{6-24}$ awl, $C_{7-24}$ alkaryl, $C_{6-24}$ aralkyl, halo, $C_{1-24}$ alkoxy, $C_{2-24}$ alkenyloxy, $C_{2-24}$ alkynyloxy, $C_{6-24}$ aryloxy, $C_{6-24}$ aralkyloxy, $C_{6-24}$ alkaryloxy, $C_{1-24}$ alkylcarbonyl, $C_{6-24}$ arylcarbonyl, $C_{2-24}$ alkylcarbonyloxy, $C_{6-24}$ arylcarbonyloxy, $C_{2-24}$ alkoxycarbonyl ((CO)—O-alkyl), $C_{6-24}$ aryloxycarbonyl, halocarbonyl $C_{2-24}$ alkylcarbonato, $C_{6-24}$ arylcarbonato, carboxy (—COOH), carboxylato (—COO—), carbamoyl, mono-($C_{1-24}$ alkyl substituted carbamoyl, di-($C_{1-24}$ alkyl)-substituted carbamoyl, mono-($C_{5-24}$ aryl)-substituted carbamoyl, di-($C_{5-24}$ aryl)substituted carbamoyl, thiocarbamoyl (—(CS)NH$_2$), mono-($C_{1-24}$ alkyl)-substituted thiocarbamoyl, di-($C_{1-24}$ substituted thiocarbamoyl, mono-($C_{6-24}$ aryl)substituted thiocarbamoyl, di-($C_{6-24}$aryl)-substituted thiocarbamoyl, carbamido, cyano, cyanato, thiocyanato, formyl, thioformyl, amino, mono-($C_{1-24}$ alkyl)-substituted amino, di-($C_{1-24}$ alkyl)-substituted amino, mono-($C_{6-24}$ aryl) substituted amino, di-($C_{6-24}$ aryl)-substituted amino, $C_{1-24}$ alkylamido, $C_{6-24}$ arylamido, imino, alkylimino, arylimino, nitro, nitroso, sulfonate, $C_{1-24}$ alkylsulfanyl (—S-alkyl), $C_{6-24}$ arylsulfanyl (—S-aryl), $C_{1-24}$ alkylsulfinyl (—(SO)-alkyl), $C_{6-24}$ arylsulfinyl (—(SO)-aryl), $C_{1-24}$ alkylsulfonyl, mono-$C_{1-24}$ alkylaminosulfonyl, di-$C_{1-24}$ alkylaminosulfonyl, $C_{6-24}$ aryl sulfonyl, or boronato; and R" is an amine protecting group or an optionally substituted alkyl, aryl, heteroaryl, alkaryl or alk-heteroaryl;

and wherein the terminally silylated olefinic product is introduced to the aromatic substrate on a 5 or 6-membered ring of the aromatic substrate.

5. The method of claim 2, where m is 1 or 2, further comprising reacting the terminally silylated olefinic product with an organic substrate comprising a terminal alkyne, to form a silylated terminal alkynyl moiety.

6. The method of claim 5, wherein the organic substrate comprising the terminal alkynyl C—H bond has a formula:

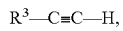

$$R^3\text{—}C\equiv C\text{—}H,$$

where $R^3$ comprises an optionally substituted $C_{1-18}$ alkyl, optionally substituted $C_{2-18}$ alkenyl, optionally substituted $C_{2-18}$ alkynyl, optionally substituted $C_{1-18}$ membered heteroalkyl, optionally substituted 6-18 ring membered aryl, optionally substituted 6-18 ring membered aryloxy, optionally substituted 6-18 ring membered aralkyl, optionally substituted 6-18 ring membered aralkyloxy, optionally substituted 5-18 ring membered heteroaryl, optionally substituted 5-18 ring membered heteroaryloxy, optionally substituted 5-18 ring membered heteroarylalkyl, optionally substituted 5-18 ring membered heteroaralkyloxy, or optionally substituted metallocene.

7. The method of claim 2, where m is 0, 1, or 2 further comprising reacting the terminally silylated olefinic product with:

(a) water, alcohol, hydrogen cyanide, hydrogen chloride, dihalogen, or carboxylic acid under conditions known to give corresponding hydroxy, alkoxy, cyano, halo, or ester products;

(b) an alkyl halide, an aryl halide, or a heteroaryl halide, in the presence of a palladium catalyst, under cross-coupling conditions sufficient to replace the silyl group by the corresponding alkyl, aryl, or heteroaryl moiety;

(c) alkyl lithium or potassium tert-butoxide, then with an alkyl halide to form an alkyl substituted vinyl silyl product;

(d) IC1 or I$_2$ so as to form a terminal vinyl iodide with the displacement of the silyl group;

(e) a polyolefin so as to form a silane grafted polyolefin;

(f) an organic peroxide to form a terminal silylated peroxide, which when treated with a strong acid forms an aldehyde moiety;

(g) a fluoride source, hydrogen peroxide, and base to form an aldehyde or ketone, according to the well-known Tamao-Fleming Oxidation reaction;

(h) an iodosyl benzene to form a vinyliodonium tetrafluoroborate; or (i) an acid chloride, aldehyde, epoxide, imine, ketal, or ketone, with a Lewis acid, for example TiCl$_4$ or BF$_3$*OEt$_2$, under conditions generally recognized as associated with the Hosomi-Sakurai Allylation reaction to form the corresponding allyl derivative.

8. The method of claim 1, wherein the organosilane or organodisilane is an organosilane.

9. The method of claim 1, wherein the organosilane or organodisilane is an organodisilane.

10. The method of claim 1, wherein the organosilane comprises (R)$_3$SiH, (R)$_2$SiH$_2$, or (R)SiH$_3$, where R is independently at each occurrence optionally substituted $C_{1-18}$ alkoxy, optionally substituted $C_{1-18}$ alkyl, optionally substituted $C_{2-18}$ alkenyl, optionally substituted 6-18 ring membered aryl, optionally substituted 6-18 ring membered aryloxy, optionally substituted 5-18 ring membered heteroaryl, optionally substituted 6-18 ring membered aralkyl, optionally substituted 6-18 ring membered optionally substituted aralkyloxy, or optionally substituted 6-10 ring membered heteroaralkyl.

11. The method of claim 1, wherein the organodisilane comprises (R)$_{3-m}$(H)$_m$Si—Si(R)$_{3-m}$(H)$_m$ or (R)$_3$Si—Si(R)$_3$, where R is independently at each occurrence optionally substituted $C_{1-18}$ alkoxy, optionally substituted $C_{1-18}$ alkyl, optionally substituted $C_{2-18}$ alkenyl, optionally substituted $C_{6-18}$ aryl, optionally substituted $C_{6-18}$ aryloxy, optionally substituted 5-18 ring membered heteroaryl, optionally substituted 6-18 ring membered aralkyl, optionally substituted 6-18 ring membered aralkyloxy, or optionally substituted 6-18 ring membered heteroaralkyl.

12. The method of claim 1, wherein R is independently at each occurrence methyl, ethyl, propyl, butyl, pentyl, phenyl, biphenyl, phenoxy, benzyl, benzyloxy, or pyridinyl.

13. The method of claim 1, wherein the alkali metal hydroxide comprises sodium hydroxide (NaOH), potassium hydroxide (KOH), or a mixture thereof.

14. The method of claim 1, wherein the alkali metal alkoxide comprises a sodium alkoxide, potassium alkoxide, or mixture thereof.

15. The method of claim 1, wherein the alkoxide comprises a linear, branched, or cyclic saturated hydrocarbon group containing 1 to 12 carbon atoms.

16. The method of claim 1, wherein the alkoxide comprises sodium methoxide, sodium ethoxide, sodium n-propoxide, sodium isopropoxide, sodium n-butoxide, sodium sec-butoxide, sodium tert-butoxide, sodium n-pentoxide, sodium 2-pentoxide, sodium 3-pentoxide, sodium iso-pentoxide, potassium methoxide, potassium ethoxide, potassium n-propoxide, potassium isopropoxide, potassium n-butoxide, potassium sec-butoxide, potassium tert-butoxide, potassium n-pentoxide, potassium 2-pentoxide, potassium 3-pentoxide, or potassium iso-pentoxide.

17. The method of claim 1, wherein the at least one organic substrate comprising the terminal olefin has a formula:

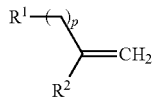

where p is 0 or 1; $R^1$ and $R^2$ independently comprises H, an optionally substituted $C_{1-18}$ alkyl, optionally substituted $C_{2-18}$ alkenyl, optionally substituted $C_{2-18}$ alkynyl, optionally substituted $C_{6-18}$ aryl, optionally substituted $C_{1-18}$ heteroalkyl, optionally substituted 5-6 ring membered heteroaryl, optionally substituted 5-6 ring membered aralkyl, optionally substituted 5-6 ring membered heteroaralkyl, or optionally substituted metallocene, provided that $R^1$ and $R^2$ are not both H.

18. The method of claim 17, wherein each $R^1$ and $R^2$ independently comprises:
   (a) an optionally substituted $C_{1-18}$ linear alkyl, an optionally substituted branched $C_{1-18}$ alkyl, or an optionally substituted $C_{3-18}$ cycloalkyl;
   (b) an optionally substituted linear $C_{2-18}$ alkenyl, an optionally substituted branched $C_{2-18}$ alkenyl, or an optionally substituted $C_{3-18}$ cycloalkenyl;
   (c) an optionally substituted linear $C_{1-18}$ heteroalkyl, an optionally substituted branched $C_{1-18}$ heteroalkyl, or an optionally substituted $C_{1-18}$ heterocycloalkyl;
   (d) an optionally substituted 6-18 ring membered aryl, an optionally substituted 6-18 ring membered aralkyl, an optionally substituted 6-18 ring membered aryloxy, an optionally substituted 6-18 ring membered aralkyloxy, optionally substituted 5-18 ring membered heteroaryl, or an optionally substituted 5-18 ring membered heteroaralkyl, optionally substituted 5-18 ring membered heteroaryloxy, or an optionally substituted optionally substituted 5-18 ring membered heteroaralkyloxy; or
   (e) hydrogen, provided that $R^1$ and $R^2$ are not both hydrogen when p=0.

19. The method of claim 17, wherein the terminally silylated olefinic product has a formula:

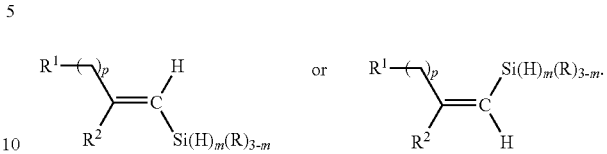

20. The method of claim 17, wherein when p=1, the terminally silylated olefinic product has a formula:

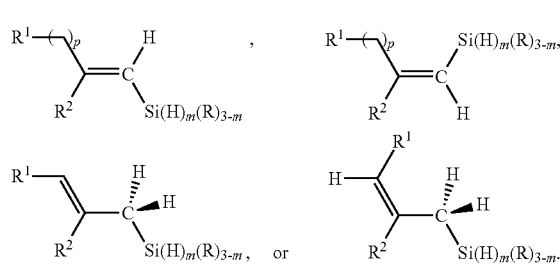

21. The method of claim 17, further comprising polymerizing the terminally silylated olefinic product.

22. The method of claim 1, wherein the method consists essentially of contacting at least one organic substrate comprising a terminal olefin with a mixture of an organosilane or organodisilane and an alkali metal alkoxide and/or an alkali metal hydroxide, such that the contacting results in the formation of a terminally silylated olefinic product.

23. The method of claim 1, wherein the method is conducted in the absence of added transition metal ions or catalysts.

* * * * *